United States Patent
Wulhfard et al.

(10) Patent No.: US 10,647,760 B2
(45) Date of Patent: May 12, 2020

(54) ANTIBODIES FOR TREATMENT AND DIAGNOSIS OF INFLAMMATORY BOWEL DISEASE

(71) Applicant: PHILOGEN S.P.A., Siena (IT)

(72) Inventors: Sarah Wulhfard, Baden (CH); Alessandra Villa, Zurich (CH); Catherine Pemberton Ross, Brugg (CH); Francesca Pretto, Zurich (CH); Filippa Fleetwood, Otelfmgen (CH)

(73) Assignee: PHILOGEN S.P.A., Siena (IT)

(*) Notice: Subject to any disclaimer, the term of this patent is extended or adjusted under 35 U.S.C. 154(b) by 60 days.

(21) Appl. No.: 16/060,766

(22) PCT Filed: Dec. 9, 2016

(86) PCT No.: PCT/EP2016/080462
§ 371 (c)(1),
(2) Date: Jun. 8, 2018

(87) PCT Pub. No.: WO2017/097990
PCT Pub. Date: Jun. 15, 2017

(65) Prior Publication Data
US 2019/0062414 A1    Feb. 28, 2019

(30) Foreign Application Priority Data

Dec. 11, 2015  (GB) .................................. 1521918.1
Feb. 15, 2016  (GB) .................................. 1602621.3
Apr. 15, 2016  (GB) .................................. 1606607.8

(51) Int. Cl.
| | | |
|---|---|---|
| C07K 16/18 | (2006.01) | |
| C07K 16/28 | (2006.01) | |
| A61K 47/68 | (2017.01) | |
| A61K 39/00 | (2006.01) | |
| C07K 16/40 | (2006.01) | |

(52) U.S. Cl.
CPC .......... *C07K 16/18* (2013.01); *A61K 47/6813* (2017.08); *A61K 47/6843* (2017.08); *C07K 16/28* (2013.01); *C07K 16/40* (2013.01); *A61K 2039/505* (2013.01); *C07K 2317/21* (2013.01); *C07K 2317/33* (2013.01); *C07K 2317/528* (2013.01); *C07K 2317/56* (2013.01); *C07K 2317/565* (2013.01); *C07K 2317/60* (2013.01); *C07K 2317/622* (2013.01); *C07K 2317/92* (2013.01)

(58) Field of Classification Search
None
See application file for complete search history.

(56) References Cited

FOREIGN PATENT DOCUMENTS

WO    2006/050834 A2    5/2006

OTHER PUBLICATIONS von Lukowicz et al. Human Antibody Against C Domain of Tenascin-C Visualizes Murine Atherosclerotic Plaques Ex Vivo. J Nucl Med 2007; 48:582-587 (Year: 2007).*

Ebbinghaus et al. Engineered vascular-targeting antibody-interferon-c fusion protein for cancer therapy. Int. J. Cancer: 116, 304-313 (2005). (Year: 2005).*

Zavada et al., "Serum tenascin-C discriminates patients with active SLE from inactive patients and healthy controls and predicts the need to escalate immunosuppressive therapy: a cohort study", Arthritis Research & Therapy, Nov. 25, 2015, pp. 1-11, (17) 341, BioMed Central, London, United Kingdom.

Brack et al., "Tumor-targeting properties of novel antibodies specific to the large isoform of tenascin-C", Clinical Cancer Research, May 15, 2006, pp. 3200-3208, vol. 12. No. 10, American Association for Cancer Research, Philadelphia, PA.

Tandara, "Tenascin-C als Parameter der EntzÜndungsaktivitat bei Colitis ulcerosa", Retrieved from the Internet: http://archiv.ub.uni-heidelberg.de/volltextserver/2015/1/Zusammen.pdf, Apr. 5, 2002, 4 pages, translation begins on p. 3.

Wang et al., "Generation and Identification of Monoclonal Antibodies Against FNIII Domain D of Human Tenascin-C", Hybridoma, Feb. 1, 2010, pp. 13-16, vol. 29, No. 1, Mary Ann Liebert, Inc., New Rochelle, NY.

Cunliffe et al., "Expression of Antimicrobial Neutrophil Defensins in Epithelial Cells of Active Inflammatory Bowel Disease Mucosa", Journal of Clinical Pathology, Apr. 1, 2002, pp. 298-304, vol. 55. No. 4, The Association of Clinical Pathologists, Chicago, IL.

Dumoulin et al., "Single-domain antibody fragments with high conformational stability", Protein Science, Mar. 1, 2002, pp. 500-515, vol. 11. No. 3, Wilely, Hoboken, NJ.

(Continued)

*Primary Examiner* — Maher M Haddad
(74) *Attorney, Agent, or Firm* — Pamela J. Sherwood; Bozicevic, Field & Francis LLP

(57) ABSTRACT

The invention relates to the diagnosis and treatment of diseases, including inflammatory disorders, proliferative disorders and autoimmune diseases. The invention provides, and involves the use of, antibody molecules that bind: i) lysozyme, ii) neutrophil elastase, iii) tissue inhibitor of metalloproteinase-1 (TIMP-1), or iv) the D domain of Tenascin-C. The invention also relates to the use of antibody molecules that bind v) the IIICS isoform of fibronectin, vi) the Extra Domain-B (ED-B) of fibronectin, vii) matrix-metalloproteinase 3 (MMP3), or viii) the A1 domain of tenascin-C in the diagnosis and treatment of inflammatory disorders such as inflammatory bowel disease.

7 Claims, 27 Drawing Sheets
Specification includes a Sequence Listing.

(56) References Cited

OTHER PUBLICATIONS

Giblin et al., "Tenascin-C: Form versus function", Cell Adhesion & Migration, Jan.-Apr. 2015, pp. 48-82, 9:1-2, 4, Taylor & Francis Group, Abingdon, United Kingdom.
Murphy-Ullrich et al., "Focal Adhesion Integrity Is Downregulated by the Alternatively Spliced Domain of HumanTenascin", The Journal of Cell Biology, Nov. 15, 1991, pp. 1127-1136, vol. 115, No. 4, The Rockefeller University Press, New York, NY.
Zalutsky et al., "Chimeric Anti-Tenascin Antibody 8106: Increased Tumor Localization Compared with Its Murine Parent", Nuclear Medicine & Biology, May 1996, pp. 449-458, vol. 23, Issue 4, Elsevier, New York City, NY.

* cited by examiner

ANTIBODIES FOR TREATMENT AND DIAGNOSIS OF INFLAMMATORY BOWEL DISEASE

FIELD OF THE INVENTION

The present invention relates to the diagnosis and treatment of diseases, in particular inflammatory disorders and autoimmune diseases, such as inflammatory bowel disease (IBD). In this context, the invention provides, and involves the use of, antibody molecules that bind: i) lysozyme, ii) neutrophil elastase, (iii) tissue inhibitor of metalloproteinase-1 (TIMP-1), or (iv) the D domain of tenascin-C. The invention also relates to the use of antibody molecules that bind (v) the IIICS isoform of fibronectin, (vi) the Extra Domain-B (ED-B) of fibronectin, (vii) matrix-metalloproteinase 3 (MMP3), or (viii) the A1 domain of tenascin-C in the diagnosis and treatment of IBD.

BACKGROUND TO THE INVENTION

Most conventional pharmaceuticals currently in use for the treatment of serious disorders such as cancer and inflammatory diseases do not selectively accumulate at the site of disease [Bosslet et al., 58, 1195-1201 Cancer Res. (1998)]. For example, intravenously administered drugs distribute evenly within the different organs and tissues of the body, rather than selectively accumulating at the site of disease.

One approach to circumvent the disadvantages of conventional pharmacological therapies involves the preferential delivery of a bioactive agent to the site of disease by means of a binding molecule specific for a pathology-associated marker [Neri & Bicknell (2005) Nature Rev. Cancer, 4, 436-446]. The selective targeting of the drug to the diseased tissue will ultimately result in an increased local concentration at its site of action, sparing normal organs from the unwanted effects of the bioactive agent used to confer a pharmacological benefit (e.g., a growth factor, an enzyme, a hormone, an anti-inflammatory drug, a cytotoxic drug, a cytokine, a radionuclide, or a photosensitizer). In most cases, this will lead to an improved therapeutic index of the delivered pharmaceutical, i.e. a higher efficacy with minimized side effects. Indeed, the favourable toxicity profile of site-specific therapeutics may open new avenues in the therapy of angiogenesis-related diseases, allowing the systemic administration of highly potent and promising agents, which are currently either given at suboptimal doses or whose clinical application has to date been impeded by unacceptable side-effects when applied in an unmodified form.

Ligand-based pharmacodelivery strategies fundamentally rely on the identification of good-quality markers of pathology, allowing a clear-cut discrimination between diseased tissues and healthy organs. Monoclonal antibodies and their fragments represent the preferred agents for pharmacodelivery applications [Rybak et al. 2, 22-40 Chem. Med. Chem (2007); Shrama et al., 5, 147-159 Nat. Rev. Drug Discovery (2006)], but globular protein mutants [Binz and Plückthun, 23, 1257-1268 Nature Biotechnology (2005)], peptides [Sergeeva et al., 58, 1622-1654, Adv. Drug. Deliv. Rev. (2006)] and even small organic ligands [Low et al., 41, 120-129, Acc. Chem. Res. (2008)] are also increasingly being used.

Antibody-based targeted delivery of bioactive agents to sites of angiogenesis as a therapeutic strategy for cancer treatment has been described. In the case of inflammatory disorders, antibody-based targeted delivery is much less well studied. The applicant has previously demonstrated that the ED-A domain of fibronectin, is expressed in Inflammatory Bowel Disease. Using both radioactive and fluorescent techniques, the human monoclonal antibody F8, specific to ED-A, was found to selectively localize at sites of inflammation in vivo, following intravenous administration (WO2014/055073).

However, there remains a need in the art for further antibodies which can be employed in ligand-based pharmacodelivery applications for the treatment and diagnosis of inflammatory disorders and autoimmune diseases, such as IBD.

Lysozyme

Lysozyme, is a glycoside hydrolase enzyme that damages bacterial cell walls by catalysing hydrolysis of 1,4-beta-linkages between N-acetylmuramic acid and N-acetyl-D-glucosamine residues in a peptidoglycan and between N-acetyl-D-glucosamine residues in chitodextrins. Lysozyme is known to be expressed by the epithelial cells of in the mucosa of active IBD [Klockars et al., 18, 377-341, Gut (1977), Montero et al., 190, 127-142, Anat Rec. (1978), Cunliffe et al., 55, 298-304, J Clin Pathol (2002) Rubio C A, 3,73-92, Pathogens (2014)].

Neutrophil Elastase

Neutrophil elastase is a serine proteinase secreted by neutrophils and macrophages during inflammation. As with other serine proteinases it contains a charge relay system composed of the catalytic triad of histidine, aspartate and serine residues that are dispersed throughout the primary sequence of the polypeptide but that are brought together in the three dimension conformation of the folded protein.

It has been reported that neutrophil elastase activity is elevated in both colonic mucosa and blood in inflammatory bowel disease (IBD) patients, and that it can act as an aggravating factor in IBD. [Gouni-Berthold et al., 46, 2315-2320, Hepatogastroenterol (1999), Shioya et al., 60, 14-21 Fukushima J Med Sci (2014)]. It is also a marker capable of differentiating active inflammatory bowel disease from inactive inflammatory bowel disease and irritable bowel syndrome (IBS) [Langhorst et al., 103, 162-169, Am J Gastroenterol (2008)].

Tissue Inhibitor of Metalloproteinase-1 (TIMP-1)

Tissue inhibitor of metalloproteinase-1 (TIMP-1) is a glycoprotein that inhibits the matrix metalloproteinases (MMPs), a group of peptidases involved in the degradation of the extracellular matrix. In addition to its inhibitory role against most of the known MMPs, the encoded protein is able to promote cell proliferation in a wide range of cell types, and may also have an anti-apoptotic function.

Serum concentrations of TIMP-1 have been shown to be significantly increased in patients with ulcerative colitis and Crohn's Disease compared with controls [Lacatos et al., 30, 289-295, Dig Dis (2012)].

IIICS Isoform of Fibronectin

Fibronectins (FN) are multifunctional, high molecular weight glycoprotein constituents of both the extracellular matrix and body fluids. They are involved in many different biological processes such as the establishment and maintenance of normal cell morphology, cell migration, haemostasis and thrombosis, wound healing and oncogenic transformation [Alitalo et al., (1982) Adv Cancer Res, 37 111-158; Yamada, (1983) Curr Opin Cell Biol, 1, 956-963; Hynes, (1985) Annu Rev Cell Biol, 1, 67-90; Ruoslahti et al., (1988) Annu Rev Biochem, 57, 375-413; Owens et al., (1986) Oxf Sury Eukaryot Gene, 3, 141-160]. Structural diversity in FNs is brought about by alternative splicing of three regions (ED-A, ED-B and IIICS) of the primary FN transcript (Hynes, R., (1985) Annu Rev Cell Biol, 1, 67-90;

Zardi et al., (1987) EMBO J, 6, 2337-2342) to generate at least 20 different isoforms, some of which are differentially expressed in tumour and normal tissue. For example, five different splice isoforms of the human IIICS isoform of fibronectin have been described. As well as being regulated in a tissue- and developmentally specific manner, it is known that the splicing pattern of FN-pre-mRNA is deregulated in transformed cells and in malignancies (Castellani et al., et al., (1986) J Cell Biol, 103, 1671-1677; Borsi et al., (1987) J Cell Biol, 104, 595-600; Vartio et al., (1987) J Cell Sci 88, 419-430, Zardi et al., (1987) EMBO J, 6, 2337-2342; Barone et al., (1989) EMBO J, 8, 1079-1085; Carnemolla et al., (1989) FEBS Letter 215, 269-273; Oyama et al., (1989) Biochemistry, 28, 1428-1433; Borsi et al., (1992) Exp Cell Res 199, 98-105). The FN isoforms containing the ED-A, ED-B and IIICS sequences have been shown to be expressed to a greater extent in transformed and malignant tumour cells than in normal cells.

Much of the information relating to the expression of the IIICS isoform of fibronectin in healthy and diseased tissues derives either from mRNA studies or from studies with monoclonal antibodies (antibodies FDC-6 and X18A4). These antibodies were generated by hybridoma technology following immunization with fibronectin and immunosuppression with cyclophosphamide. Antibody FDC-6 binds to a specific O-linked N-acetygalactosaminylated hexapeptide epitope within the fibronectin type III connecting segment (IIICS) [Matsuura et al., (1985) PNAS, 82, 6517-6521; Matsuura et al., (1988) J Biol Chem, 263, 3314-3322]. However, since the antibody requires both the peptide backbone and the carbohydrate moiety to recognize the epitope, it is not suitable for targeting application especially when cross-reactivity between species is needed. Antibody X18A4 recognizes a different IIICS region than FDC-6, but the binding epitope has never been fully characterized [Feinberg R. et al., (1995) Am J Obstet Gynecol, 172, 1526-1536]: the main application for antibody X18A4 is related to the detection of oncofetal fibronectin in the cervix of pregnant women to predict preterm labour. There is evidence that IIICS expression is modulated in rheumatoid arthritis and osteoarthritis: in particular, it seems that the isoform 89V (CS1) is up-regulated in inflammation [Kriegsmann J et al., (2004) Rheumatol Int, 24, 25-33; Elices M J et al., (1994) J Clin Invest, 93, 405-416]. However, to our knowledge there is no report on the presence or role of IIICS in Inflammatory Bowel Disease.

ED-B Domain of Fibronectin

Fibronectin is a large glycoprotein that is present in large amounts in plasma and tissues. ED-B is a 91-amino-acid type III homology domain that becomes inserted into the fibronectin molecule under tissue-remodeling conditions by a mechanism of alternative splicing at the level of the primary transcript. The ED-B sequence is identical in mouse, rat, rabbit, dog, monkey and man and ED-B is essentially undetectable in healthy adult individuals with the exception of some vessels in the ovaries and the endometrium during the proliferative phase, when physiological angiogenesis is occurring.

However, ED-B-containing fibronectin has been shown to be abundant in many aggressive solid tumours, and displays either predominantly vascular or diffuse stromal patterns of expression, depending on the tumour. The presence of ED-B has also been reported in ocular angiogenesis [Birchler M et al., (1999) Nature Biotech, 17, 984-988, Nicolò M et al (2003) Am J Ophtalmol, 135, 7-13], rheumatoid arthritis (WO2007/128563), endometriosis [Schwager C et al., (2011) Hum Reprod, 26, 2344-2352, WO2010/078950] and atherosclerotic plaques [Matter C M et al., (2004) Circ Res, 95, 1225-1233, Pedretti M et al (2010) Atherosclerosis, 208, 382-389]. The applicant of the present application, has previously shown that the ED-B of fibronectin scored negative when probed with the anti ED-B antibody L19, in specimens of ulcerative colitis (WO2010/078950)

Matrix-Metalloproteinase 3 (MMP3)

Matrix metalloproteinase 3 (also known as stromelysin 1) is a member of a family of more than 20 zinc-dependent extracellular enzymes with a key role in tissue remodeling [Nagase 30 and Woessner, (1999) J Biol Chem, 274, 21491-21494; Martin and Matrisian, (2007) Cancer Metastasis Rev, 26, 717-724; Vartak and Gemeinhart, (2007) J Drug Target 15(1) 1-20].

Abnormal expression of various MMP proteins has been shown to play a role in a variety of disease types including cancer progression and in inflammatory conditions such as rheumatoid arthritis [Martin and Matrisian, (2007) Cancer Metastasis Rev, 26, 717-724; Brinckerhoff and Matrisian, (2002) Nat Rev Mol Cell Biol, 3, 207-214; Overall and Kleifeld, (2006) Nat Rev Cancer, 6, 227-239]. In a Crohn's Disease genome micro-array it has been reported that the MMP3 gene is differentially expressed compared to controls [Noble et al., (2010) Inflamm Bowel Dis, 16, 1717-1728]

A1, C and D Domains of Tenascin-C

Tenascin-C is a glycoprotein of the extracellular matrix. It comprises several fibronectin type 3 homology repeats that can be either included or omitted in the primary transcript by alternative splicing, leading to small and large isoforms that have distinct biological functions. Whereas the small isoform is expressed in several tissues, the large isoform of tenascin-C exhibits a restricted pattern of expression. It is virtually undetectable in healthy adult tissues but is expressed during embryogenesis and is expressed in adult tissues undergoing tissue remodeling including neoplasia.

Traditionally, one has referred to the large isoform of tenascin-C for tenascin molecules, which would putatively comprise all alternatively spliced domains A1, A2, A3, A4, B, AD, C, D, and to the small isoform of tenascin-C whenever these domains were absent. There are several reports indicating the presence of tenascin-C in general, in the serum and in the colonic tissues of patients with IBD [Riedl et al., 16, 285-291, Int J Colorectal Dis (2001), Geboes et al., 9, 281-286, Int J Surg Pathol (2001), Dueck et al., 82, 477-483, Int J Cancer (1999)]. However, the role of the A1 and of the D domain of Tenascin-C has not been elucidated in full and is not clear whether they can be used as a target for the pharmacodelivery of agents to treat or diagnose IBD. For example, the applicant of the present application, has previously shown that the domain A1 of Tenascin-C scored negative when probed with the anti-A1 domain antibody F16, in specimens of ulcerative colitis (WO2010/078950). Antibodies that bind to the domain D of Tenascin-C and in particular the properties of the P12 antibody for tumor targeting have been described (Brack et al., Clin. Cancer Res. (2006) 12, 3200-3208 and in WO2006/050834).

SUMMARY OF THE INVENTION

The present inventors have prepared novel antibody molecules which bind i) lysozyme, ii) neutrophil elastase, (iii) tissue inhibitor of metalloproteinase-1 (TIMP-1), or (iv) the D domain of tenascin-C.

The above antibody molecules find application in therapy and diagnosis, including pharmacodelivery applications. In particular, the antibody molecules of the invention will find application in the treatment and diagnosis of inflammatory disorders and autoimmune diseases.

In addition, the present inventors have shown for the first time that antibody molecules which bind (i) the IIICS isoform of fibronectin (ii) the ED-B of fibronectin (iii) the A1 domain of Tenascin-C, (iv) the D domain of Tenascin C, or (v) MMP3 are capable of targeting vascular structures associated with ulcerative colitis. This targeting is not displayed by antibody molecules which bind the C domain of Tenascin C. Such antibody molecules thus find application in the treatment and diagnosis of IBD, including ulcerative colitis and Crohn's disease. These results were unexpected as, for example, the ED-B of fibronectin and the A1 domain of tenascin-C had been previously shown by the applicant not to be expressed in ulcerative colitis (WO2010/078950). It is possible that these earlier false negative results may have been the result of degradation of the frozen ulcerative colitis samples, as the ulcerative colitis specimens analysed in WO2010/078950 were stored for long periods at −80° C.

In a first aspect, the present invention relates to an antibody molecule that binds lysozyme, preferably human lysozyme. The antibody molecule preferably comprises the VH domain complementary determining region 3 (HCDR3) of the CT01 antibody molecule set forth in SEQ ID NO: 5 or an HCDR3 with the amino acid sequence set forth in SEQ ID NO: 5 with three or fewer amino acid substitutions, deletions, or insertions. In addition, the antibody molecule may comprise the HCDR1, HCDR2, LCDR1, LCDR2, and/or LCDR3 sequences of the CT01 antibody molecule set forth in SEQ ID NOs 3-4 and 6-8, respectively. In one example, the antibody molecule may comprise the VH domain and/or VL domain of the CT01 antibody molecule set forth in SEQ ID Nos 1 and 2, respectively. Alternatively, the antibody molecule may comprise the VH domain and/or VL domain of the CT01 antibody molecule set forth in SEQ ID Nos 69 and 2, respectively.

In a second aspect, the present invention relates to an antibody molecule that binds neutrophil elastase, preferably human neutrophil elastase (HNE). Preferably, the antibody molecule comprises the HCDR3 of the FF02 antibody molecule set forth in SEQ ID NO: 78, or an HCDR3 with the amino acid sequence set forth in SEQ ID NO: 78 with three or fewer amino acid substitutions, deletions, or insertions. In addition, the antibody molecule may comprise the HCDR1, HCDR2, LCDR1, LCDR2, and/or LCDR3 sequences of the FF02 antibody molecule set forth in SEQ ID Nos 76-77 and 79-81, respectively. The antibody molecule may comprise the VH domain and/or VL domain of the FF02 antibody molecule set forth in SEQ ID Nos 74 and 75, respectively.

Alternatively, the antibody molecule that binds neutrophil elastase may comprise the HCDR3 of the FF01 antibody molecule set forth in SEQ ID NO: 13, or an HCDR3 with the amino acid sequence set forth in SEQ ID NO: 13 with three or fewer amino acid substitutions, deletions, or insertions. In addition, the antibody molecule may comprise the HCDR1, HCDR2, LCDR1, LCDR2, and/or LCDR3 sequences of the FF01 antibody molecule set forth in SEQ ID Nos 11-12 and 14-16, respectively. Alternatively, the antibody molecule may comprise the HCDR1, HCDR2, LCDR1, LCDR2, and/or LCDR3 sequences of the FF01 antibody molecule set forth in SEQ ID Nos 11 and 86, and 14-16, respectively. In one example, the antibody molecule may comprise the VH domain and/or VL domain of the FF01 antibody molecule set forth in SEQ ID Nos 9 and 10, respectively. Alternatively, the antibody molecule may comprise the VH domain and/or VL domain of the FF01 antibody molecule set forth in SEQ ID Nos 70 and 10, respectively. As a further alternative, the antibody molecule may comprise the VH domain and/or VL domain of the FF01 antibody molecule set forth in SEQ ID Nos 9 and 85, respectively. As a yet further alternative, the antibody molecule may comprise the VH domain and/or VL domain of the FF01 antibody molecule set forth in SEQ ID Nos 70 and 85, respectively.

In a third aspect, the present invention relates to an antibody molecule that binds tissue inhibitor of metalloproteinase-1 (TIMP-1). The Tissue Inhibitor of Metalloproteinase-1 is preferably human Tissue Inhibitor of Metalloproteinase-1. The antibody molecule may comprise the HCDR3 of the 2PC10 antibody molecule set forth in SEQ ID NO: 21, or an HCDR3 with the amino acid sequence set forth in SEQ ID NO: 21 with three or fewer amino acid substitutions, deletions, or insertions. In addition, the antibody molecule may comprise the HCDR1, HCDR2, LCDR1, LCDR2, and/or LCDR3 sequences of the 2PC10 antibody molecule set forth in SEQ ID Nos 19-20 and 22-24, respectively. In one example, the antibody molecule may comprise the VH domain and/or VL domain of the 2PC10 antibody molecule set forth in SEQ ID Nos 17 and 18, respectively. Alternatively, the antibody molecule may comprise the VH domain and/or VL domain of the 2PC10 antibody molecule set forth in SEQ ID Nos 71 and 18, respectively In a fourth aspect, the present invention relates to an antibody molecule that binds the D domain of tenascin-C. The D domain of tenascin-C is preferably the D domain of human tenascin C. The antibody molecule preferably comprises the HCDR3 of the CPR01 antibody molecule set forth in SEQ ID NO: 29, or an HCDR3 with the amino acid sequence set forth in SEQ ID NO: 29 with three or fewer amino acid substitutions, deletions, or insertions. In addition, the antibody molecule may comprise the HCDR1, HCDR2, LCDR1, LCDR2, and/or LCDR3 sequences of the CPR01 antibody molecule set forth in SEQ ID Nos 27-28 and 30-32, respectively. In one example, the antibody molecule may comprise the VH domain and/or VL domain of the CPR01 antibody molecule set forth in SEQ ID Nos 25 and 26, respectively. Alternatively, the antibody molecule may comprise the VH domain and/or VL domain of the CPR01 antibody molecule set forth in SEQ ID Nos 72 and 26, respectively. As a further alternative, the antibody molecule may comprise the VH domain and/or VL domain of the CPR01 antibody molecule set forth in SEQ ID Nos 25 and 87, respectively. As a yet further alternative, the antibody molecule may comprise the VH domain and/or VL domain of the CPR01 antibody molecule set forth in SEQ ID Nos 72 and 87, respectively.

Alternatively, the antibody molecule that binds the D domain of tenascin-C may be an analogue of CPR01 termed CPR01.1 which comprises the same HCDR1, HCDR3, LCDR1, LCDR2 of CPR01 and a HCDR2 with the amino acid sequence of SEQ. ID NO: 91 and a LCDR3 with the amino acid sequence of SEQ. ID. NO: 92. The antibody molecule CPR01.1 that binds the D domain of tenascin-C may comprises the HCDR3 of the CPR01.1 antibody molecule set forth in SEQ ID NO: 29, or an HCDR3 with the amino acid sequence set forth in SEQ ID NO: 29 with three, two or fewer amino acid substitutions, deletions, or insertions. In addition, the antibody molecule may comprise the HCDR1 sequence of the CPR01.1 antibody molecule set forth in SEQ ID NO: 27, the HCDR2 sequence of the CPR01.1 antibody molecule set forth in SEQ ID NO: 91, the LCDR1 sequence of the CPR01.1 antibody molecule set forth in SEQ ID NO: 30, the LCDR2 sequence of the CPR01.1 antibody molecule set forth in SEQ ID NO: 31, and/or the LCDR3 sequence of the CPR01.1 antibody molecule set forth in SEQ ID NO: 92. In one example, the antibody molecule may comprise the VH domain and/or VL domain of the CPR01.1 antibody molecule set forth in SEQ ID Nos 89 and 90, respectively. The amino acid sequence of the full-length CPR01.1 scFv is set forth in SEQ ID NO: 93. Thus, the antibody molecule, or fragment thereof, preferably comprises, or has, the amino acid sequence set forth in SEQ ID NO: 93, or the sequence set forth in SEQ ID NO: 93 with twenty or fewer amino acid substitutions, deletions, or insertions, more preferably with 8 amino acid substitutions. In some embodiments, a CPR01.1 antibody molecule may comprise an amino acid sequence of approximately 96% sequence identity to CRP01.

In addition, the present inventors have also shown that the antibody molecules which bind the D domain of Tenascin C are capable of targeting vascular structures associated with a proliferative disorder such as cancer. Such antibody molecules thus find application in the treatment and diagnosis of a proliferative disorder such as cancer.

As mentioned herein, an antibody molecule of the invention, or for use in the invention, may comprise a HCDR3 sequence as described herein with three or fewer amino acid substitutions, deletions, or insertions. For example, an antibody molecule of the invention, or for use in the invention, may comprise a HCDR3 sequence as described herein with two or fewer, or one, amino acid substitution(s), deletion(s), or insertion(s). As with regard to the HCDR3 sequences, an antibody molecule of the invention, or for use in the invention, may comprise a HCDR1, HCDR2, LCDR1, LCDR2, and/or LCDR3 sequence, as described herein, with three or fewer, two or fewer, or one, amino acid substitution(s), deletion(s), or insertion(s). Similarly, and antibody molecule of the invention, or for use in the invention, may comprise a VH and/or VL domain sequence as described herein with ten or fewer, e.g. nine or fewer, eight or fewer, seven or fewer, six or fewer, five or fewer, four or fewer, three or fewer, two or fewer, or one, amino acid substitution(s), deletion(s), or insertion(s). Where the VH and/or VL domain are concerned, the amino acid substitution(s), deletion(s), or insertion(s) may be in VH and/or VL domain framework regions.

Where the present application discloses that an antibody HCDR1, HCDR2, HCDR3, LCDR1, LCDR2, LCDR3, VH or VL sequence has a particular sequence, this may refer to the HCDR1, HCDR2, HCDR3, LCDR1, LCDR2, LCDR3, VH or VL comprising, or consisting of, the recited sequence.

In addition to the novel antibodies described above, other antibodies previously generated by the current applicant that bind the IIICS isoform of fibronectin, the ED-B of fibronectin, the A1 domain of tenascin-C, or MMP-3 have been shown to be suitable for targeting neovascular structures associated with IBD, in particular neovascular structures associated with ulcerative colitis, although it is expected that the neovascular structures of other examples of inflammatory bowel disease, such as Crohn's disease, can equally be targeted using the antibodies described herein.

Thus, in a fifth aspect, the present invention relates to an antibody molecule that binds the IIICS isoform of fibronectin, the ED-B of fibronectin, the A1 domain of tenascin-C, the D domain of tenascin-C, or MMP-3 for use in a method of treating inflammatory bowel disease, wherein the antibody molecule is conjugated to an immunosuppressive or anti-inflammatory agent. A method of treating an inflammatory bowel disease in a patient comprising administering a therapeutically effective amount of a medicament comprising an antibody molecule which binds the IIICS isoform of fibronectin, the ED-B of fibronectin, the A1 domain of tenascin-C, the D domain of tenascin-C, or MMP-3, wherein the antibody molecule is conjugated to an immunosuppressive or anti-inflammatory agent, similarly forms part of the present invention. The use of an antibody molecule that binds the IIICS isoform of fibronectin, the ED-B of fibronectin, the A1 domain of tenascin-C, the D domain of tenascin-C, or MMP-3 for the manufacture of a medicament for the treatment of inflammatory bowel disease also forms part of the present invention.

In addition, the present invention relates to an antibody molecule that binds the IIICS isoform of fibronectin, the ED-B of fibronectin, the A1 domain of tenascin-C, the D domain of tenascin-C, or MMP-3 for use in a method of imaging, detecting, or diagnosing inflammatory bowel disease, wherein the antibody molecule is optionally conjugated to a detectable label. A method of imaging, detecting, or diagnosing an inflammatory bowel disease in a patient comprising administering an antibody molecule which binds the IIICS isoform of fibronectin, the ED-B of fibronectin, the A1 domain of tenascin-C, the D domain of tenascin-C, or MMP-3 to the patient, wherein the antibody molecule is optionally conjugated to a detectable label. The use of an antibody molecule that binds the IIICS isoform of fibronectin, the ED-B of fibronectin, the A1 domain of tenascin-C, the D domain of tenascin-C, or MMP-3 for the manufacture of a diagnostic product for the imaging, detection, or diagnosis of inflammatory bowel disease also forms part of the present invention. The antibody molecule may again be conjugated to a detectable label.

In the context of the present invention, the IIICS isoform of fibronectin, the ED-B of fibronectin, the A1 domain of tenascin-C, the D domain of tenascin-C and MMP-3, are preferably the IIICS isoform of human fibronectin, the ED-B of human fibronectin, the A1 domain of human tenascin-C, the D domain of human tenascin-C, or human MMP-3.

The anti-IIICS antibody SW01 and anti-MMP3 CH01 antibodies were first disclosed in PCT/EP2015/067309. The anti-EDB antibody L19 is disclosed in WO2013/045125, for example. The anti-domain A1 of tenascin C antibody F16 is disclosed in WO2011/001276. The anti-domain C of tenascin C antibody G11 disclosed in WO2006/050834. The anti-hen egg lysozyme (HEL) antibody KSF used as control in the examples reported herein is disclosed in Frey et al., 3, 468-478, Integr Biol (2011).

Thus, an antibody molecule that binds the IIICS isoform of fibronectin for use in the present invention may comprise the HCDR3 of antibody molecule SW01 set forth in SEQ ID NO: 37, or an HCDR3 with the amino acid sequence set forth in SEQ ID NO: 37 with three or fewer amino acid substitutions, deletions, or insertions. In addition, the antibody molecule may comprise the HCDR1, HCDR2, LCDR1, LCDR2, and/or LCDR3 sequences of the SW01 antibody molecule set forth in SEQ ID NOs 35-36 and 38-40, respectively. For example, the antibody molecule may comprise the VH domain and/or VL domain of the SW01 antibody molecule set forth in SEQ ID NOs 33 and 34, respectively. Alternatively, the antibody molecule may comprise the VH domain and/or VL domain of the SW01 antibody molecule set forth in SEQ ID NOs 33 and 73, respectively.

Similarly, an antibody molecule that binds MMP3 for use in the present invention may comprise the HCDR3 of antibody molecule CH01 set forth in SEQ ID NO: 45, or an HCDR3 with the amino acid sequence set forth in SEQ ID NO: 45 with three or fewer amino acid substitutions, deletions, or insertions. In addition, the antibody molecule may comprise the HCDR1, HCDR2, LCDR1, LCDR2, and/or LCDR3 sequences of the CH01 antibody molecule set forth in SEQ ID NOs 43-44 and 46-48, respectively. For example, the antibody molecule may comprise the VH domain and/or VL domain of the CH01 antibody molecule set forth in SEQ ID NOs 41 and 42, respectively.

An antibody molecule that binds the A1 domain of tenascin-C for use in the present invention may comprise the HCDR1, HCDR2, HCDR3, LCDR1, LCDR2, and/or LCDR3 sequences of the F16 antibody described herein. In one example, the antibody may comprise the VH and/or VL domain of the F16 antibody described herein. Specifically, an antibody molecule that binds the A1 domain of tenascin-C for use in the present invention may comprise the HCDR3 of antibody molecule F16 set forth in SEQ ID NO: 61, or an HCDR3 with the amino acid sequence set forth in SEQ ID NO: 61 with three or fewer amino acid substitutions, deletions, or insertions. In addition, the antibody molecule may comprise the HCDR1, HCDR2, LCDR1, LCDR2, and/or LCDR3 sequences of the F16 antibody molecule set forth in SEQ ID NOs 59-60 and 62-64, respectively. For example, the antibody molecule may comprise the VH domain and/or VL domain of the F16 antibody molecule set forth in SEQ ID NOs 57 and 58, respectively. Alternatively, the antibody molecule may comprise the VH domain and/or VL domain of the F16 antibody molecule set forth in SEQ ID NOs 57 and 88, respectively.

Similarly, an antibody molecule that binds the ED-B of fibronectin for use in the present invention may comprise the HCDR1, HCDR2, HCDR3, LCDR1, LCDR2, and/or LCDR3 sequences of the L19 antibody described herein. In one example, the antibody may comprise the VH and/or VL domain of the L19 antibody described herein. Specifically, an antibody molecule that binds the ED-B of fibronectin for use in the present invention may comprise the HCDR3 of antibody molecule L19 set forth in SEQ ID NO: 53, or an HCDR3 with the amino acid sequence set forth in SEQ ID NO: 53 with three or fewer amino acid substitutions, deletions, or insertions. In addition, the antibody molecule may comprise the HCDR1, HCDR2, LCDR1, LCDR2, and/or LCDR3 sequences of the L19 antibody molecule set forth in SEQ ID NOs 51-52 and 54-56, respectively. For example, the antibody molecule may comprise the VH domain and/or VL domain of the L19 antibody molecule set forth in SEQ ID NOs 49 and 50, respectively.

An antibody molecule, as referred to herein, may be in any suitable format. Many antibody molecule formats are known in the art and include both complete antibody molecule molecules, such as IgG, as well as antibody molecule fragments, such as a single chain Fv (scFv). The term "antibody molecule" as used herein encompasses both complete antibody molecule molecules and antibody molecule fragments, in particular antigen-binding fragments. Preferably, an antibody molecule comprises a VH domain and a VL domain. In a preferred embodiment, the antibody molecule is or comprises a scFv, is a small immunoprotein (SIP), is a diabody, or is a (complete) IgG molecule.

An antibody molecule of, or for use in, the invention preferably comprises the HCDR1, HCDR2, HCDR3, LCDR1, LCDR2, and/or LCDR3 sequences of an antibody as disclosed or described herein in a framework. The frameworks are preferably human frameworks, specifically human germline frameworks. Thus a VH and/or VL domain framework, as referred to herein, is preferably a human framework, more preferably a human germline framework. For example, the VH domain framework may be DP47 and/or the VL domain framework may be DPL16 or DPK22. The CT01, CPR01, CPR01.1, FF02 and FF01 antibodies employed in the present examples, comprised the VH domain human framework germline sequence DP47 and the VL domain human framework germline sequence DPL16, while antibody 2PC10 employed in the examples, comprised the VH domain human framework germline sequence DP47 and the VL domain human framework germline sequence DPK22.

An antibody molecule of the present invention may be conjugated to a molecule to provide a conjugate. The choice of molecule conjugated to the antibody molecule will depend on the intended application of the conjugate. For example, where the conjugate is intended for the treatment of an inflammatory disorder or autoimmune disease, the conjugate may comprise an antibody molecule of the invention, or for use in the invention, and an immunosuppressive or anti-inflammatory agent, such as a cytokine. Where the conjugate is intended for use in imaging, detecting, or diagnosing a disease or disorder, the conjugate may comprise an antibody molecule of the invention, or for use in the invention, and a detectable label, such as a radioisotope, e.g. a non-therapeutic radioisotope. Depending on the molecule conjugated to the antibody molecule, the conjugate may be or may comprise a single chain protein. When the conjugate is a single chain protein, the entire protein can be expressed as a single polypeptide or fusion protein. In this case, the molecule may be conjugated to the antibody molecule by means of a peptide linker. Fusion proteins have the advantage of being easier to produce and purify since they consist of one single species. This facilitates production of clinical-grade material. Alternatively, the molecule may be conjugated to the antibody molecule by means of a cleavable linker.

The invention also provides isolated nucleic acids encoding the antibodies and conjugates of the invention. The skilled person would have no difficulty in preparing such nucleic acids using methods well-known in the art. An isolated nucleic acid may be used to express the antibody molecule or conjugate of the invention, for example by expression in a bacterial, yeast, insect or mammalian host cell. A preferred host cell is *E. coli*. The nucleic acid will generally be provided in the form of a recombinant vector for expression. Host cells in vitro comprising such nucleic acids and vectors are part of the invention, as is their use for expressing the antibodies and conjugates of the invention, which may subsequently be purified from cell culture and optionally formulated into a pharmaceutical composition.

An antibody molecule or conjugate of the invention may be provided for example in a pharmaceutical composition, and may be employed for medical use as described herein, either alone or in combination with one or more further therapeutic agents or therapeutically acceptable excipients. Alternatively, the antibody molecule or conjugate of the invention may be provided in a diagnostic composition and may be employed for diagnostic use as described herein.

The invention also relates to an antibody molecule or conjugate of the invention for use in a method for treatment of the human or animal body by therapy. For example, an antibody molecule or conjugate of the invention may for use in a method of treating an inflammatory disorder, preferably an inflammatory bowel disorder, or autoimmune disease in a patient. The invention also relates to a method of treating an inflammatory disorder, preferably an inflammatory bowel disorder, and/or autoimmune disease in a patient, the method comprising administering a therapeutically effective amount of an antibody molecule or conjugate of the invention to the patient. The use of an antibody molecule or conjugate of the invention for the manufacture of a medicament for the treatment of an inflammatory disorder, preferably an inflammatory bowel disorder, or autoimmune disease. Some diseases can be described as both an inflammatory disorder and autoimmune disease. This includes IBD, which may preferably be treated or diagnosed with the antibodies of the invention.

The invention further relates to an antibody molecule of the invention for use in a method of delivering a molecule to sites of an inflammatory disorder, preferably sites of an inflammatory bowel disorder, or sites of autoimmune disease in a patient. The invention also relates to a method of delivering a molecule to sites of an inflammatory disorder, preferably sites of an inflammatory bowel disorder, or sites of autoimmune disease in a patient comprising administering to the patient an antibody molecule of the invention, wherein the antibody molecule is conjugated to the molecule. The use of an antibody molecule of the invention for the manufacture of a medicament for the delivery of a molecule to sites of an inflammatory disorder, preferably sites of an inflammatory bowel disorder, or sites of autoimmune disease in a patient.

The invention also relates to an antibody molecule of the invention for use in a method of imaging, detecting, or diagnosing an inflammatory disorder, preferably an inflammatory bowel disorder, or autoimmune disease in a patient, wherein the antibody molecule is optionally conjugated to a detectable label. The invention further relates to a method of imaging, detecting, or diagnosing an inflammatory disorder, preferably an inflammatory bowel disorder, or an autoimmune disease in a patient comprising administering an antibody molecule of the invention to the patient, wherein the antibody molecule is optionally conjugated to a detectable label. The use of an antibody of the invention for the manufacture of a diagnostic product for the imaging, detection, or diagnosis of inflammatory disorder, preferably an inflammatory bowel disorder, or autoimmune disease also forms part of the present invention. The antibody molecule may again be conjugated to a detectable label.

A patient, as referred to herein, is preferably a human patient.

IBD, as referred to herein, is preferably ulcerative colitis (UC) or Crohn's disease.

BRIEF DESCRIPTION OF THE FIGURES

FIG. 2 shows immunofluorescence experiments performed in sections of ulcerative colitis patients using different antibodies.

FIG. 3A demonstrates that the anti-human lysozyme antibody CT01 clearly stains HT29 cells, while FIG. 3C shows that the negative control antibody anti-egg hen lysozyme KSF does not. FIG. 3B shows the DAPI staining of the nuclei of the cells shown in FIG. 3A, while FIG. 3D shows the staining of the nuclei of the cells shown in FIG. 3C.

FIGS. 4A and 4B are for patient with colitis n° 1; FIG. 4C and 4D are for patient with colitis n° 2. FIGS. 4E and 4F are for patient with Crohn's disease n° 1 and FIGS. 4G and 4H are for patient with Crohn's disease n° 2.

DETAILED DESCRIPTION

Figure 1A:
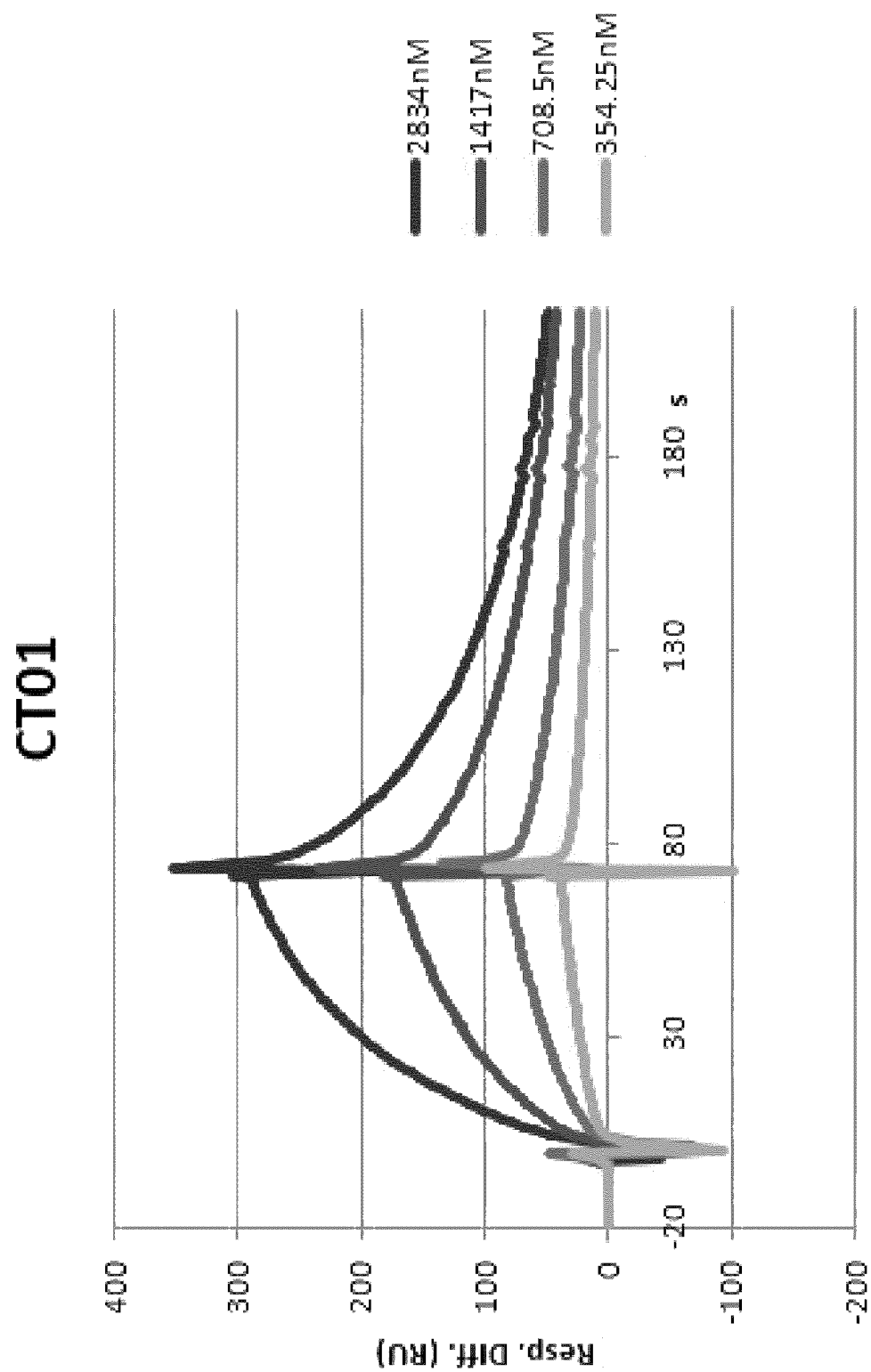
FIG. 1A shows the Biacore characterization of the antibody CT01 and confirms its binding to human lysozyme.
Figure 1B:
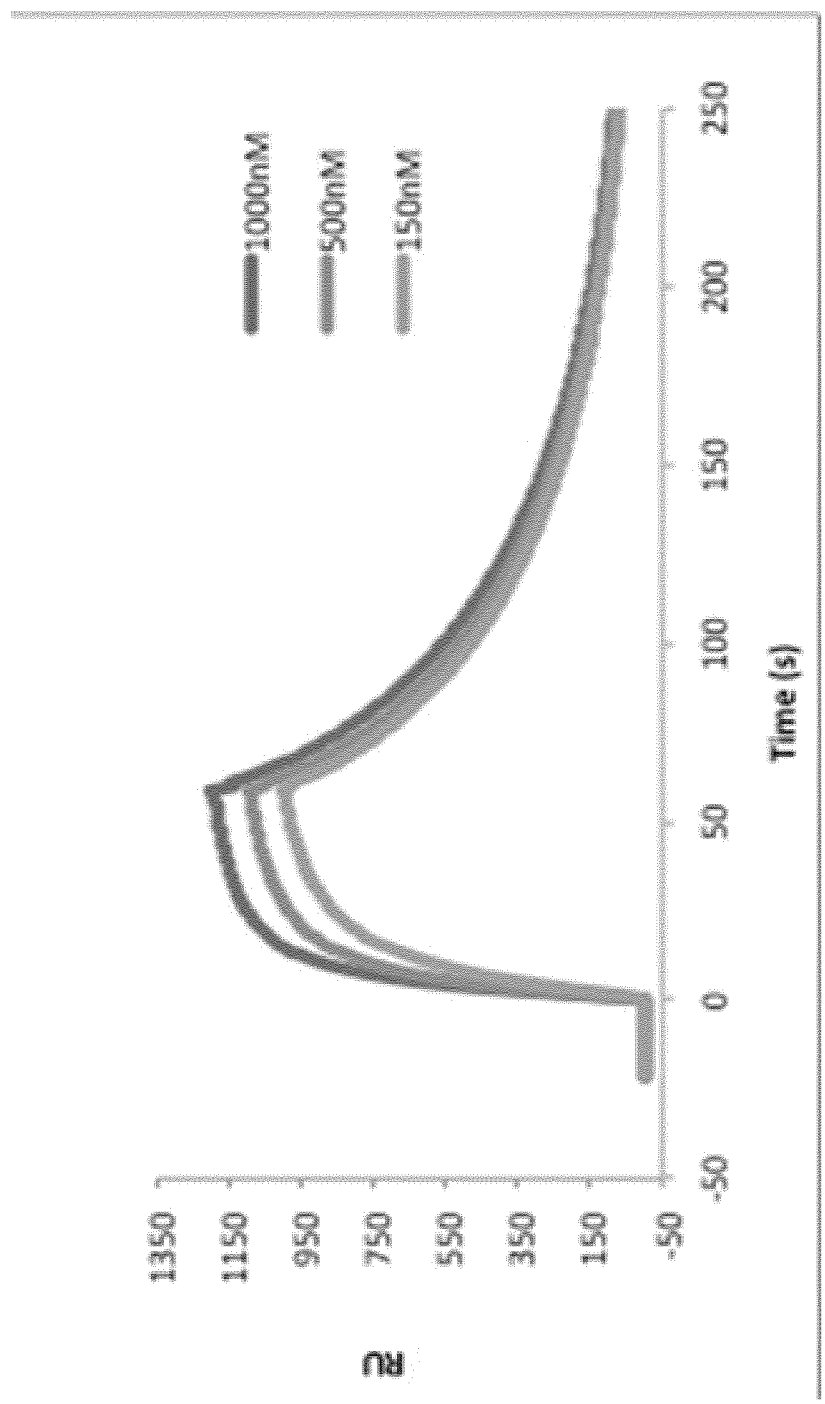
FIG. 1B shows the Biacore characterization of the antibody 2PC10 and confirms its binding to TIMP-1.
Figure 1C:
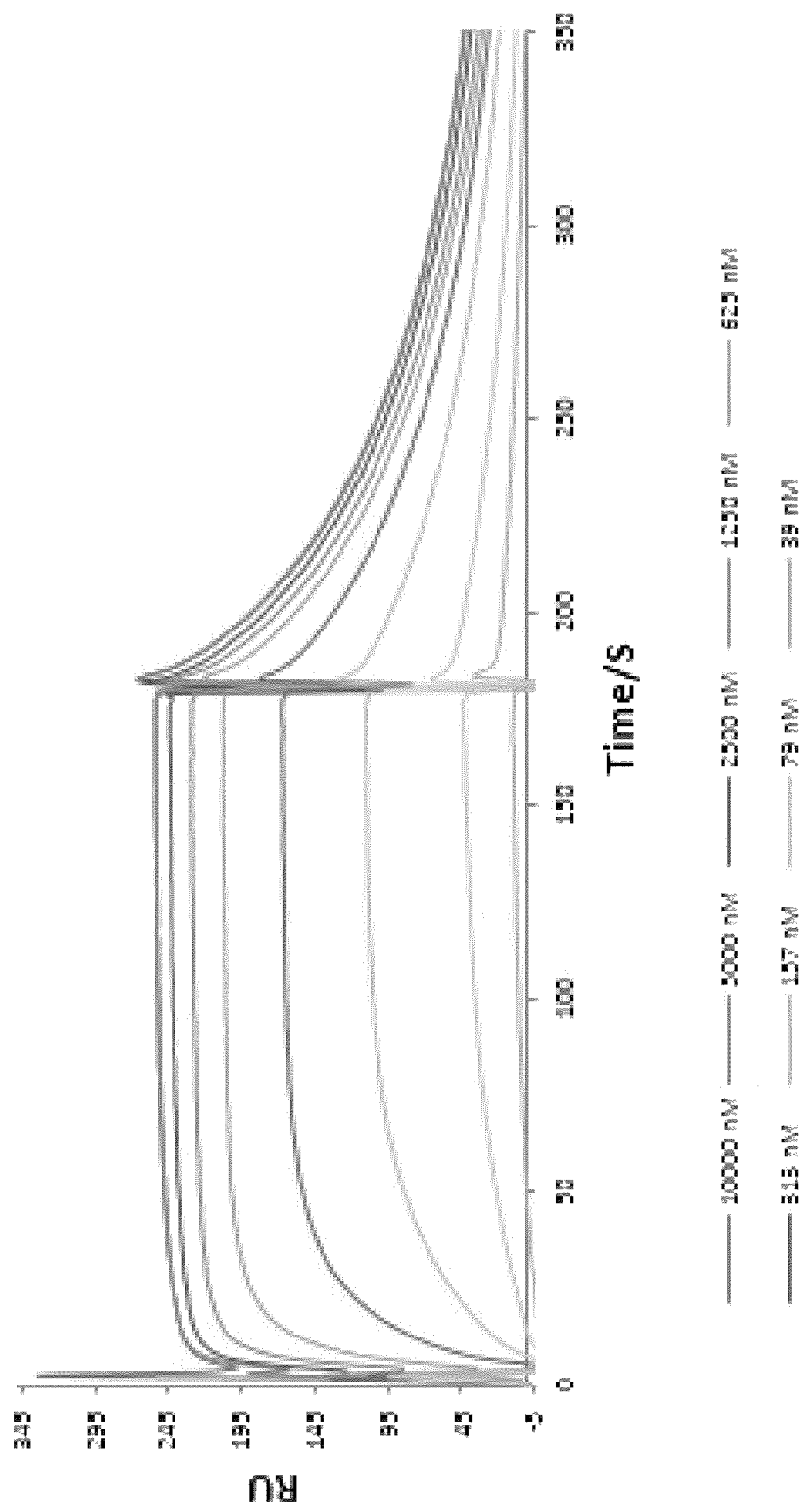
FIG. 1C shows the Biacore characterization of the antibody CPR01 and confirms its binding to the domain D of human Tenascin-C.
Figure 1D:
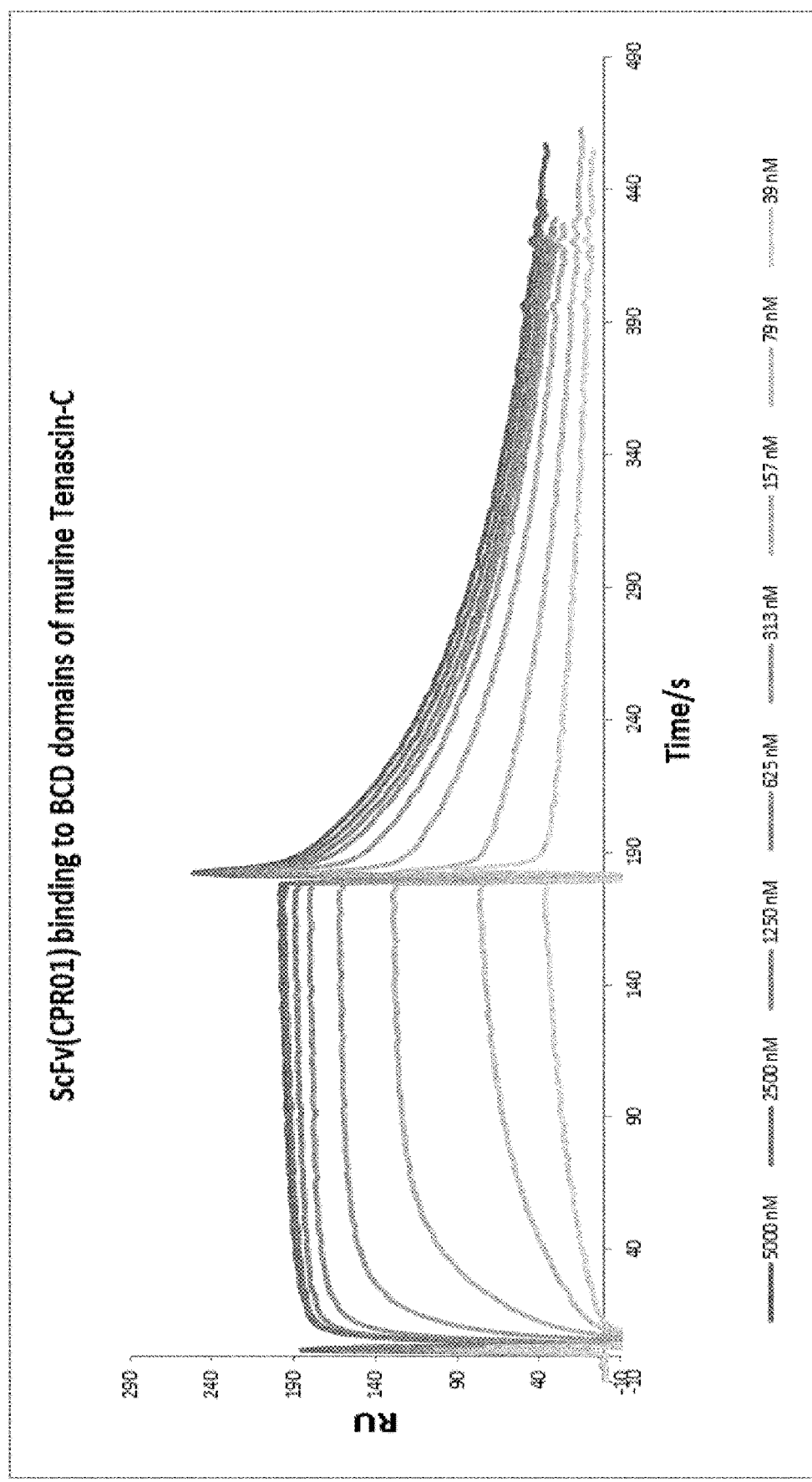
FIG. 1D shows the Biacore characterization of the antibody CPR01 and confirms its binding to the domain BCD of murine Tenascin-C.
Figure 1E:
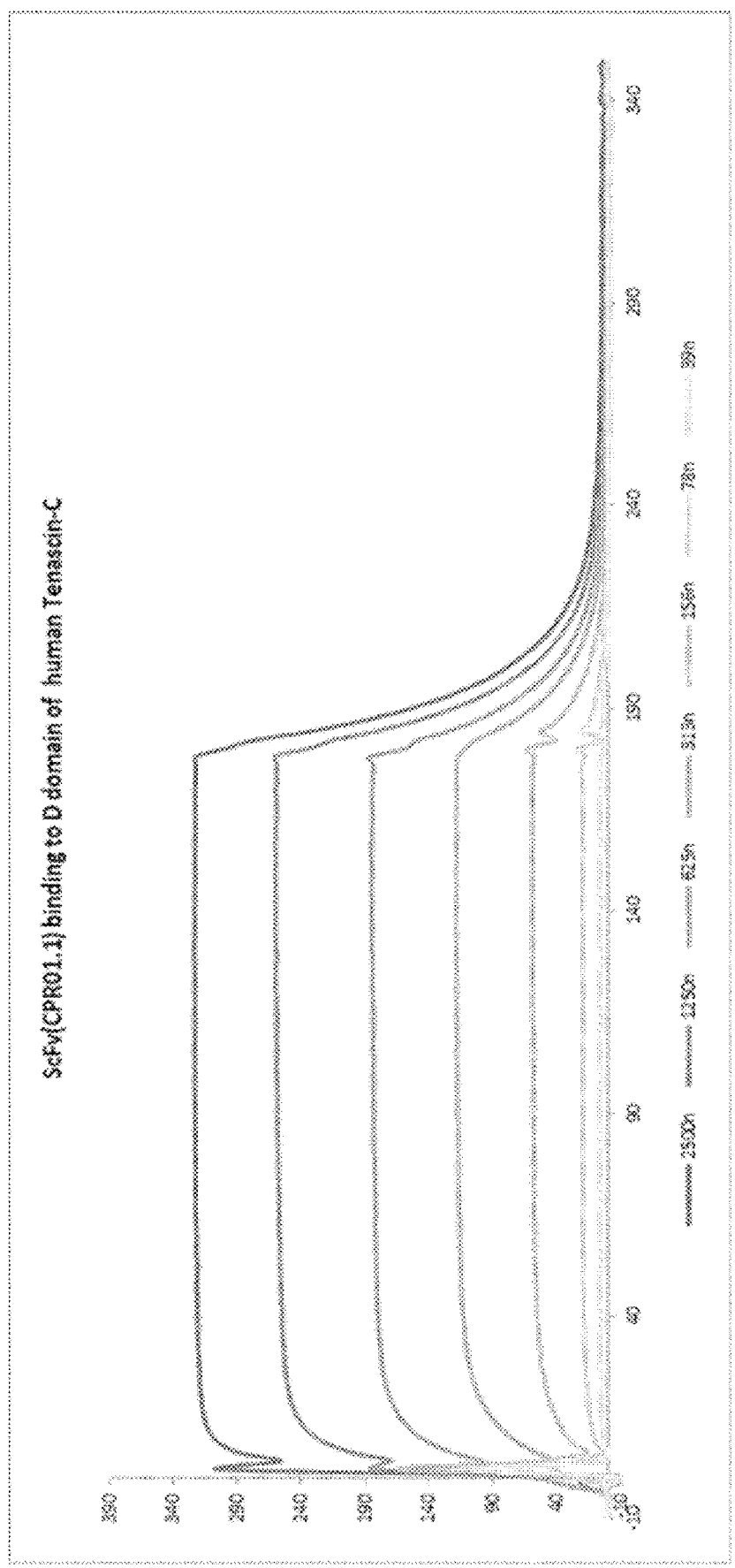
FIG. 1 E shows the Biacore characterization of the antibody CPR01.1 and confirms its binding to the domain D of human Tenascin-C.
FIG. 1F shows the Biacore characterization of the antibody CPR01.1 and confirms its binding to the domain BCD of murine Tenascin-C.
Figure 1F:
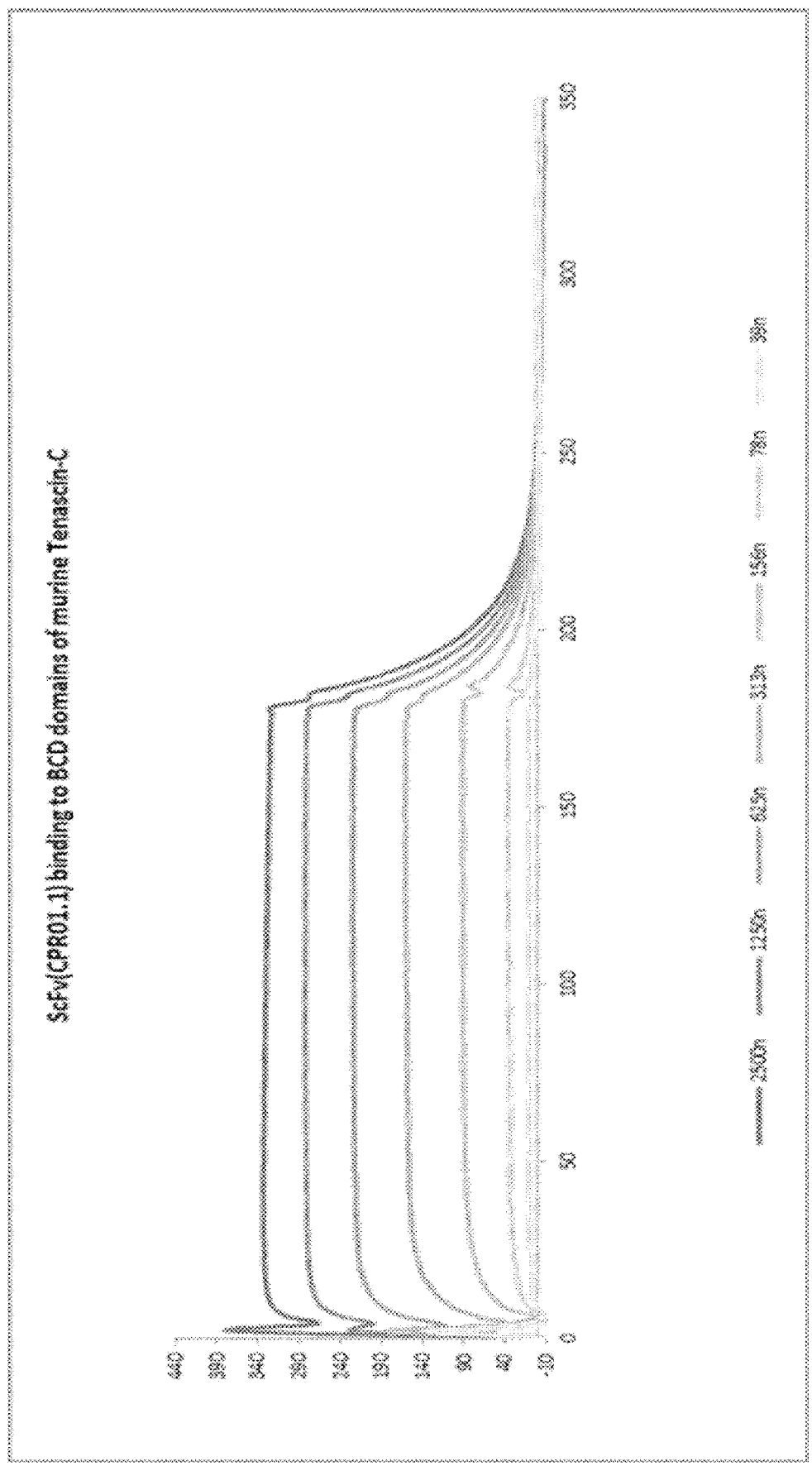
Figure 2A:
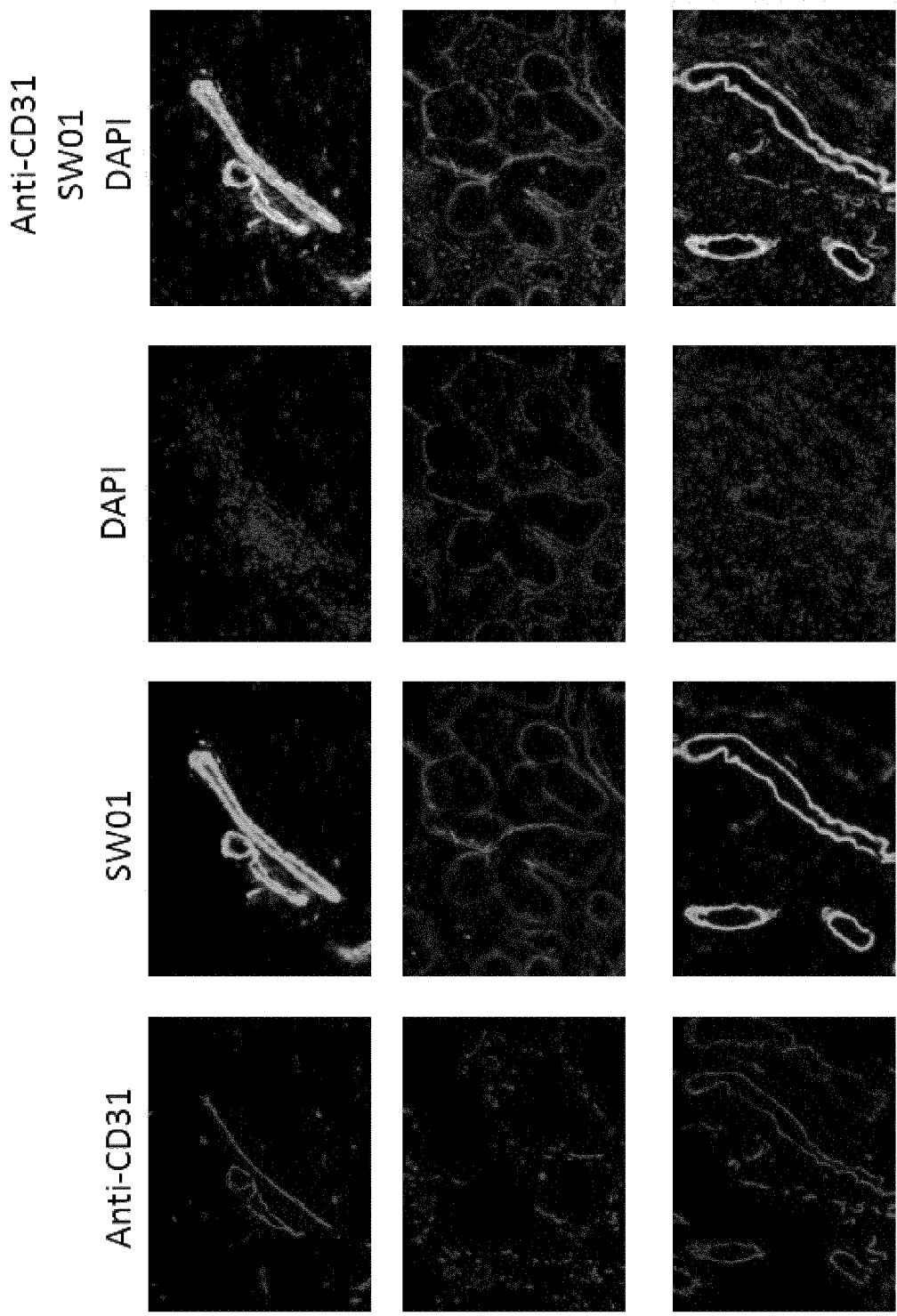
FIG. 2A shows strong positive staining of neovascular structures with the anti-IIICS antibody SW01.
Figure 2B:
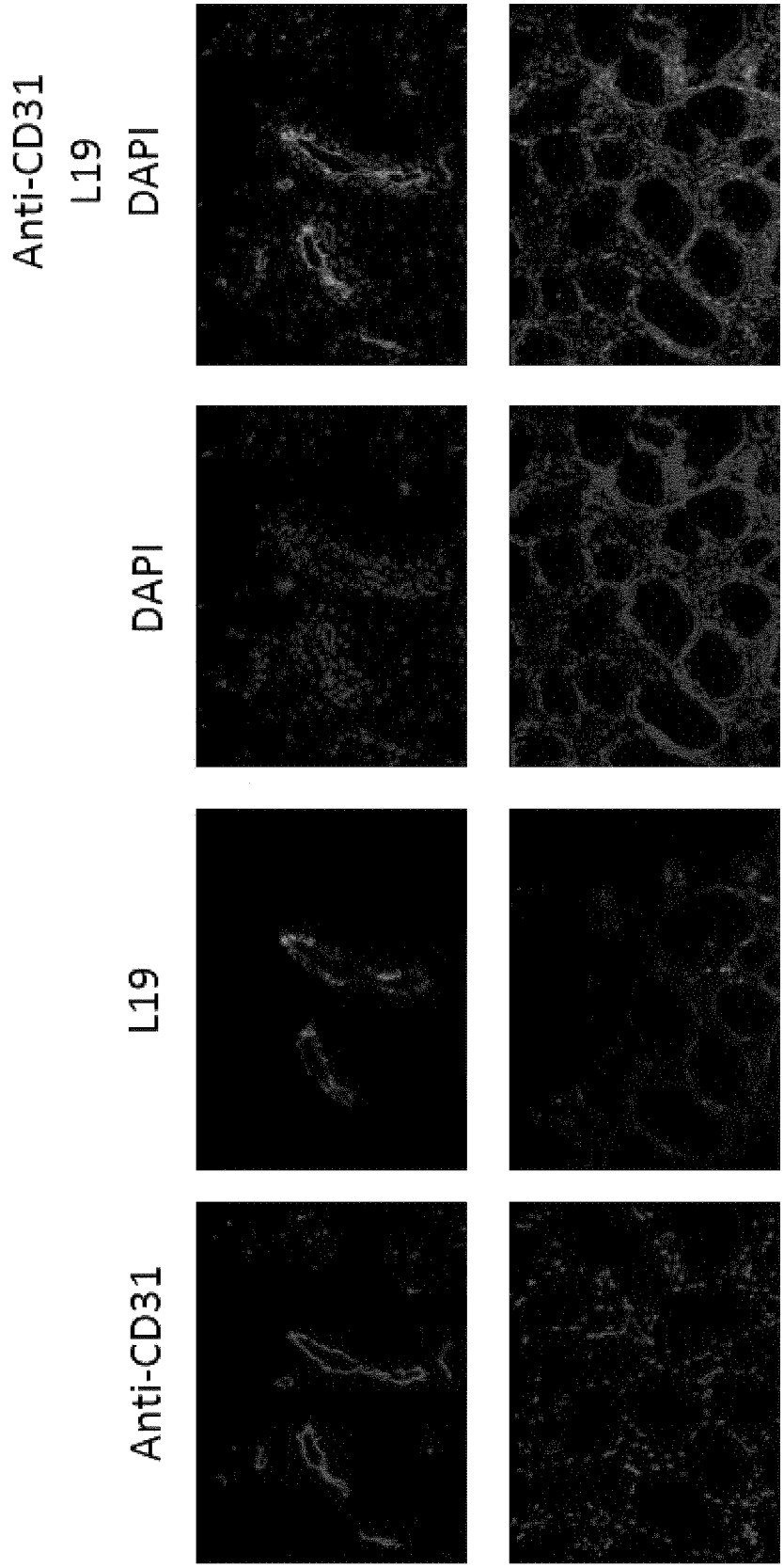
FIG. 2B shows positive staining of neovascular structures with the anti-EDB antibody L19, although less strong than the staining observed with the anti-IIICS antibody SW01.
Figure 2C:
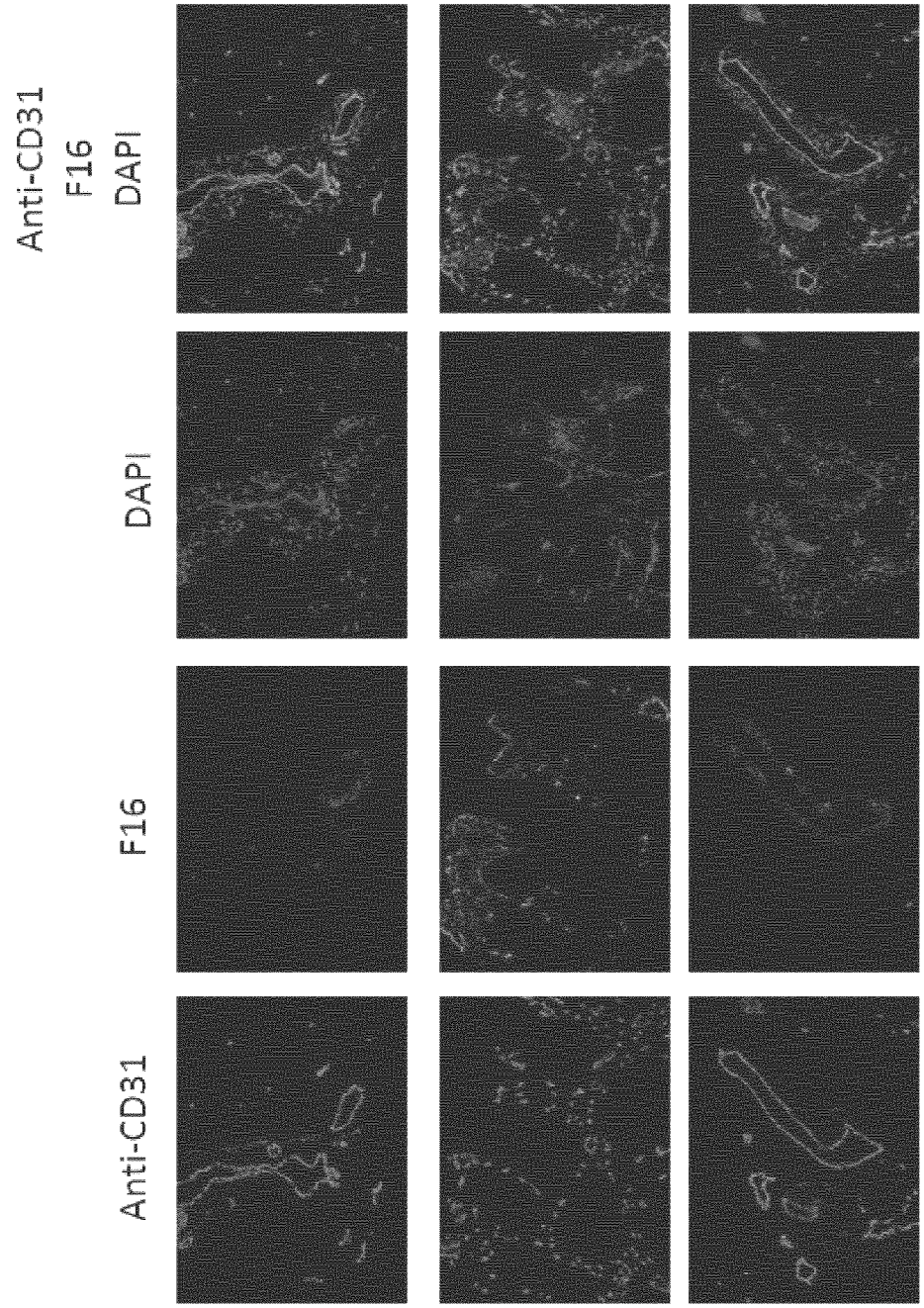
FIG. 2C shows positive staining of neovascular structures with the anti-Al TNC antibody F16. The staining observed with the F16 antibody is similar to that observed with antibody L19, and less strong than the staining observed with the anti-IIICS antibody SW01.
Figure 2D:
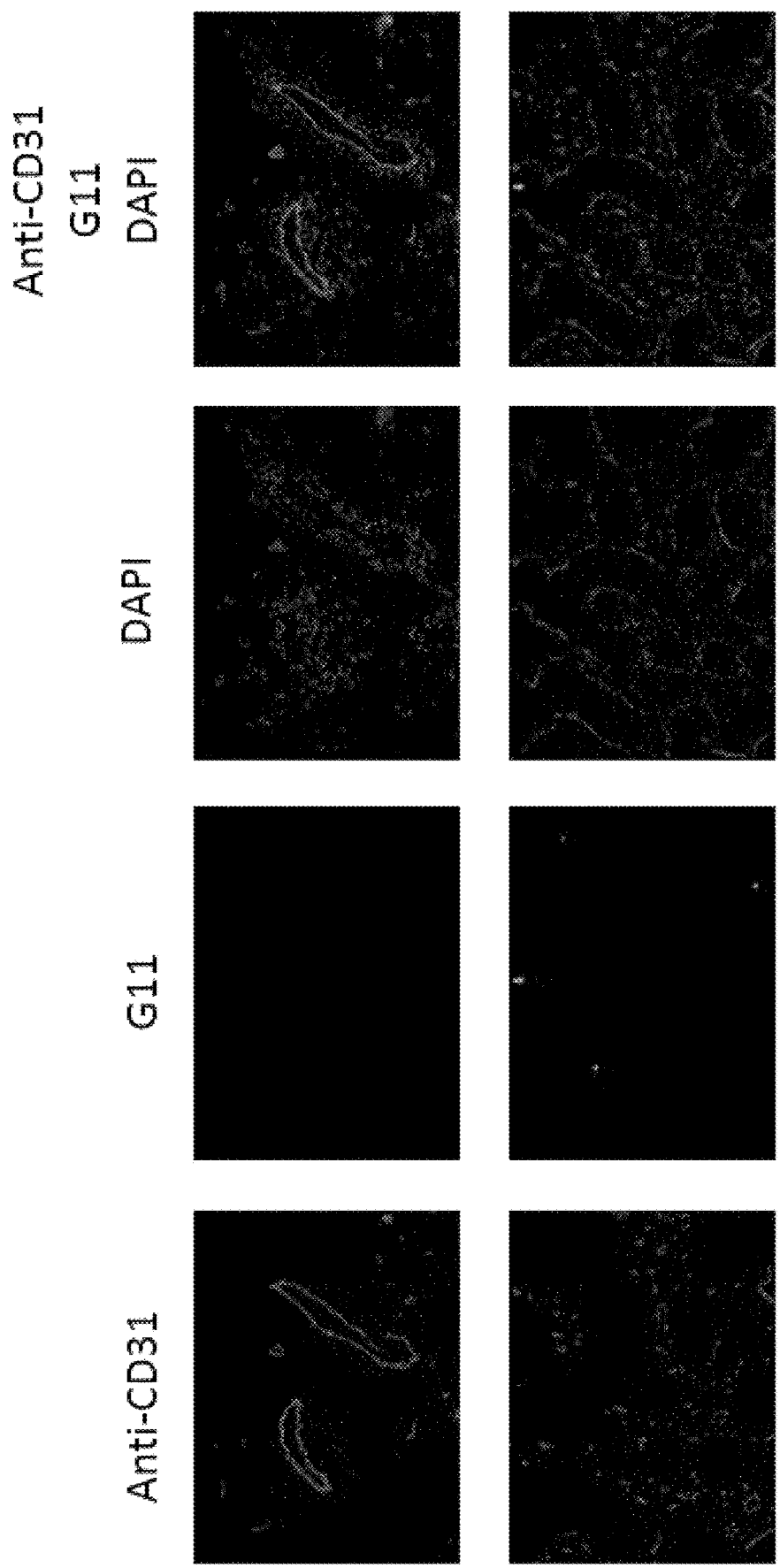
FIG. 2D shows that the anti-CTNC antibody G11 did not stain neovascular structures.
Figure 2E:
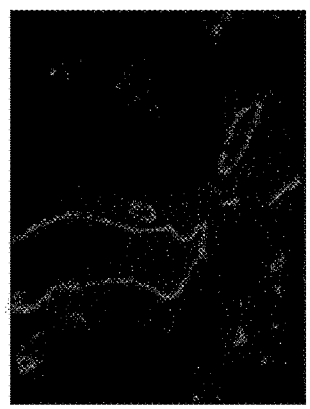
FIG. 2E shows positive staining of neovascular structures with the anti-MMP3 antibody CH01, although the observed staining was again less strong than that observed with the anti-IIICS antibody SW01.
Figure 2E:
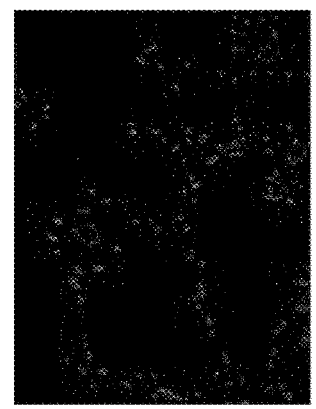
Figure 2E:
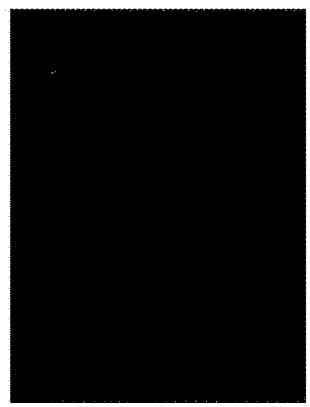
Figure 2E:
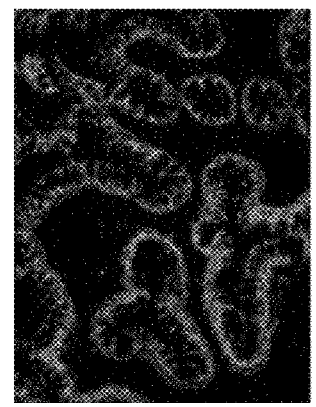
Figure 2E:
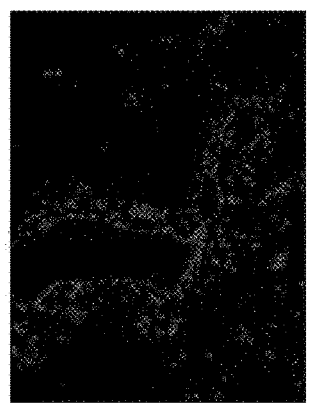
Figure 2E:
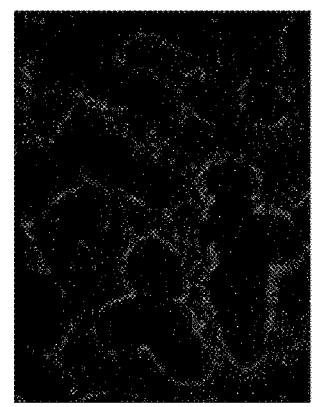
Figure 2E:
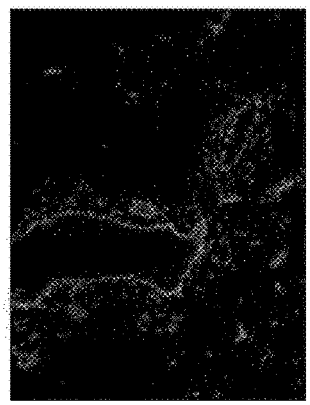
Figure 2E:
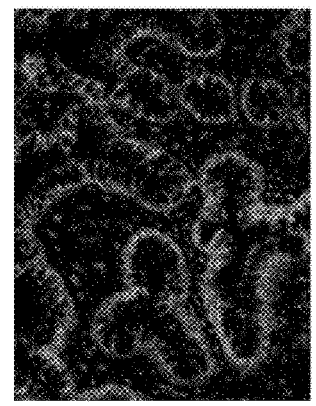
Figure 2F:
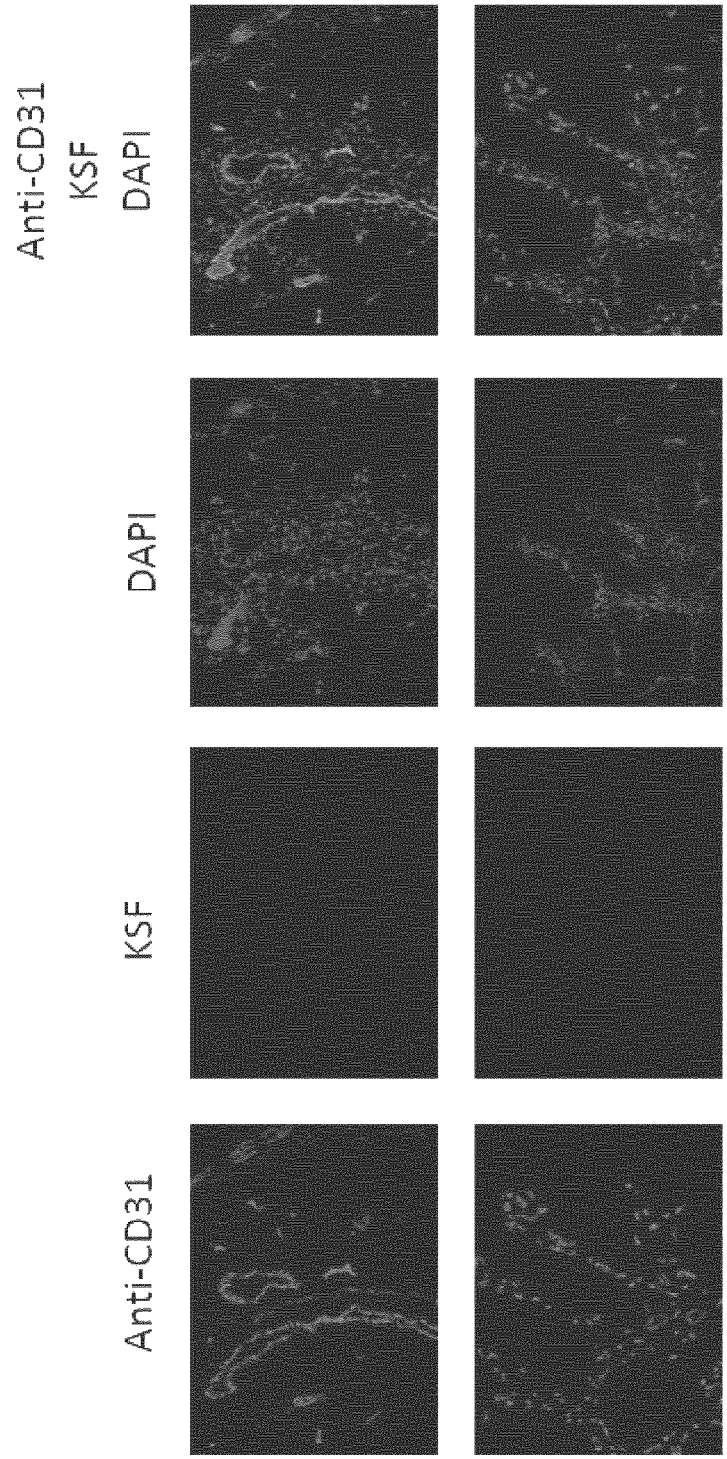
FIG. 2F shows that the anti-hens egg lysozyme (HEL) antibody KSF does not stain neovascular structures. The KSF antibody was used as a negative control, as hen egg lysozyme is not expressed in mammalian tissues.

The invention includes the combination of the aspects and preferred features described except where such a combination is clearly impermissible or expressly avoided.

In one aspect, the present invention relates to antibodies which bind (i) Human Lysozyme, (ii) Neutrophil Elastase, iii) Tissue Inhibitor of Metalloproteinase-1 (TIMP1), or (iv) the D domain of Tenascin-C.

Antibody Molecule

The term "antibody molecule" describes an immunoglobulin whether natural or partly or wholly synthetically produced. The term also covers any polypeptide or protein having a binding domain which is, or is substantially homologous to, an antibody binding domain.

Examples of antibodies are the immunoglobulin isotypes and their isotypic subclasses; fragments which comprise an antigen binding domain such single chain diabodies. The antibody molecule or fragment thereof may be human or humanised. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the CDRs of an antibody to the constant regions, or constant regions plus framework regions, of a different immunoglobulin. See, for instance, EP-A-184187, GB 2188638A or EP-A-239400. A hybridoma or other cell producing an antibody may be subject to genetic mutation or other changes, which may or may not alter the binding specificity of antibodies produced.

As antibodies can be modified in a number of ways, the term "antibody molecule" should be construed as covering antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023.

The term "specific" may be used to refer to the situation in which the antibody molecule will not show any significant binding to molecules other than its specific binding partner(s). The term is also applicable where e.g. an antigen-binding site of an antibody molecule is specific for a particular epitope that is carried by a number of antigens, in which case the antibody molecule carrying the antigen-binding site will be able to bind to the various antigens carrying the epitope.

The antibody molecule may be monovalent or bivalent i.e. may have two antigen binding sites. Where the antibody molecule is bivalent, the two antigen binding sites may be identical or different. An "antigen binding site" describes the part of an antibody which comprises the area which specifically binds to and is complementary to part or all of an antigen. Where an antigen is large, an antibody molecule may only bind to a particular part of the antigen, which part is termed an epitope. An antigen binding site may be provided by one or more antibody variable domains (e.g. a so-called Fd antibody fragment consisting of a VH domain). Preferably, an antigen binding site comprises an antibody light chain variable region (VL) and an antibody heavy chain variable region (VH).

The VH and VL can be further subdivided into regions of hyper-variability, termed complementarity determining regions ("CDRs"), interspersed with regions that are more conserved, termed framework regions ("FR"). Each VH and VL is composed of three CDRs and four FRs, arranged from amino-terminus to carboxy-terminus in the following order: FR1, CDR1, FR2, CDR2, FR3, CDR3, FR4. Herein, the three CDRs of the heavy chain are referred to as "HCDR1, HCDR2, and HCDR3" and the three CDRs of the light chain are referred to as "LCDR1, LCDR2 and LCDR3". The CDRs contain most of the residues which form specific interactions with the antigen.

Various systems are used to define the CDR residues within the antibody variable domains. The most commonly used systems are the Kabat and Chothia systems. The Kabat CDR definition (Kabat et al., "Sequences of Proteins of Immunological Interest," National Institutes of Health, Bethesda, Md. (1991)) is based upon antibody sequence variability. The Chothia CDR definition (Chothia et al., "Canonical structures for the hypervariable regions of immunoglobulins", Journal of Molecular Biology, 196, 901-917 (1987); Al-Lazikani et al., "Standard conformations for the canonical structures of immunoglobulins", Journal of Molecular Biology, 273, 927-948 (1997)) is based on three-dimensional structures of antibodies and topologies of the CDR loops. The CDRs defined by the Chothia system are identical to the CDRs defined by the Kabat system with the exception of HCDR1 and HCDR2.

In the present disclosure, the Kabat definition is used for HCDR2.

In the present disclosure, HCDR1 is defined using the Kabat system for the L19 and of the F16 antibody (L19: SEQ ID NO: 51, F16 SEQ ID NO: 59) in order to be consistent with previous patent disclosures. For other antibodies, HCDR1 is defined using the Chothia system. According to the Kabat definition, HCDR1 starts eight residues after the first cysteine of the heavy chain, whereas the Chothia definition of HCDR1 starts three residues after this cysteine. HCDR1 ends at the same residue in both systems. For example, the HCDR1 of CT01, FF01, FF02, SW01, CPR01 and CPR01.1 according to the Chothia system is GFTFSSYAMS and according to the Kabat system is SSYAMS; the HCDR1 of CH01 according to the Chothia system is GFTFSPYAMS and according to the Kabat system is SPYAMS; and the HCDR1 of 2PC10 according to the Chothia system is GFTFSSAAMS and according to the Kabat system is SSAAMS. Although the Chothia definition of HCDR1 is preferred for these antibodies, the present disclosure also encompasses these antibodies with HCDR1 defined according to the Kabat system.

An antibody molecule of the invention preferably comprises the HCDR3 of antibody CT01, antibody FF01, antibody FF02, antibody 2PC10, or antibody CPR01/CPR01.1. The HCDR3 is known to play a role in determining the specificity of an antibody molecule (Segal et al., (1974), PNAS, 71:4298-4302; Amit et al., (1986), Science, 233:747-753; Chothia et al., (1987), J. Mol. Biol., 196:901-917; Chothia et al., (1989), Nature, 342:877-883; Caton et al., (1990), J. Immunol., 144:1965-1968; Sharon et al., (1990a), PNAS, 87:4814-4817; Sharon et al., (1990b), J. Immunol., 144:4863-4869; Kabat et al., (1991b), J. Immunol., 147: 1709-1719).

The antibody molecule may further comprise the HCDR1, HCDR2, LCDR1, LCDR2 and/or LCDR3 of antibody CT01, antibody FF01, antibody FF02, antibody 2PC10, antibody CPR01, or antibody CPR01.1.

The antibody may also comprise the VH and/or VL domain of antibody CT01, antibody FF01, antibody FF02, antibody 2PC10, antibody CPR01, or antibody CPR01.1.

An antibody molecule of the invention may comprise a VH domain having at least 70%, more preferably one of at least 75%, 80%, 85%, 90%, 95%, 96%, 97%, 98%, 99% or 100%, sequence identity to the VH domain of antibody CT01, antibody FF01, antibody FF02, antibody 2PC10, antibody CPR01, or antibody CPR01.1.

An antibody molecule of the invention may comprise a VL domain having at least 70%, more preferably one of at least 75%, 80%, 85%, 90%, 95%, 96%, 97%, 98%, 99% or 100%, sequence identity to the VL domain of antibody CT01, antibody FF01, antibody FF02, antibody 2PC10, antibody CPR01, or antibody CPR01.1.

Sequence identity is commonly defined with reference to the algorithm GAP (Wisconsin GCG package, Accelerys Inc, San Diego USA). GAP uses the Needleman and Wunsch algorithm to align two complete sequences that maximizes the number of matches and minimizes the number of gaps. Generally, default parameters are used, with a gap creation penalty=12 and gap extension penalty=4. Use of GAP may be preferred but other algorithms may be used, e.g. BLAST (which uses the method of Altschul et al. (1990) J. Mol. Biol. 215: 405-410), FASTA (which uses the method of Pearson and Lipman (1988) PNAS USA 85: 2444-2448), or the Smith-Waterman algorithm (Smith and Waterman (1981) J. Mol Biol. 147: 195-197), or the TBLASTN program, of Altschul et al. (1990) supra, generally employing default parameters. In particular, the psi-Blast algorithm (Nucl. Acids Res. (1997) 25 3389-3402) may be used.

Variants of these VH and VL domains and CDRs may also be employed in antibody molecules for use in as described herein. Suitable variants can be obtained by means of methods of sequence alteration, or mutation, and screening.

Particular variants for use as described herein may include one or more amino acid sequence alterations (addition, deletion, substitution and/or insertion of an amino acid residue), maybe less than about 20 alterations, less than about 15 alterations, less than about 10 alterations or less than about 5 alterations, 4, 3, 2 or 1.

Alterations may be made in one or more framework regions and/or one or more CDRs. In particular, alterations may be made in HCDR1, HCDR2 and/or HCDR3.

The antibody molecule may be a whole antibody or a fragment thereof, in particular an antigen-binding fragment thereof.

Whole antibodies include IgA, IgD, IgE, IgG or IgM. Preferably, the whole antibody is IgG.

Antigen-binding fragments of whole antibodies include (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward et al. (1989) Nature 341, 544-546; McCafferty et al., (1990) Nature, 348, 552-554; Holt et al. (2003) Trends in Biotechnology 21, 484-490), which consists of a VH or a VL domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al. (1988) Science, 242, 423-426; Huston et al. (1988) PNAS USA, 85, 5879-5883); (viii) bispecific single chain Fv dimers (PCT/US92/09965) and (ix) "diabodies", multivalent or multispecific fragments constructed by gene fusion (WO2013/014149; WO94/13804; Holliger et al. (1993a), Proc. Natl. Acad. Sci. USA 90 6444-6448). Fv, scFv or diabody molecules may be stabilized by the incorporation of disulphide bridges linking the VH and VL domains (Reiter et al. (1996), Nature Biotech, 14, 1239-1245). Minibodies comprising a scFv joined to a CH3 domain may also be made (Hu et al. (1996), Cancer Res., 56(13):3055-61). Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A single chain Fv (scFv) may be comprised within a mini-immunoglobulin or small immunoprotein (SIP), e.g. as described in (Li et al., (1997), Protein Engineering, 10: 731-736). An SIP may comprise an scFv molecule fused to the CH4 domain of the human IgE secretory isoform IgE-S2 ($\varepsilon_{S2}$-CH4; Batista et al., (1996), J. Exp. Med., 184: 2197-205) forming an homo-dimeric mini-immunoglobulin antibody molecule Where the antibody molecule is a diabody, the VH and VL domains are preferably linked by a 5 to 12 amino acid linker. A diabody comprises two VH-VL molecules which associate to form a dimer. The VH and VL domains of each VH-VL molecule are preferably linked by a 5 to 12 amino acid linker. For example, the VH and VL domains may be linked by an amino acid linker which is 5, 6, 7, 8, 9, 10, 11, or 12 amino acid in length. Preferably, the amino acid linker is 5 amino acids in length. Suitable linker sequences are known in the art and include the linker sequence set forth in SEQ ID NO: 68.

Where the antibody molecule is an scFv, the VH and VL domains of the antibody are preferably linked by a 14 to 20 amino acid linker. For example, the VH and VL domains may be linked by an amino acid linker which is 14, 15, 16, 17, 18, 19, or 20 amino acid in length. Suitable linker sequences are known in the art and include the linker sequence set forth in SEQ ID NO: 67.

Where the antibody is a small immunoprotein (SIP), the VL domain of the scFv antibody is preferably linked to the CH4 domain of human IgE via a 5 to 20 amino acid linker, more preferably a 5 to 10 amino acid linker. Suitable linker sequences are known in the art and include the linker sequence set forth in SEQ ID NO: 83. The CH4 domain of human IgE preferably has the sequence set forth in SEQ ID NO: 84, or a sequence which has at least 70%, more preferably one of at least 75%, 80%, 85%, 90%, 95%, 96%, 97%, 98%, or 99% sequence identity to the sequence set forth in SEQ ID NO: 84.

Preferably the antibody molecule comprises or consists of a single chain Fv, a small immunoprotein, a diabody, or a (whole) IgG molecule.

Conjugates

Conjugates of the invention comprise an antibody molecule of the invention and a therapeutic or diagnostic agent. The therapeutic agent may be an immunosuppressive or anti-inflammatory agent, such as a cytokine.

The diagnostic agent may be a detectable label, such as a radioisotope, e.g. a non-therapeutic radioisotope.

Radioisotopes which may be conjugated to a binding member of the invention include isotopes such as $^{94m}$Tc, $^{99m}$Tc, $^{186}$Re, $^{188}$Re, $^{203}$Pb, $^{67}$Ga, $^{68}$Ga, $^{47}$Sc, $^{111}$In, $^{97}$Ru, $^{62}$Cu, $^{64}$Cu, $^{86}$Y, $^{88}$Y, $^{90}$Y, $^{121}$Sn, $^{161}$Tb, $^{153}$Sm, $^{166}$Ho, $^{105}$Rh, $^{177}$Lu, $^{123}$I, $^{124}$I, $^{125}$I, $^{131}$I, $^{18}$F, $^{211}$At and $^{225}$Ac. Preferably, positron emitters, such as $^{18}$F and $^{124}$I or gamma emitters, such as $^{99m}$Tc, $^{111}$In and $^{123}$I, are used for diagnostic applications (e.g. for PET), while beta-emitters, such as $^{131}$I, $^{90}$Y and $^{177}$Lu, are preferably used for therapeutic applications. Alpha-emitters, such as $^{211}$At and $^{225}$Ac may also be used for therapy. In one example, the specific binding member may be conjugated to $^{177}$Lu or $^{90}$Y.

The specific binding member may be conjugated to the immunosuppressive or anti-inflammatory agent, or detectable label, by means of a peptide bond or linker, i.e. within a fusion polypeptide comprising said molecule and the specific binding member or a polypeptide chain component thereof. Other means for conjugation include chemical conjugation, especially cross-linking using a bifunctional reagent (e.g. employing DOUBLE-REAGENTS' Cross-linking Reagents Selection Guide, Pierce).

Linkers

The antibody molecule and the therapeutic or diagnostic agent may be connected to each other directly, for example through any suitable chemical bond or through a linker, for example a peptide linker.

The peptide linker may be a short (2-20, preferably 2-15, residue stretch of amino acids). Suitable examples of peptide linker sequences are known in the art. One or more different linkers may be used. The linker may be about 5 amino acids in length.

The chemical bond may be, for example, a covalent or ionic bond. Examples of covalent bonds include peptide bonds (amide bonds) and disulphide bonds. For example the antibody molecule and therapeutic or diagnostic agent may be covalently linked. For example by peptide bonds (amide bonds). Thus, the antibody molecule and therapeutic or diagnostic agent may be produced (secreted) as a single chain polypeptide. The individual components that form the antibody molecule or the therapeutic or diagnostic agent may also be connected directly, for example through any suitable chemical bond, or through a linker, for example a peptide linker. Examples of individual components which may be linked within the antibody molecule are CDRs or VH or VL sequences.

For example, an immunosuppressive or anti-inflammatory agent, such as a cytokine, or a detectable label, may be conjugated, either through an amino acid linker, or directly, to the N-terminus or C-terminus of the antibody molecule. For example, where the antibody molecule is or comprises an scFv, the immunosuppressive or anti-inflammatory agent, or the detectable label, may be conjugated, either through an amino acid linker, or directly to the N-terminus of the VH domain of the scFv, or to the C-terminus of the VL domain of the scFv. Where the antibody molecule is a diabody (which comprises two scFv molecules), the immunosuppressive or anti-inflammatory agent, or the detectable label, may be conjugated, either through an amino acid linker, or directly, to the N-terminus of one or both of the VH domains, or to the C-terminus of one or both of the VL domains, of the two scFvs making up the diabody.

Methods of Treatment and Diagnosis

An antibody molecule or conjugate of the invention may be used in a method of treatment of the human or animal body, such as a method of treatment (which may include prophylactic treatment) of a disease or disorder in a patient (typically a human patient) comprising administering the antibody molecule or conjugate to the patient.

Accordingly, such aspects of the invention provide methods of treatment comprising administering an antibody molecule or conjugate of the invention, pharmaceutical compositions comprising such an antibody molecule or conjugate for the treatment of a condition or disease, and a method of making a medicament or pharmaceutical composition comprising formulating the antibody molecule or conjugate of the present invention with a physiologically acceptable carrier or excipient.

An antibody molecule or conjugate as herein described may be used in a method of treating an inflammatory disorder, preferably an inflammatory bowel disorder, or treating an autoimmune disease in a patient. The method may comprise targeting a therapeutic agent to the neovasculature in vivo. The agent may be any therapeutic agent discussed herein, which is suitable for treatment of the disease or disorder in question.

Also contemplated is a method of treating an inflammatory disorder, preferably an inflammatory bowel disorder, or treating an autoimmune disease in a patient by targeting a therapeutic agent to the neovasculature in a patient, the method comprising administering a therapeutically effective amount of an antibody molecule or conjugate as herein described to the patient.

An antibody molecule or conjugate as herein described may also be used in a method of imaging, detecting, or diagnosing a disease or disorder in a patient. A method of imaging, detecting, or diagnosing a disease or disorder comprising administering an antibody or conjugate as described herein to a patient is similarly contemplated. The disease or disorder may be an inflammatory disorder, preferably an inflammatory bowel disorder, or an autoimmune disease. The method may comprise targeting a diagnostic agent, such as a detectable label, to the neovasculature in vivo.

"Inflammatory disease and/or disorder" refers to diseases and/or disorders which are accompanied and/or characterised by inflammation. An inflammatory disease and/or disorder is preferably associated with and/or characterised by angiogenesis. An inflammatory disease and/or disorder may be an inflammatory disease and/or disorder characterised by angiogenesis, wherein the neovasculature expresses the ED-A isoform of fibronectin, the ED-B isoform of fibronectin and/or alternatively spliced Tenascin-C.

An autoimmune disease is preferably associated with and/or characterised by angiogenesis. An autoimmune disease may be an autoimmune disease characterised by angiogenesis, wherein the neovasculature expresses the ED-A isoform of fibronectin, the ED-B isoform of fibronectin and/or alternatively spliced Tenascin-C. The autoimmune disease may be an inflammatory autoimmune disease, i.e. an autoimmune disease associated with and/or characterised by inflammation. The inflammatory autoimmune disease may be any inflammatory autoimmune disease which is characterised by expression of the ED-A isoform of fibronectin, the ED-B isoform of fibronectin, and/or alternatively spliced tenascin C, in particular at sites of inflammation in the patient. The autoimmune disease may be selected from the group consisting of: inflammatory bowel disease (IBD), atherosclerosis, rheumatoid arthritis (RA), multiple sclerosis (MS), endometriosis, autoimmune diabetes (such as diabetes mellitus type 1), psoriasis, psoriatic arthritis, and periodontitis. Preferably, the autoimmune disease is IBD.

Inflammatory Bowel Disease is a group of inflammatory conditions that affect the colon and small intestine. The major types of IBD are Crohn's disease and ulcerative colitis, while other types of IBD include collagenous colitis, lymphocytic colitis, ischaemic colitis, diversion colitis, Behçet's disease and indeterminate colitis. Crohn's disease can affect any part of the gastrointestinal tract, whereas ulcerative colitis is typically restricted to the colon and rectum.

IBD, as referred to herein, may be Crohn's disease, ulcerative colitis, collagenous colitis, lymphocytic colitis, ischaemic colitis, diversion colitis, Behçet's disease or indeterminate colitis. In particular, the terms Crohn's disease, ulcerative colitis, collagenous colitis, lymphocytic colitis, ischaemic colitis, diversion colitis, Behçet's disease and indeterminate colitis, as used herein, may refer to active Crohn's disease, active ulcerative colitis, active collagenous colitis, active lymphocytic colitis, active ischaemic colitis, active diversion colitis, and active indeterminate colitis, respectively.

The inflammatory disorder or autoimmune disease is preferably inflammatory bowel disease, such as ulcerative colitis or Crohn's disease.

Another aspect of the invention provides an antibody molecule which binds to the D domain of Tenascin-C described herein for use in treating a proliferative disorder, such as cancer.

Another aspect of the invention provides a method of treating a proliferative disorder, such as cancer, comprising administering an antibody molecule which binds to the D domain of Tenascin-C described herein to an individual in need thereof. Preferably the individual is human.

Another aspect of the invention provides a method of diagnosing a proliferative disorder, such as cancer, in an individual, wherein the method comprises administering the antibody molecule which binds to the D domain of Tenascin-C described herein to the individual and detecting binding of the antibody molecule in the individual.

Other aspects of invention provide an antibody molecule which binds to the D domain of Tenascin-C described herein for use in a method of treating or diagnosing a proliferative disorder, such as cancer, and the use of an antibody molecule described herein in the manufacture of a medicament for use in a method of treating or diagnosing a proliferative disorder, such as cancer.

Preferred antibody molecules which bind to the D domain of Tenascin-C are described above and include CPR01.1.

An individual suitable for treatment with an antibody molecule which binds to D domain of Tenascin-C may have a proliferative disorder, preferably a cancer.

Proliferative disorders are caused or characterized by increased cell growth and proliferation and may include a pre-malignant or malignant neoplasm or tumour, (e.g. histocytoma, glioma, astrocyoma, osteoma), cancer (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, merkel cell carcinoma, pancreas cancer, brain cancer such as glioma, sarcoma, osteosarcoma, Kaposi's sarcoma, melanoma), a disease characterized by neovasculature or an angiogenic disease. Noncancerous tumours of any of these tissues may also be treated. Cancers may be familial or sporadic.

Treatment of a tumour or cancer in an individual may comprise eradication of the tumour. However, for many forms of tumours, especially malignant cancers and aggressive forms such as glioblastoma, complete cure may not be possible. Treatment may comprise retarding tumour growth and/or reducing tumour volume. Treatment may comprise lengthening the overall survival or progression free survival of the individual. Treatment may comprise improving quality of life of the individual, e.g. by reducing one or more symptoms caused by the tumour. Treatment may comprise inhibiting regrowth of the tumour following tumour regression. Treatment according to the present invention may be used to achieve any or all of these therapeutic effects.

The antibody molecule which binds to the D domain of Tenascin-C as described herein may be administered alone or in combination with other treatments, concurrently or sequentially or as a combined preparation with another therapeutic agent or agents, for the treatment of a disease, including a proliferative disorder, such as cancer. For example, an antibody molecule which binds to the D domain of Tenascin-C as described herein may be used in combination with an existing therapeutic agent for the treatment of a proliferative disorder, such as cancer. Therapeutic agents may include anti-cancer compounds which are well-known in the art such as: alkylating agents, antimetabolites, plant alkaloids and terpenoids, topoisomerase inhibitors, anti-tumour antibiotics, monoclonal antibodies, and corticosteroids.

Pharmaceutical Compositions

A further aspect of the present invention relates to a pharmaceutical composition comprising at least one antibody molecule or conjugate of the invention and optionally a pharmaceutically acceptable excipient.

Pharmaceutical compositions of the present invention typically comprise a therapeutically effective amount of an antibody molecule or conjugate according to the invention and optionally auxiliary substances such as pharmaceutically acceptable excipient(s). Said pharmaceutical compositions are prepared in a manner well known in the pharmaceutical art. A carrier or excipient may be a liquid material which can serve as a vehicle or medium for the active ingredient. Suitable carriers or excipients are well known in the art and include, for example, stabilisers, antioxidants, pH-regulating substances, controlled-release excipients. The pharmaceutical composition of the invention may be adapted, for example, for parenteral use and may be administered to the patient in the form of solutions or the like.

Pharmaceutical compositions comprising the antibody molecule or conjugate of the present invention may be administered to a patient. Administration is preferably in a "therapeutically effective amount", this being sufficient to show benefit to the patient. Such benefit may be amelioration of at least one symptom. The actual amount administered, and rate and time-course of administration, will depend on the nature and severity of what is being treated. Prescription of treatment, e.g. decisions on dosage etc., is within the responsibility of general practitioners and other medical doctors. Treatments may be repeated at daily, twice-weekly, weekly, or monthly intervals at the discretion of the physician.

A pharmaceutical composition of the invention may be administered to a patient in need of treatment via any suitable route, usually by injection into the bloodstream and/or directly into the site to be treated. The precise dose and its frequency of administration will depend upon a number of factors, the route of treatment, the size and location of the area to be treated.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included For intravenous injection, or injection at the site of affliction, the pharmaceutical composition will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, anti-oxidants and/or other additives may be included, as required.

A pharmaceutical composition may be administered alone or in combination with other treatments, either simultaneously or sequentially dependent upon the condition to be treated.

Kits

Another aspect of the invention provides a therapeutic kit for use in the treatment of a disease or disorder comprising an antibody molecule or conjugate of the invention. The components of a kit are preferably sterile and in sealed vials or other containers.

A kit may further comprise instructions for use of the components in a method described herein. The components of the kit may be comprised or packaged in a container, for example a bag, box, jar, tin or blister pack.

Further aspects and embodiments of the invention will be apparent to those skilled in the art given the present disclosure including the following experimental exemplification.

All documents mentioned in this specification are incorporated herein by reference in their entirety for all purposes.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXAMPLES

Example 1

Preparation and Characterisation of the Novel Antibodies CT01 against Lysozyme, FF01 and FF02 against Neutrophil Elastase, 2PC10 against TIMP-1, CPR01 and CPR01.1 against Domain D of Tenascin C The antibodies against human lysozyme, human neutrophil elastase, human TIMP-1 and domain D of human tenascin C, antibodies CT01, FF01 and FF02, 2PC10, CPR01 and CPR01.1, were isolated in single-chain Fv (scFv) configuration from phage display libraries, which included the libraries described in PCT/EP2009/006487, Weber et al. (PLoS One, 2014, 9 (6) doi: 10/1361) and Silacci et al. (Protein Engineering Design & Selection, 2006, 19, 471-478), according to the screening technique described by Silacci et al. (Protein Engineering Design & Selection, 2006, 19, 471-478) using lysozyme, neutrophil elastase, TIMP-1, and domain D of tenascin C, respectively, as the screening antigen.

Antibodies in SIP format were prepared by fusing the VL domain sequence of the antibody in scFv format to the CH4 domain of human IgE via using overlap extension PCR. The SIP construct was then fused to a mammalian leader sequence using overlap extension PCR and subcloned into the pcDNA3.1 vector using the restriction enzymes HindIII and NotI. The protein was expressed in CHO.S cells using PEI-mediated transient gene expression, and purified from the culture supernatant by affinity chromatography using protein A resin (Sino Biological Inc.). The sequence of the linker linking the VL domain to the CH4 domain of human IgE is shown in SEQ ID NO: 83. The sequence of the CH4 domain of human IgE is shown in SEQ ID NO: 84. The sequence of the FF02 antibody in SIP format is shown in SEQ ID NO: 82.

Results:

The binding of antibodies CT01 to lysozyme, 2PC10 to TIMP-1, CPR01 and CPR01.1 to domain D of tenascin-C was further confirmed by Biacore analysis as described below. The corresponding results are shown in FIG. 1. The binding of antibodies FF01 and FF02 to human neutrophil elastase was confirmed by ELISA. The corresponding results are shown in FIG. 6.

The affinity measurements for the binding of CT01 to the lysozyme are shown in the table 1. The Biacore analysis demonstrates that scFv(CT01) had an affinity (KD) for the lysozyme of $8.9 \times 10^{-7}$ M.

TABLE 1

| Ka (1/Ms) | Kd (1/s) | KD (M) |
|---|---|---|
| 8.72E03 | 7.7E−03 | 8.9E−07 |

The affinity measurements for the binding of CPR01 to the D domain of human Tenascin-C are shown in the table 2.

TABLE 2

| Ka (1/Ms) | Kd (1/s) | KD (M) |
|---|---|---|
| 151000 | 0.011 | 7.0E−08 |

The affinity measurements for binding of CPR01 to the BCD domains of murine tenascin-C are shown in table 3.

TABLE 3

| Ka (1/Ms) | Kd (1/s) | KD (M) |
|---|---|---|
| 240000 | 7.0E−3 | 2.9E−08 |

The Biacore analysis demonstrates that scFv(CPR01) had an affinity (KD) for the D domain of human Tenascin-C of $7.0 \times 10^{-8}$ M and a KD for the BCD domains of murine tenascin-C of $2.9 \times 10^{-8}$ M and thus the species cross-reactivity of this antibody.

The affinity measurements for the binding of CPR01.1 to the D domain of human tenascin-C are shown in the table 4.

TABLE 4

| Ka (1/Ms) | Kd (1/s) | KD (M) |
|---|---|---|
| 78300 | 0.067 | 8.5E−07 |

The affinity measurements for binding of CPR01.1 to the BCD domains of murine tenascin-C are shown in table 5.

TABLE 5

| Ka (1/Ms) | Kd (1/s) | KD (M) |
|---|---|---|
| 150000 | 0.064 | 4.3E−07 |

The Biacore analysis demonstrates that scFv(CPR01.1) had an affinity ($K_D$) for the D domain of human Tenascin-C of $8.5 \times 10^{-7}$ M and a KD for the BCD domains of murine tenascin-C of $4.3 \times 10^{-7}$ M and thus the species cross-reactivity of this antibody.

The affinity measurements for the binding of CH01 to human MMP3 is shown in the table 6.

TABLE 6

| Ka (1/Ms) | Kd (1/s) | KD (M) |
|---|---|---|
| 1.7E05 | 4.7E−03 | 2.8E−08 |

The affinity measurements for the binding of CH01 to murine MMP3 is shown in the table 7.

TABLE 7

| Ka (1/Ms) | Kd (1/s) | KD (M) |
|---|---|---|
| 8.0E04 | 2.5E−03 | 2.9E−08 |

The Biacore analysis demonstrates that scFv(CH01) had an affinity ($K_D$) for the human MMP3 of $2.8 \times 10^{-8}$ M and an affinity ($K_D$) for the murine MMP3 of $2.9 \times 10^{-8}$ M.

The affinity measurements for the binding of SW01 to IIICS isoform of fibronectin is shown in the table 8. The Biacore analysis demonstrates that scFv(SW01) had an affinity (KD) for the IIICS isoform of fibronectin of $2.62 \times 10^{-7}$ M

TABLE 8

| Ka (1/Ms) | Kd (1/s) | KD (M) |
|---|---|---|
| 1.84E05 | 0.048 | 2.62E−07 |

Biacore Analysis:

CT01, CPR01 and 2PC10 were expressed in CHO.S cells as ScFv antibody fragments and purified from the culture supernatant by affinity chromatography using protein A resin (Sino Biological Inc.).

CT01 was analysed for antigen binding by Biacore using a CM5 chip coated with commercial native human lysozyme (from human neutrophils; Cat-No. L8402; SIGMA) to a final coating density of 2000 resonance units (RU). The flow rate for the Biacore analysis was set at 20 µL/min.

CPR01 was analysed for antigen binding by Biacore using a CM5 chip coated with the human tenascin-C D domain. The flow rate for the Biacore analysis was set at 10 µL/min.

ScFv (CPR01.1) antibody fragments were expressed in CHO.S cells and purified from the culture supernatant by affinity chromatography using protein A resin (Sino Biological Inc.)

The eluted fractions containing ScFv antibody fractions were analysed for antigen binding by BIAcore using a CM5 chip coated with the D domain of human Tenascin-C. Binding to the BCD domain of murine Tenascin-C coated on a CM5 chip was also assessed to determine species cross-reactivity of the antibody. Analysis was run in phosphate buffer (100 mM sodium phosphate pH 7.4, 100 mM NaCl) at a flow rate of 10 µL/min and after each injection the chip was regenerated with 5 µL of 10 mM HCl.

2PC10 was analysed for antigen binding by Biacore using a CM5 chip coated with rHsTIMP1 (a recombinant polypeptide which includes the hs-TIMP1 sequence, aa24-207, and 6×His at the C-terminus of the protein) to achieve a final coating density of 3500 resonance units (RU). The flow rate for the Biacore analysis was set at 10 µL/min.

ELISA Analysis

Elastase (ELANE) protein from human neutrophils was purchased from MyBiosource (MBS173384). Human Neutrophil Elastase (MyBiosource) was biotinylated according to the standard protocol. The degree of biotinylation was ≈0.3-0.6 biotin/molecule.

ELISA with the FF01 and FF02 Antibodies in scFv Format

MAXIsorp strips (Nunc) were coated with HNE at $10^{-6}$ M. Coated plates were incubated with myc-tagged FF01, FF02 scFv fragments or with a negative control anti-hen egg lysozyme scFv at different concentrations (100 µg/ml, 50 µg/ml, 25 µg/ml or 12.5 µg/ml) for 1 hour. Bound antibody was detected with the anti-Myc antibody 9E10 (1:500 dilution) and an HRP-conjugated anti-Murine $F_c$ antibody (Sigma). (1:1000 dilution). Colorimetric detection of antibody-antigen binding was performed using BM-Blue POD soluble substrate (Roche). The optical density was measured at 450 nM.

ELISA with FF01 and FF02 Antibodies in SIP Format

Streptawell High Bind strips (Roche) were coated with biotinylated HNE at $3.5 \times 10^{-6}$ M. Coated plates were incubated with the FF01 or with the FF02 antibody in SIP format (50 pg/ml) for 1 hour. Bound antibody was detected with a Rabbit anti-human IgE (Sigma) and an HRP-conjugated anti-Rabbit IgG antibody (Sigma). The plate coating density was assessed by detecting the immobilized HNE using an HNE-specific Rabbit IgG (Abcam 68672, 1:150 dilution) and detection with an HRP-conjugated anti-Rabbit IgG antibody (1:1000 dilution, Sigma).

Colorimetric detection of antibody-antigen binding was performed using BM-Blue POD soluble substrate (Roche). The optical density was measured at 450 nM.

Results:

The results are shown in FIG. 6 and confirm that the FF01 and FF02 antibodies bind to human neutrophil elastase both in scFv and in SIP format.

Example 2

Immunofluorescence Staining of Sections from Ulcerative Colitis Patients

Freshly frozen biopsy samples of Ulcerative Colitis were stained according to published methods (S. Pfaffen. Eur J Nucl Med Mol Imaging 2010). In brief, purified biotinylated antibodies in SIP (KSF) or IgG (SW01, L19, F16, CH01, G11) format were added at the final concentration of 2pg/ml to the sections. Detection of the primary antibody was performed with streptavidine-Alexa-488 antibody (Invitrogen).

Positive control was performed by staining blood vessels with an antibody (eBioscience, 1:100) specific for CD31, an endothelial cell marker, the signal revealed with goat anti-mouse Alexa-594 (Invitrogen). Further positive control was performed by counterstaining for cell nuclei was performed with DAPI (eBioscience). Sections were mounted with fluorescent mounting medium (DAKO) followed by analysis using an Axioskop2 microscope with a 10× objective (Carl Zeiss A G, Jena, Germany). The results are shown in FIG. 2.

Example 3

Immunofluorescence Staining of HT29 Cells with the CT01 Antibody

Figure 3:
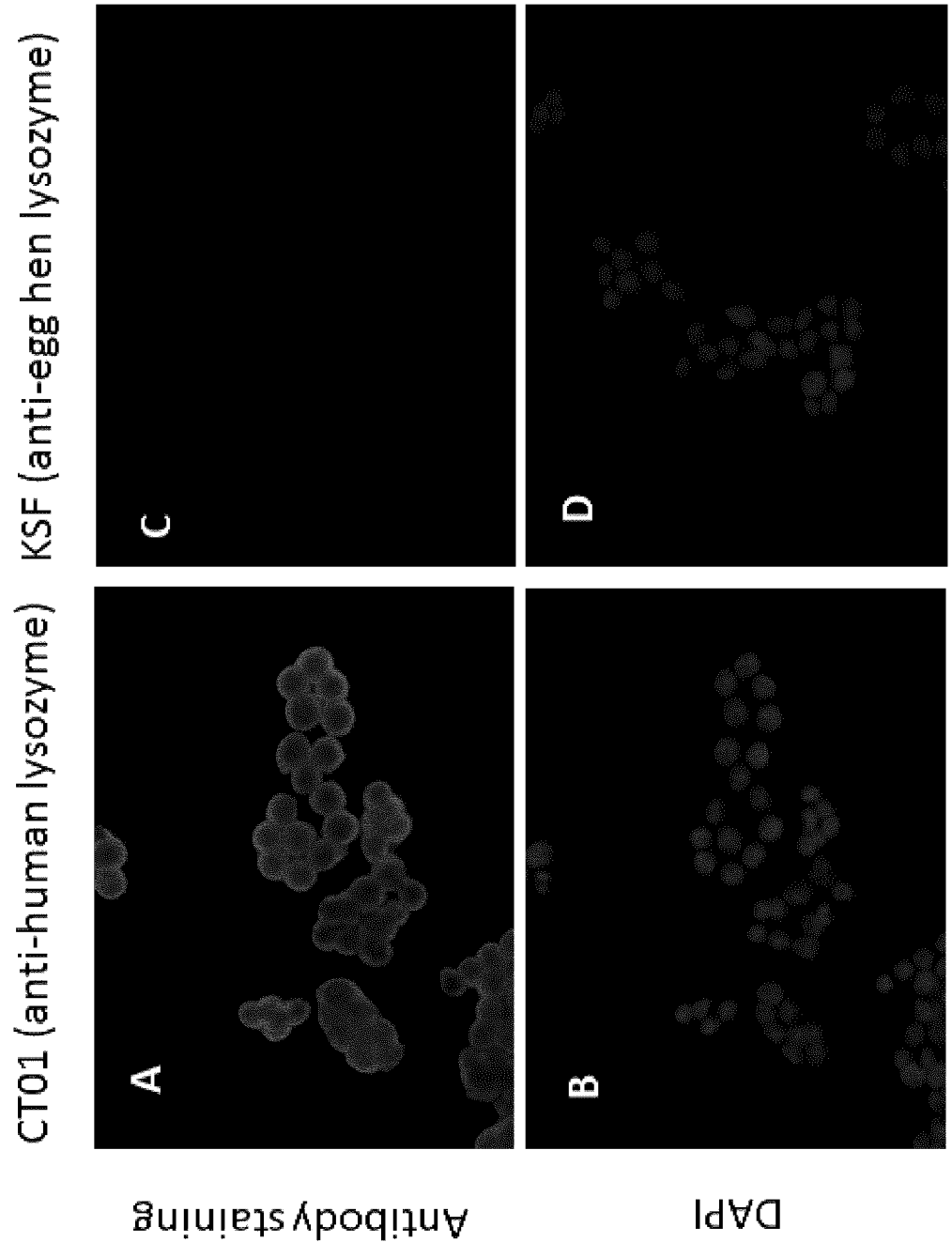
FIG. 3 shows the results of immunofluorescence experiments performed in cultured HT29 cells and HeLA cells using the anti-human lysozyme antibody CT01.

Coverslips were placed into culture dishes (100 mm×20 mm), and HT29 cells (both human adenocarcinoma cell lines) were then seeded at 100,000 cells/mL in the culture dishes respectively. The culture was incubated until proper confluency was reached. Cells were fixed and permeabilized by ice-cold methanol incubation at −20° C. Cells were then blocked with 10% FBS/2% BSA. Affinity-purified antibody CT01, in SIP format (final concentration 5 µg/ml) was first incubated with the cells, followed by incubation with a rabbit anti-human IgE antibody (1:500 dilution; DAKO). The antibody was then detected with goat anti-rabbit IgG Alexa 488 (1:1000 dilution; Invitrogen). DAPI was used for nuclei staining. The anti-hen egg Lysozyme SIP antibody (KSF) was used as an isotype-negative control for the staining. The results demonstrate that the anti-human lysozyme antibody CT01 is capable of staining lysozyme in biological samples (FIG. 3).

Example 4

Figure 4:
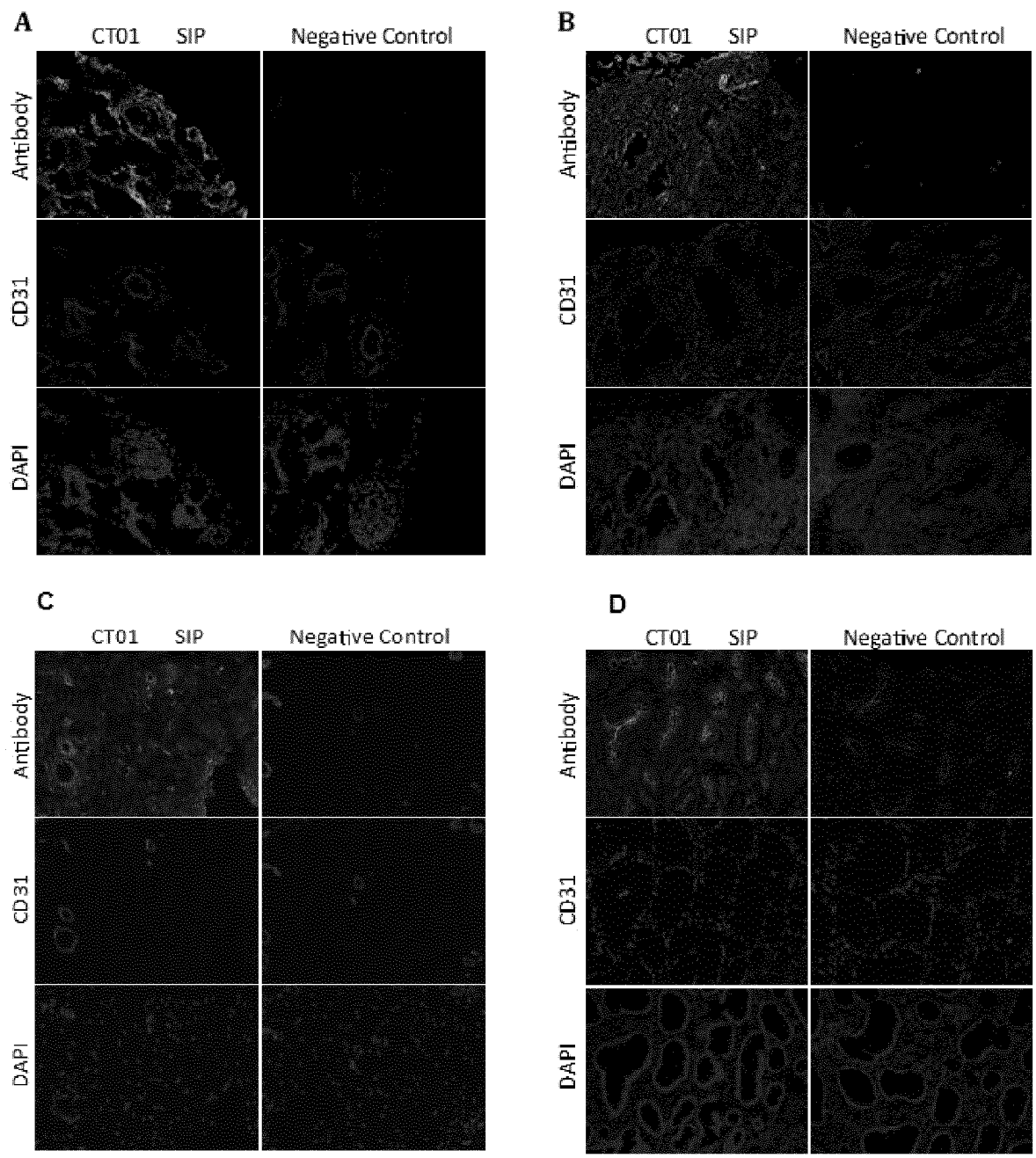
FIG. 4 shows the results immunofluorescence experiments performed on colitis/Crohn's disease biopsy samples from two patients with colitis and two patients with Crohn's disease. When the sections were probed with the anti-human lysozyme antibody CT01 antibody in SIP format, fluorescent staining of epithelia is clearly visible but not when probed with the negative control antibody anti-egg hen lysozyme KSF in the same SIP format. An anti-CD31 antibody (specific for an endothelial marker) was used as a positive control. DAPI staining of the nuclei was also performed.
Figure 4:
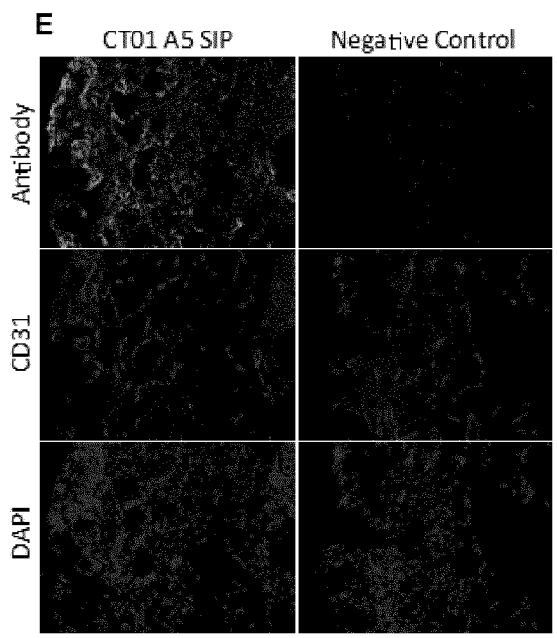
Figure 4:
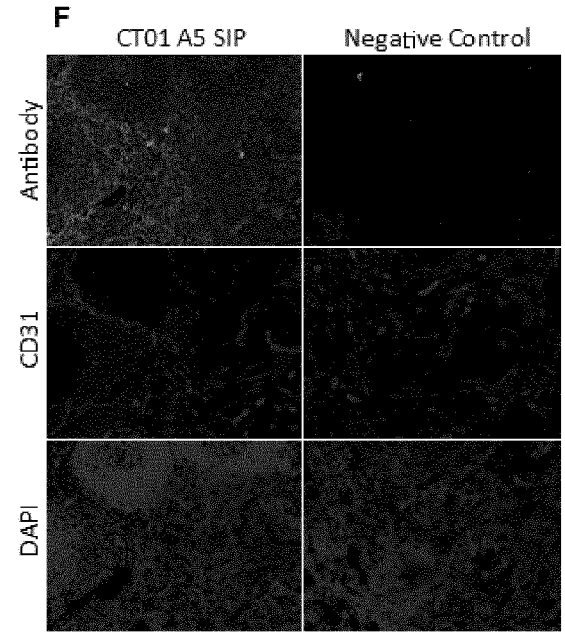
Figure 4:
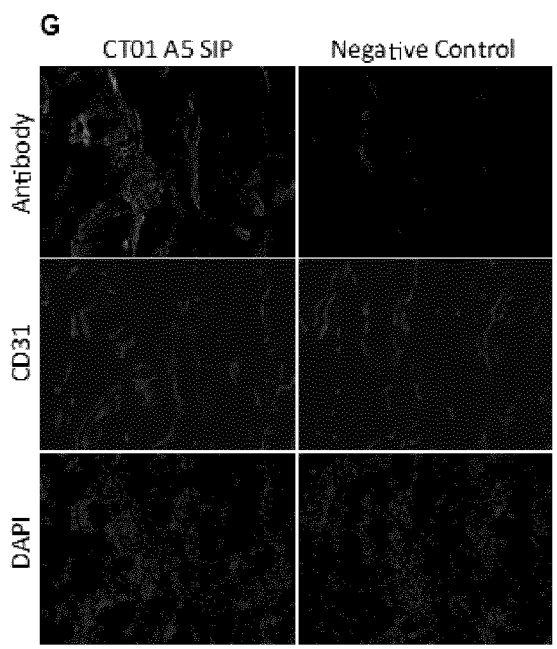
Figure 4:
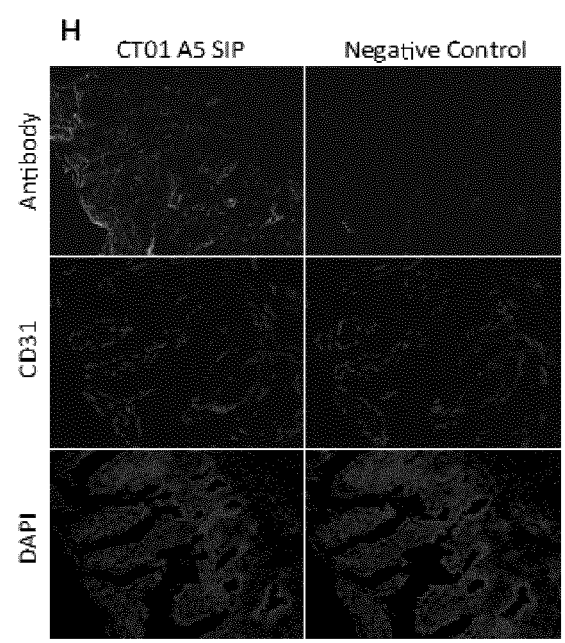

Immunofluorescence Staining of Biopsies taken from Ulcerative Colitis and Crohn's Disease Patients with CT01 Antibody Staining for lysozyme and CD31 (as an endothelial marker) was performed on human colitis and Crohn's disease biopsy samples. 10 µm thickness frozen specimens were defrosted at room temperate and treated with ice-cold methanol, rehydrated in PBS and blocked with 20% FCS. Affinity-purified SIPs (final concentration 5 µg/mL) were first incubated with the tissue samples, followed by rabbit anti-human IgE antibody (1:500 dilution; DAKO) and the mouse anti-human CD31 antibody (1:200 dilution; eBioscience). Bound SIPs were detected with goat anti-rabbit IgG Alexa 488 (1:200 dilution; Invitrogen), while the anti-CD31 antibody was detected using goat anti-mouse IgG Alexa 594 (1:200 dilution; Invitrogen). DAPI was used for nuclei staining. The anti-hen egg lysozyme antibody ScFv(KSF) was used as an isotype-negative control for the staining. The results demonstrate that the anti-human lysozyme antibody CT01 antibody is capable of staining epithelia in human biopsy samples of colitis and Crohn's disease (FIG. 4).

Example 5

Figure 5:
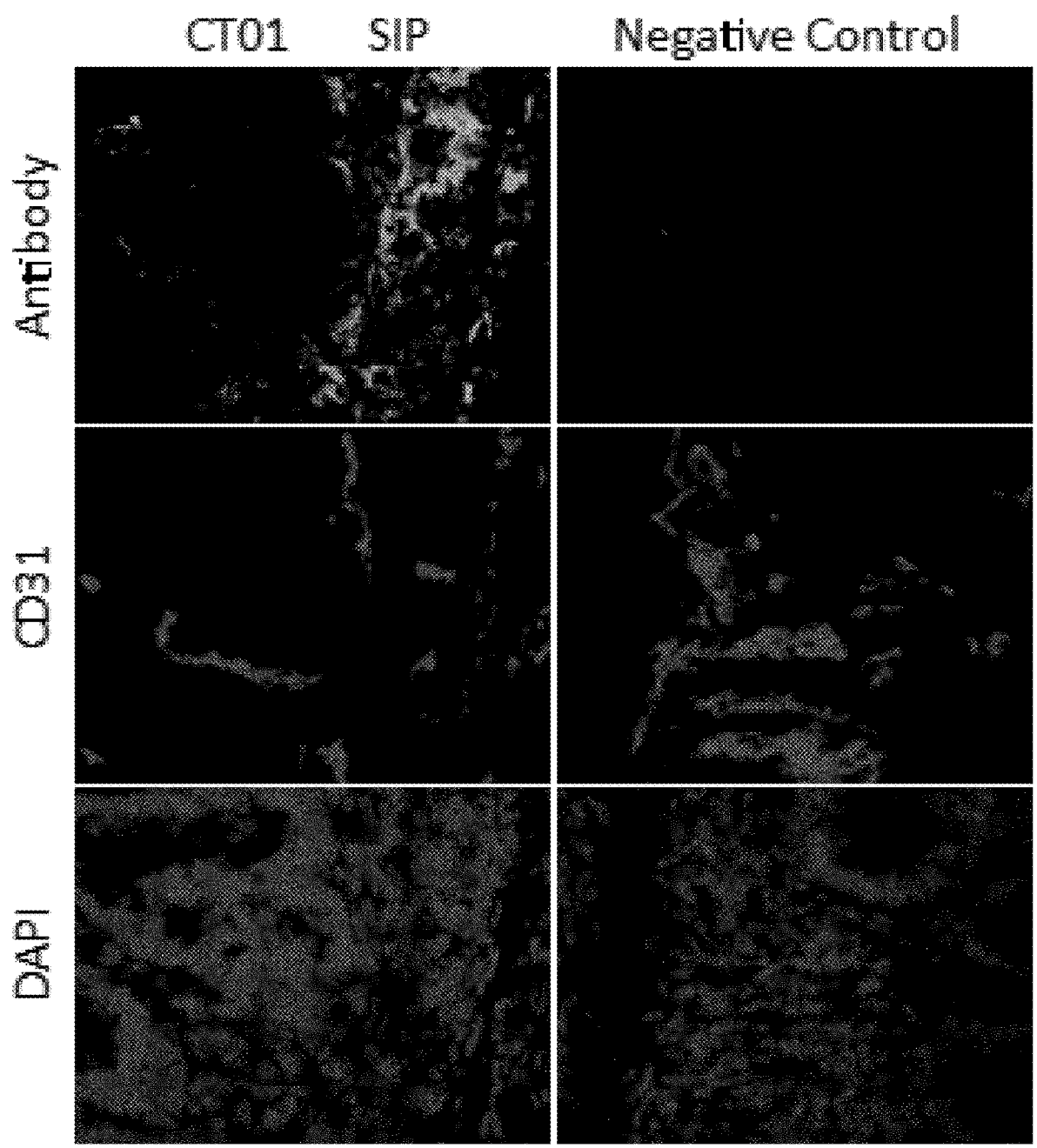
FIG. 5 shows the results of immunofluorescence experiments performed on samples taken from the intestine of a mouse with colitis. The experiments were run to confirm whether or not the anti-human lysozyme antibody CT01 cross-reacts with murine lysozyme. When the sections were probed with the CT01 antibody in SIP format, fluorescence staining is clearly visible but not when probed with the negative control antibody anti-egg hen lysozyme KSF in the same SIP format. An anti-CD31 antibody (specific for an endothelial marker) was used as positive control. DAPI staining of the nuclei was also performed.
Figure 6A:
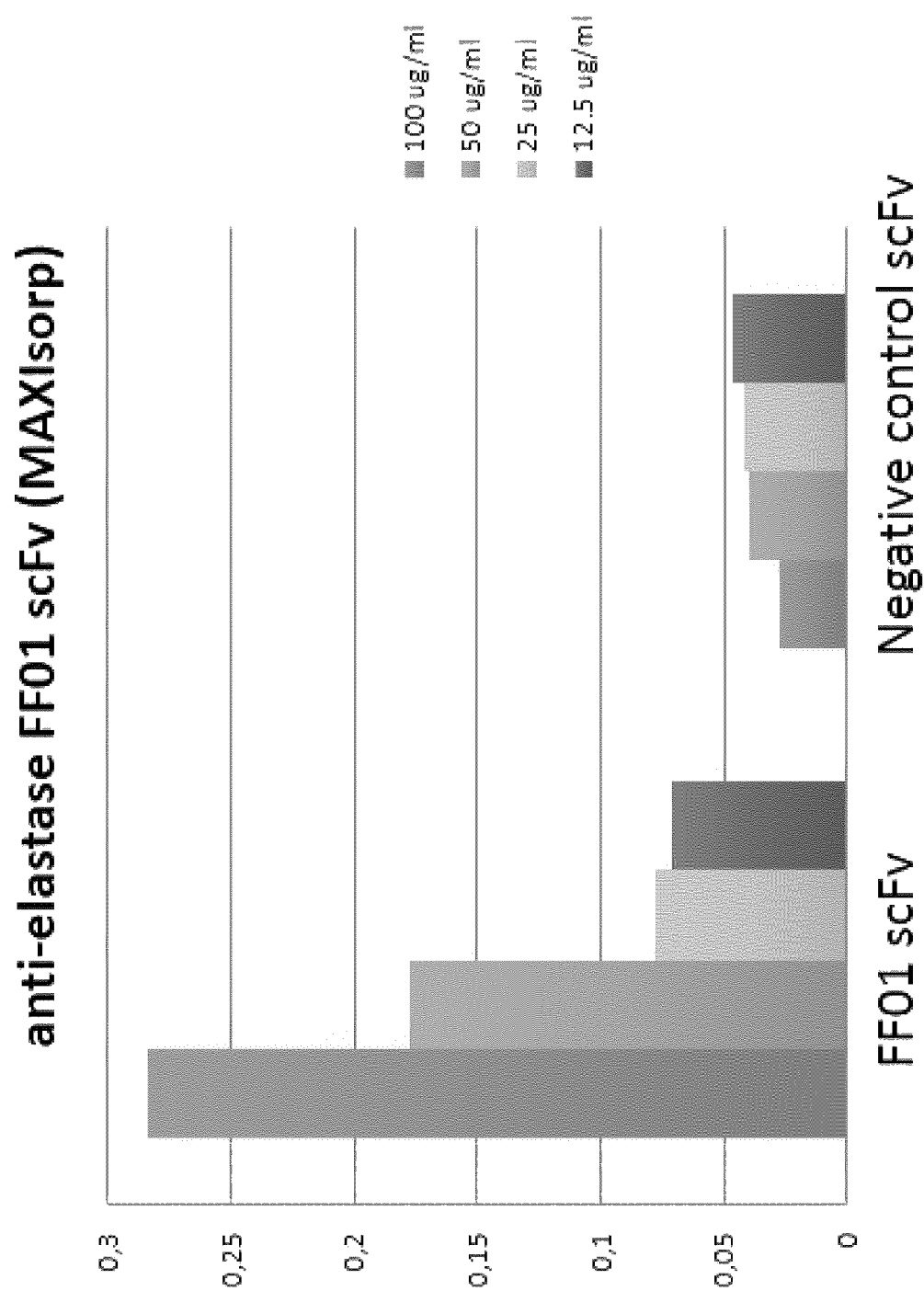
FIG. 6A and B show the binding of the FF01 antibody to human neutrophil elastase.
Figure 6B:
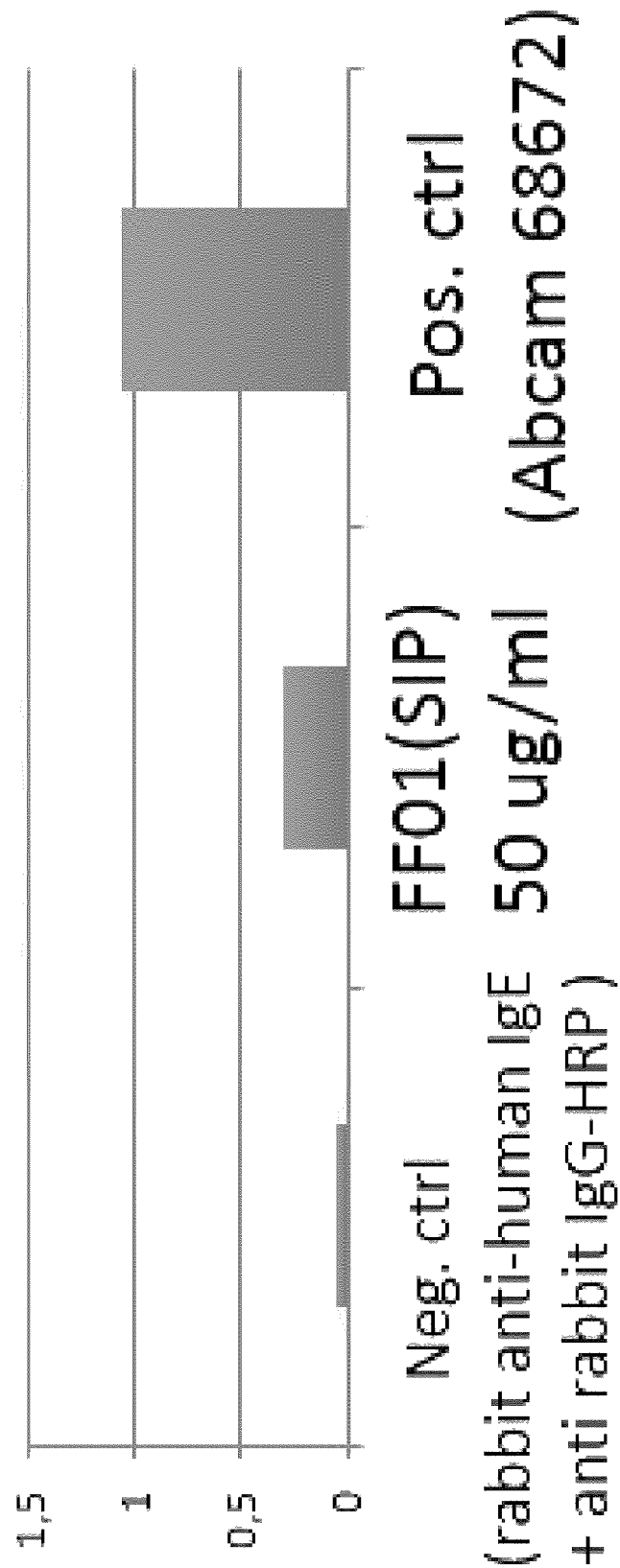
FIG. 6 shows the ELISA characterization of the FF01 and FF02 antibodies and confirms their binding to human neutrophil elastase.
FIG. 6C and D show the binding of the FF02 antibody to human neutrophil elastase. "ug/ml" refers to µg/ml. The y-axis in FIG. 6A-D shows the optical density (OD) as measured at 450 nM.
Figure 6C:
Figure 6D:
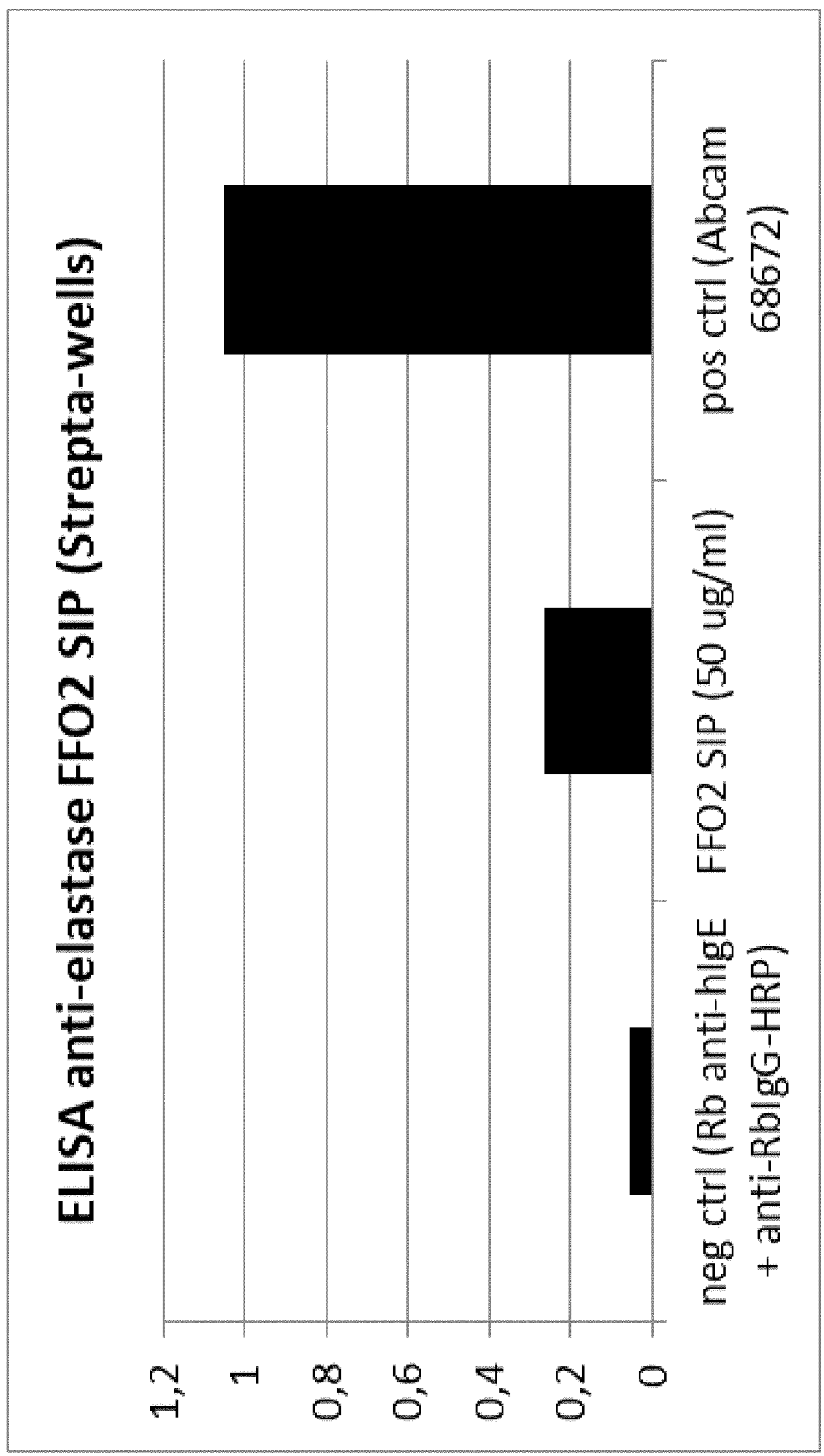

Immunofluorescence Staining of Samples taken from Mice with Colitis with the CT01 Antibody 10 µm thick frozen biopsy specimens from a colitis mouse model were defrosted at room temperate and treated with ice-cold methanol, rehydrated in PBS and blocked with 20% FCS. Affinity-purified SIPs (final concentration 5 µg/mL) were first incubated with the tissue sample, followed by rabbit anti-human IgE antibody (1:500 dilution; DAKO) and the rat anti-mouse CD31 antibody (1:200 dilution; BD Biosciences). Bound SIPs were detected with goat anti-rabbit IgG Alexa 488 (1:200 dilution; Invitrogen), while the anti-CD31 antibody was detected using donkey anti-rat IgG Alexa 594 (1:200 dilution; Invitrogen). DAPI was used for nuclei staining. The anti-hen egg lysozyme antibody ScFv (KSF) was used as an isotype-negative control for the staining. The results demonstrate that the anti-human lysozyme antibody CT01 is capable of binding to mouse lysozyme, i.e. cross-reacts with mouse lysozyme, which is useful for testing the CT01 antibody, and conjugates thereof, in mouse models of IBD (FIG. 5).

Example 6

Figure 7:
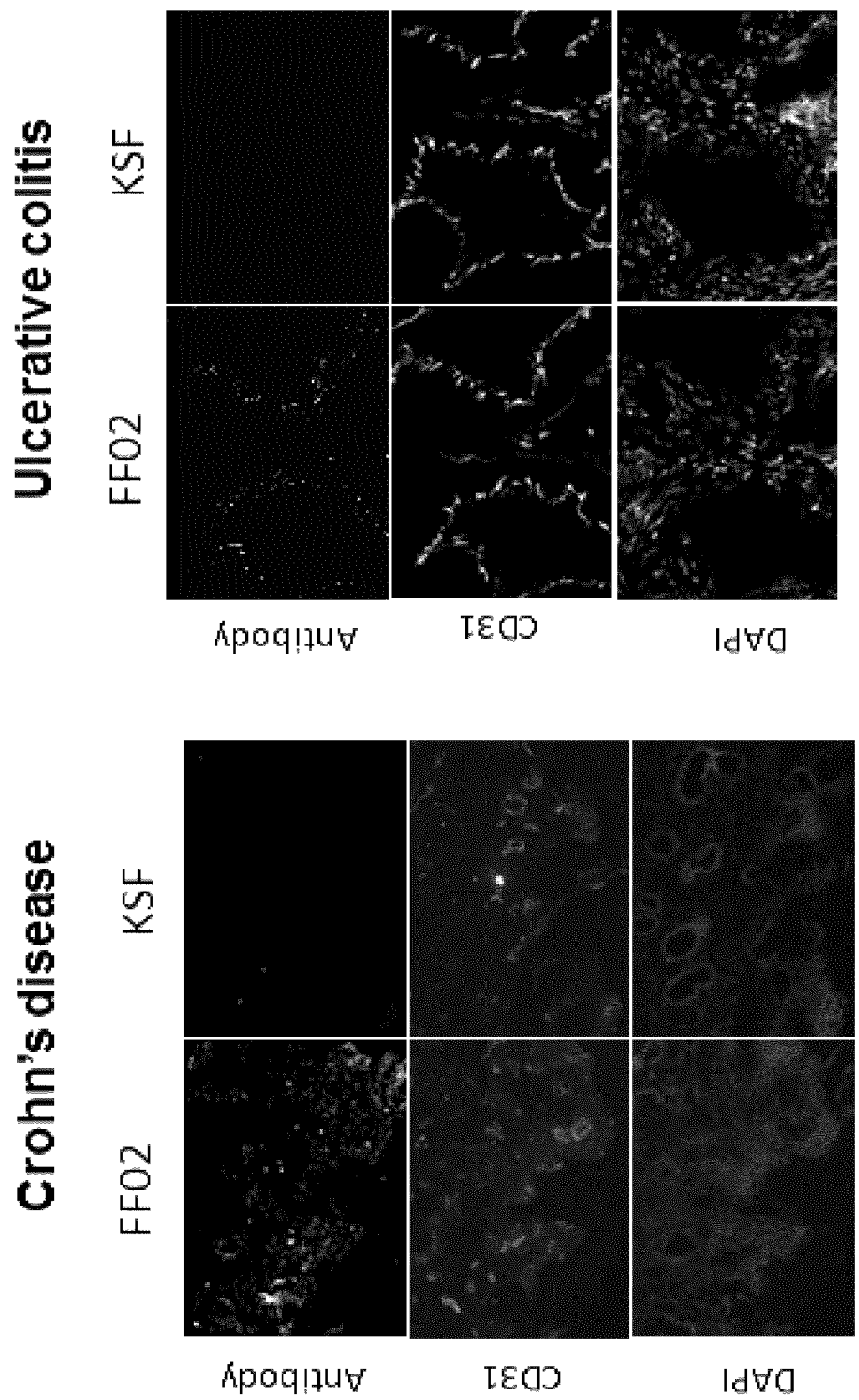
FIG. 7 shows the results of immunofluorescence experiments performed with the FF02 antibody on sections taken from patients with Crohn's disease and ulcerative colitis.

Immunofluorescence Staining of Samples taken from Patients with Ulcerative Colitis or Crohn's Disease with the FF02 Antibody Frozen human colitis and Crohn's disease patient tissue specimens (10 µm sections) were defrosted at room temperate and fixed with ice-cold acetone, and thereafter blocked with 20% FCS in PBS. The slides were first incubated for two hours either with FF02 SIP or with KSF SIP used as negative control, both at a concentration of 5 pg/mL and thereafter revealed with a Rabbit anti-human IgE (1:1000 dilution, Sigma). As positive control a mouse anti-human CD31 antibody (1:200 dilution, eBioscience) was used. The SIP's were detected with and an Alexa488-conjugated goat anti-Rabbit IgG antibody (1:200 dilution, Sigma), and the anti-CD31 antibody was detected with an Alexa 594-conjugated goat anti-mouse IgG (1:200 dilution, Invitrogen). Cells were also counterstained with DAPI (Sigma), and slides were mounted with fluorescent mounting medium (Dako) and analyzed with an Axioskope2 mot plus microscope (Zeiss), using the 20× objective. The results are shown in FIG. 7, and demonstrate that both in ulcerative colitis and in Crohn's disease there was a good correspondence between the staining of the FF02 antibody and the nuclei of the cells as well as the anti-CD31 antibody. No staining was visible for the negative control antibody.

Example 7

Immunofluorescence Staining of Samples from Mice having Colitis with the CPR01.1 Antibody After 2 weeks of acclimatization, 8-week-old specific pathogen-free female C57BL/6 mice (Janvier Labs)

received 3.0% (wt/vol) DSS (40,000 g/mol, TdB Consultancy) in drinking water ad libitum. Five days later, DSS water was replaced by water supplemented with 5% glucose and 0.25% NaHCO₃ for 7 days, followed by nonsupplemented (i.e., normal) water. Body weight and disease score were assessed daily. On day 10 after colitis induction, mice were sacrificed and colon harvested and embedded in O.C.T. compound. Eight micrometers thick sections were cut and stained following a standard immunofluorescence protocol. Briefly, purified antibodies in full IgG format (CPR01.1 and KSF) were added to a final concentration of 2 μg/ml onto the sections. Detection of the primary antibody was performed with a rabbit anti human-IgG (DAKO). Signals were revealed with a goat anti-rabbit Alexa 488. Blood vessels were revealed with a rat anti mouse-CD31 antibody (BD Pharmingen), followed by donkey anti-rat Alexa 594. Counterstaining for cell nuclei was performed with DAPI (eBioscience).

Figure 8A:
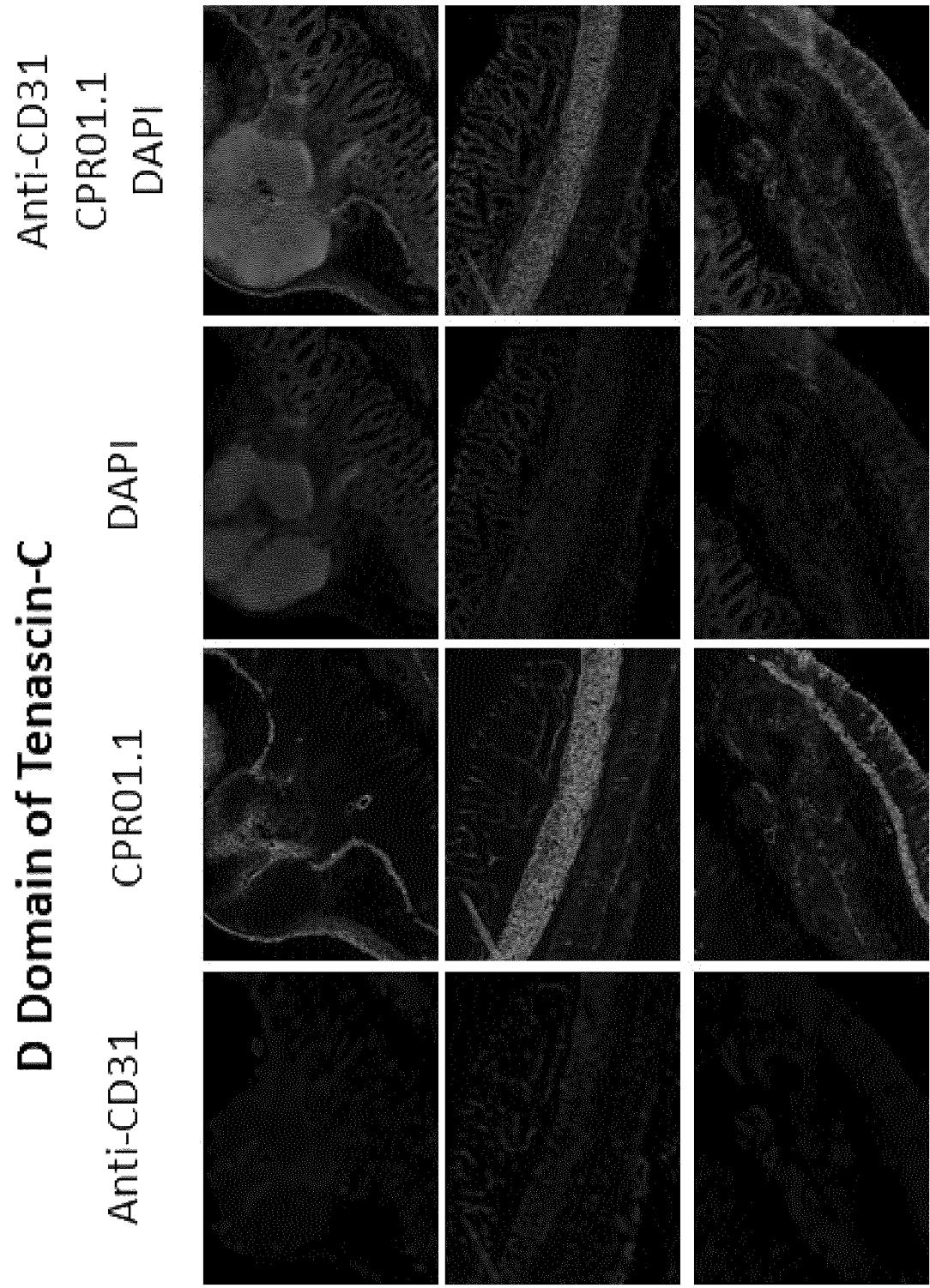
FIG. 8 shows the results of immunofluorescence experiments performed with the CPR01.1 antibody on sections taken from the intestine of a mouse with colitis. A stronger intensity signal can be detected in the colon of animals stained with CPR01.1 (FIG. 8A) when compared to the signal observed with an irrelevant antibody (KSF) (FIG. 8B). An anti-CD31 antibody (specific for an endothelial marker) was used as a positive control. DAPI staining of the nuclei was also performed.
Figure 8B:
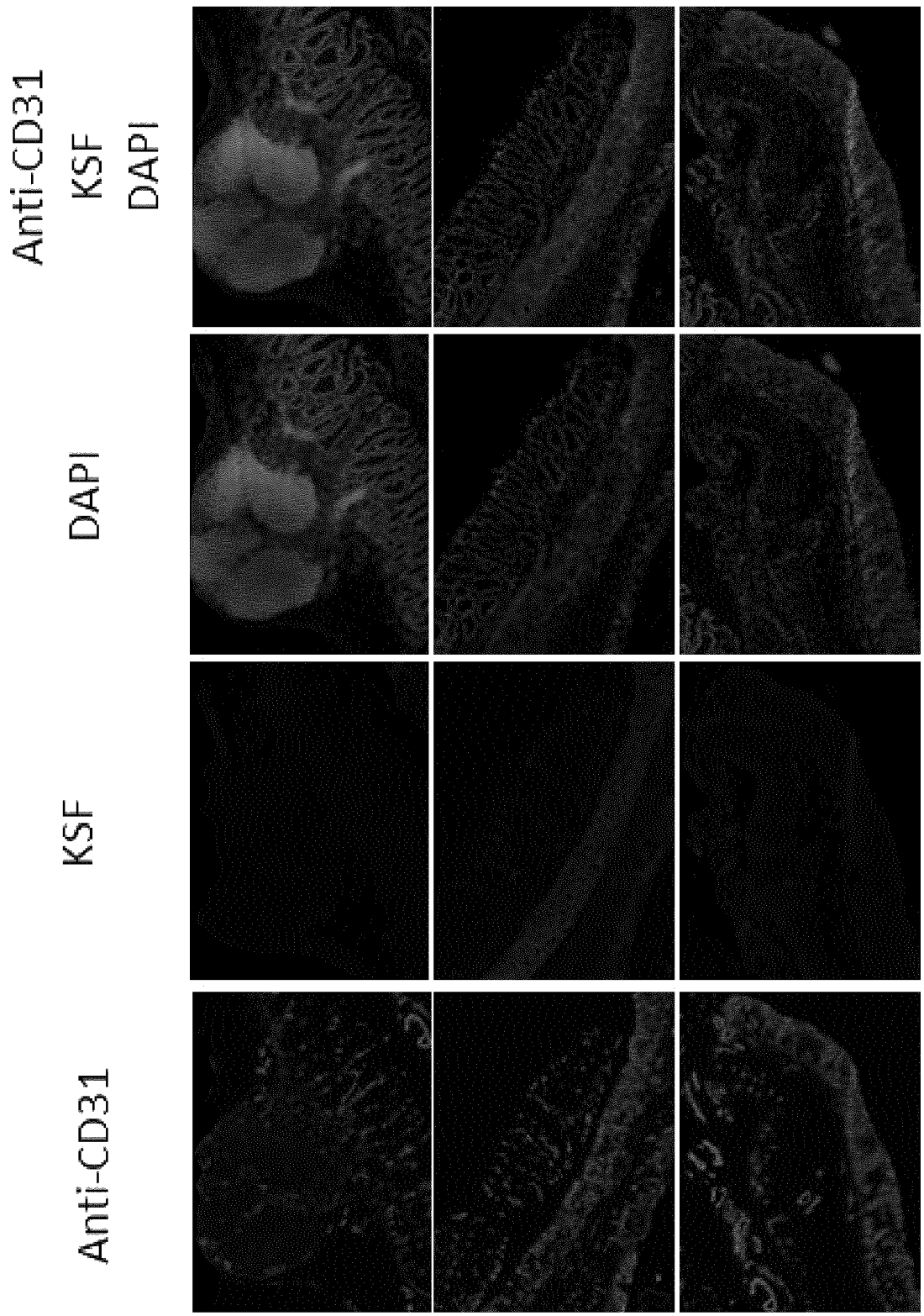

Results:

The results are shown in FIG. 8. A stronger intensity signal can be detected in the colon of animals stained with CPR01.1 when compared to the signal observed with an irrelevant antibody (KSF).

Example 8

In Vivo Targeting Properties of the CPR01.1 Antibody by IVIS Imaging in Mouse Bearing PC3 Xenograph PC-3 cells were purchased from American Type Culture Collection (ATCC) and were grown to 80% confluence and detached with Trypsin-EDTA 0.05% (Life Technologies).

The PC-3 model of human prostatic cancer has been described in Kaighn et al. (1983) Invest. Urol. 17: 16-23. Cells were washed with HBSS medium (Gibco) twice, counted and resuspended in HBSS medium to a final concentration of 100 mio cells ml-1. Aliquots of 5 mio cells (50 μl of a suspension) were mixed 1:1 with Matrigel (Corning Matrigel, 734-1101, VWR) injected subcutaneously in the lower back of Balb/c nude mice (7 weeks of age, Charles River).

In vivo targeting properties of CPR01.1 in IgG format was investigated using near-infrared fluorescence imaging. Mice bearing subcutaneous PC3 tumors were injected intravenously with IRDye 800CW (Licor) labeled CPR01.1 (200 μL). After 72 hours, fluorescence images were acquired on an IVIS Spectrum imaging system. The mouse was then sacrificed by cervical dislocation and images of isolated organs were acquired using the same settings.

Figure 9:
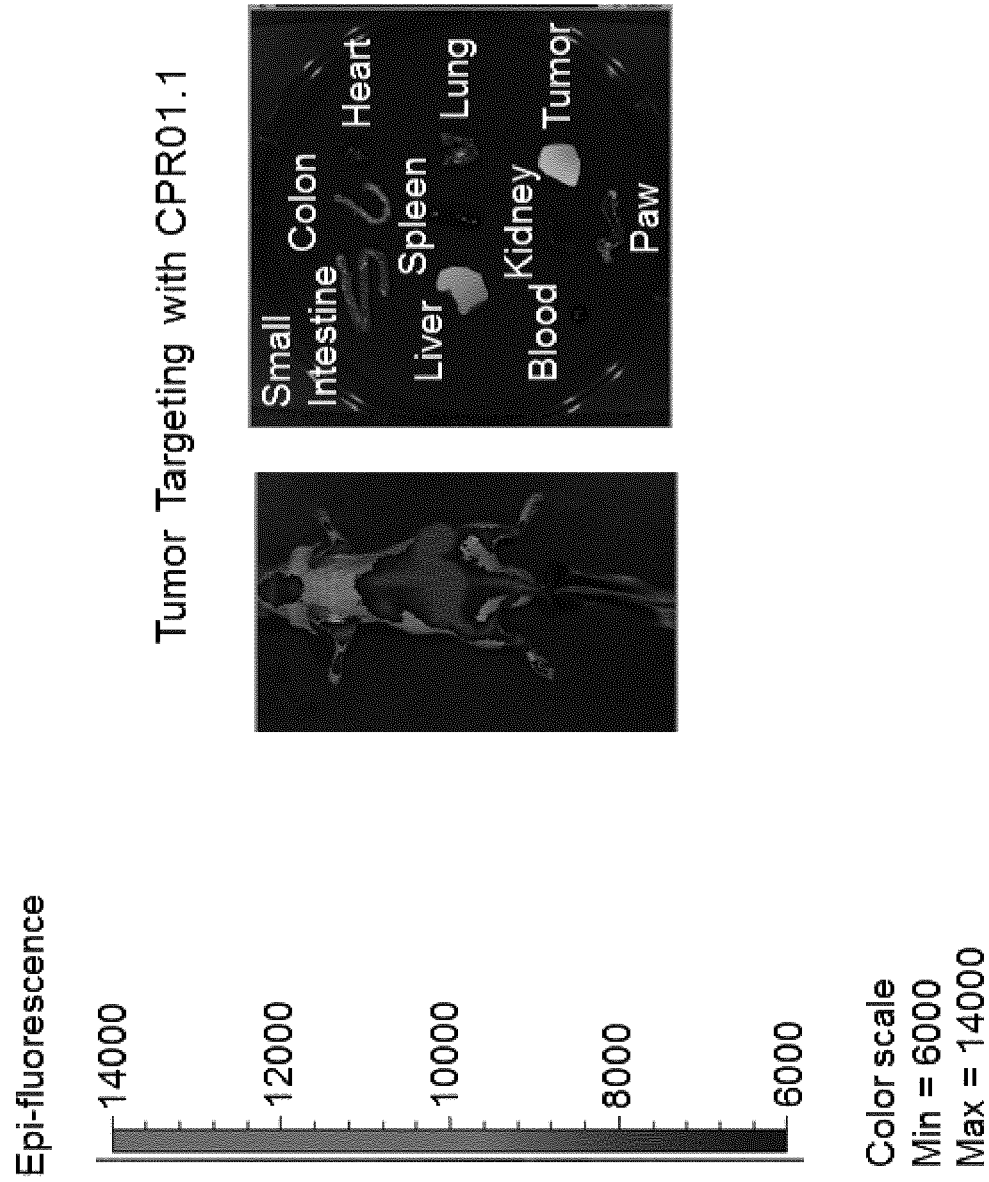
FIG. 9 shows the in vivo near-infrared fluorescence imaging CPR01.1 in mouse bearing PC-3 xenograft. A mouse bearing subcutaneous PC3 tumors was injected intravenously with IRDye 800CW (Licor) labeled CPR01.1 (200 µL). After 72 hours fluorescence images were acquired on an IVIS Spectrum imaging system. The mouse was then sacrificed by cervical dislocation and images of isolated organs were acquired using the same settings. The images show a preferential and selective accumulation CPR01.1 in the tumor. The healthy organs are virtually negative for any uptake of CPR01.1. The signal recorded in the liver is consistent with the expected hepatic excretion route of an IgG labelled with a new-infrared dye.

Results:

The images show a preferential and selective accumulation of CPR01.1 in the tumor. The healthy organs are virtually negative for any uptake of CPR01.1 (FIG. 9). The signal recorded in the liver is consistent with the expected hepatic excretion route of an IgG labelled with a new-infrared dye.

Example 9

Immunofluorescence Staining of Xenograft Tumour Sections with the CPR01.1 Antibody Dual staining for the D domain of tenascin-C and the murine vascular marker CD31 Willebrand factor was performed on sections from the human xenograft melanoma A375, the human xenograft glioblastoma U87 and the murine xenograft teratocarcinoma F9. 10 μm sections from freshly frozen tumour samples were defrosted at room temperate and fixed with ice-cold acetone, rehydrated in PBS and blocked with 3% BSA. Sections were first incubated with affinity-purified SIP formatted antibody fragments (final concentration 5 mg/ml), followed by an anti-Human IgE antibody (DAKO, 2.5 μg/ml final concentration) and the rat anti-Mouse CD31 endothelial marker antibody (BD Pharmigen, 30 ng/mL final concentration). Bound SIPs were detected with a goat anti-rabbit Alexa 488 (Molecular Probes), whilst the CD31 endothelial marker was detected using donkey anti-rat IgG Alexa 594 (Molecular probes). DAPI was used for nuclei staining. The anti-hen egg Lysozyme antibody ScFv(KSF) was used as an isotype-negative control for the staining and the anti-fibronectin EDA domain antibody SIP(F8) (WO2008/120101) was used as a positive control since the presence of the EDA domain in these tissues has previously been confirmed.

Figure 10A:
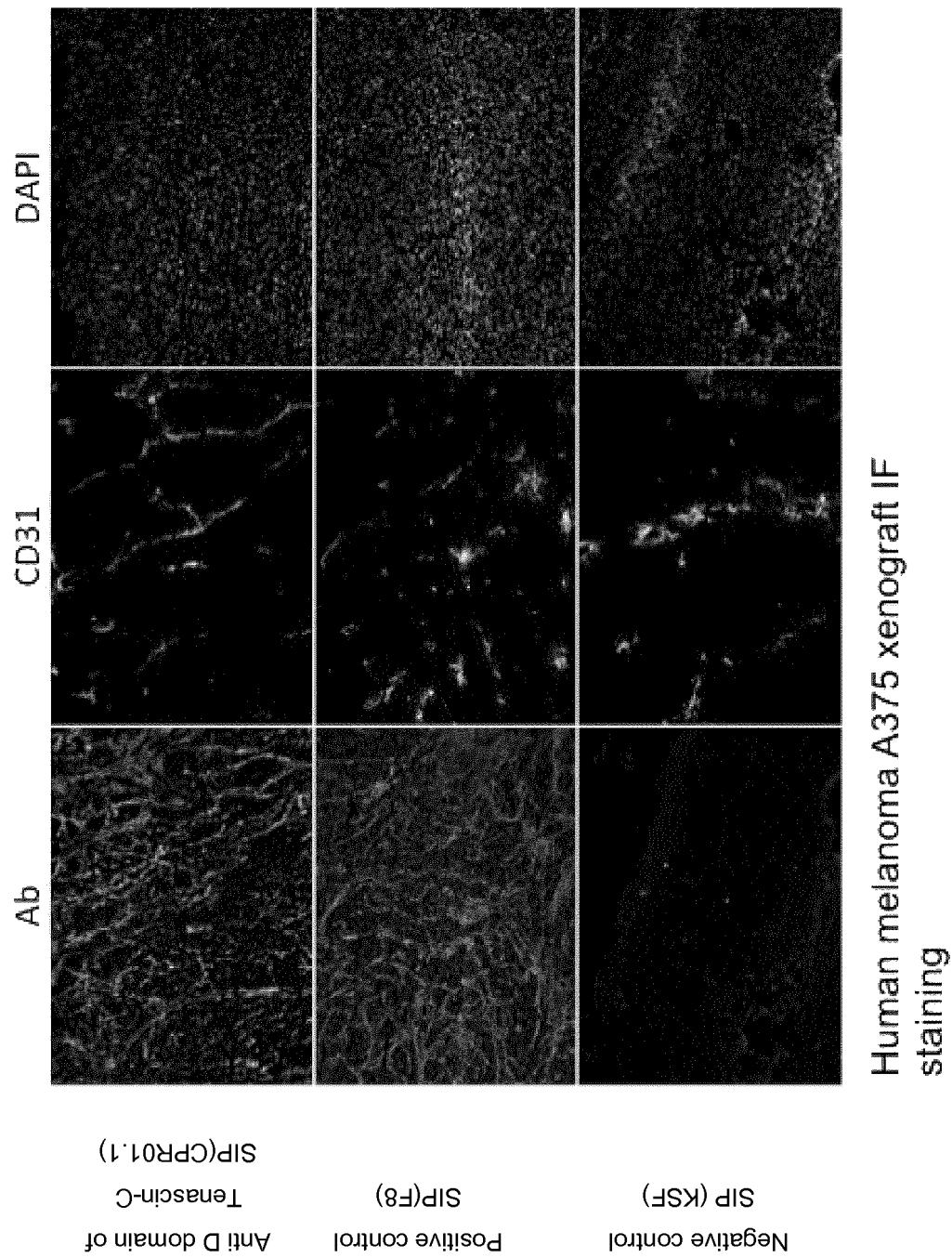
FIG. 10 shows the results of immunofluorescence experiments with the CPR01.1 antibody against the D domain of Tenascin-C on sections from the human xenograft melanoma A375 (FIG. 10A), from the human xenograft glioblastoma U87 (FIG. 10B) and from the murine xenograft teratocarcinoma F9 (FIG. 10C). An anti-CD31 antibody (specific for an endothelial marker) was used as positive control. DAPI staining of the nuclei was also performed. The anti-hen egg Lysozyme antibody ScFv(KSF) was used as an isotype-negative control for the staining and the anti-fibronectin EDA domain antibody SIP(F8) was used as a positive control. The antibody anti-D domain of Tenascin-C SIP (CPR01.1) was able to stain xenograft tumours derived from both murine and human tumour cell lines.
Figure 10B:
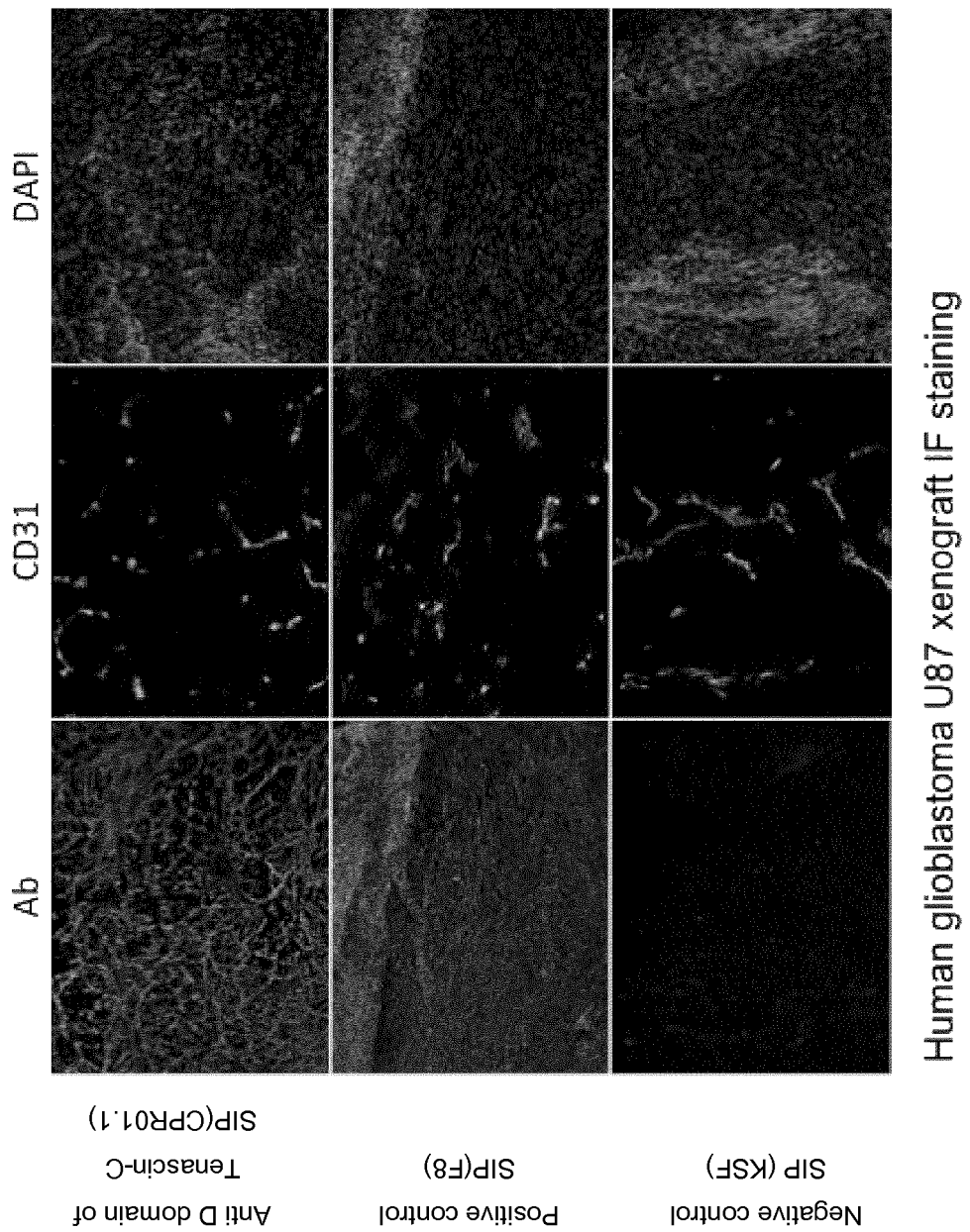
Figure 10C:
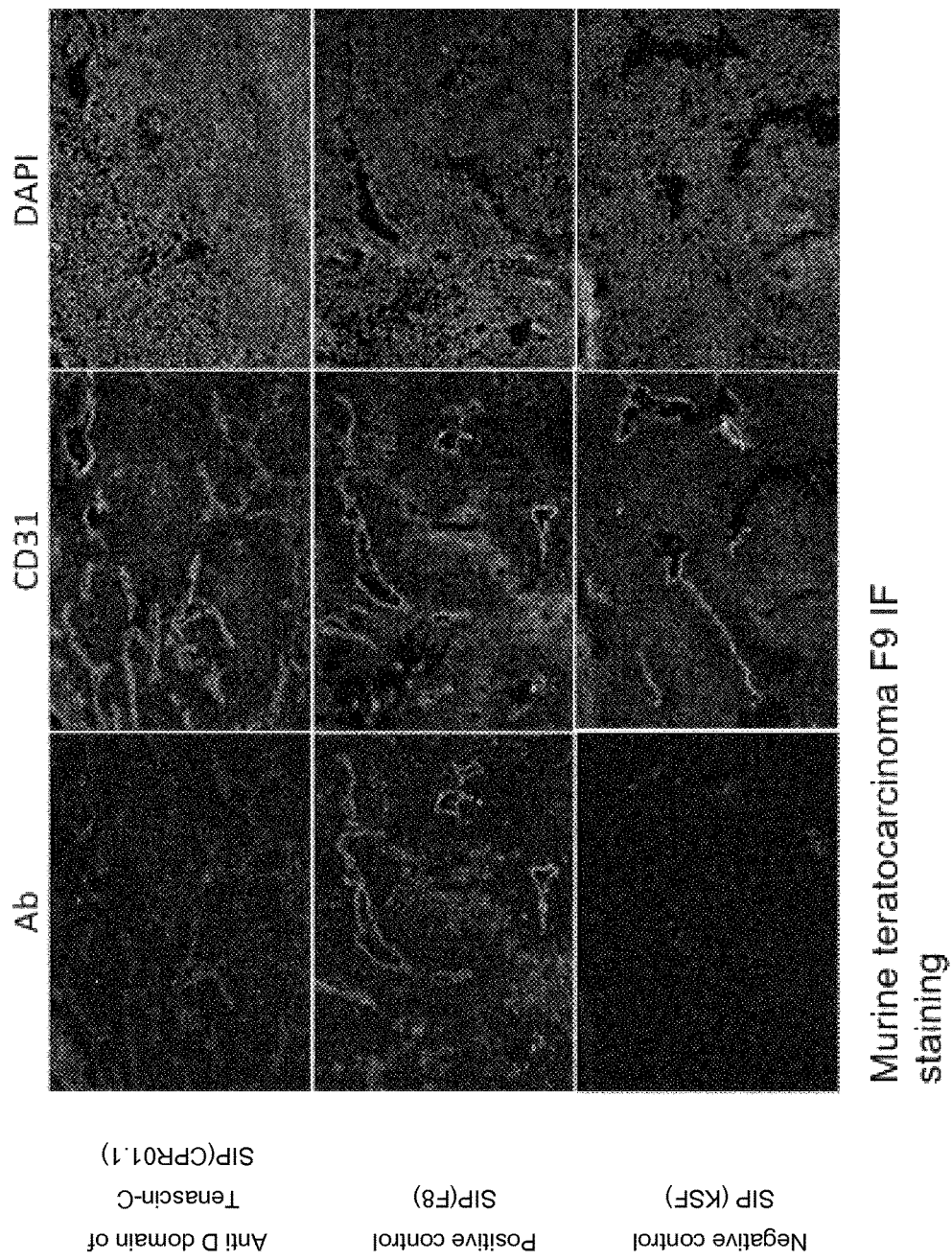

Results:

The antibody anti-D domain of Tenascin-C (CPR01.1) in SIP format was able to stain xenograft tumours derived from both murine and human tumour cell lines (FIG. 10).

SEQUENCE LISTING

Amino Acid Sequences of Antibody CT01 specific for Human Lysozyme

SEQ ID NO: 1
(CT01 - VH)
EVQLLESGGGLVQPGGSLRLSCAASGFTFSSYAMSWVRQAPGKGLEWVSA

ISGSGGSTYYADSVKGRFTISRDNSKNTLYLQMNSLRAEDTAVYYCAKPA

PRARFDYWGQGTLVTVSS

SEQ ID NO: 2
(CT01 - VL)
SSELTQDPAVSVALGQTVRITCQGDSLRSYYASWYQQKPGQAPVLVIYGK

NNRPSGIPDRFSGSSSGNTASLTITGAQAEDEADYYCNSSPTPAPGVVFG

GGTKLTVLG

SEQ ID NO: 3
(CT01 - VH CDR1)
GFTFSSYAMS

SEQ ID NO: 4
(CT01 - VH CDR2)
AISGSGGSTYYADSVKG

SEQ ID NO: 5
(CT01 - VH CDR3)
PAPRARFDY

SEQ ID NO: 6
(CT01 - VL CDR1)
QGDSLRSYYAS

SEQ ID NO: 7
(CT01 - VL CDR2)
GKNNRPS

SEQ ID NO: 8
(CT01 - VL CDR3)
NSSPTPAPGVV

Amino Acid Sequences of Antibody FF01 specific for Human Neutrophil Elastase

SEQ ID NO: 9
(FF01 - VH)
EVQLLESGGGLVQPGGSLRLSCAASGFTFSSYAMSWVRQAPGKGLEWVSA

IKGSGGSTYYADSVKGRFTISRDNSKNTLYLQMNSLRAEDTAVYYCAKVT

WNNYFDYWGQGTLVTVSS

SEQ ID NO: 10
(FF01 - VL)
SSELTQDPAVSVALGQTVRITCQGDSLRSYYASWYQQKPGQAPVLVIYGK

NNRPSGIPDRFSGSSSGNTASLTITGAQAEDEADYYCNSSPDGGRGVVFG

GGTKLTVLG

SEQ ID NO: 85
(FF01 - alternative amino acid sequence of the VL domain)
SSELTQDPAVSVALGQTVRITCQGDSLRSYYASWYQQKPGQAPVLVIYGK

NNRPSGIPDRFSGSSSGNTASLTITGAQAEDEADYYCNSSPDGGRGVVFG

GGTKLTVL

SEQ ID NO: 11
(FF01 - VH CDR1)
GFTFSSYAMS

SEQ ID NO: 12
(FF01 - VH CDR2)
AIKGSGGSTYYADSVKG

SEQ ID NO: 86
(FF01 - alternative amino acid sequence of the VH CDR2)
AIKGSGGSTY

SEQ ID NO: 13
(FF01 - VH CDR3)
VTWNNYFDY

SEQ ID NO: 14
(FF01 - VL CDR1)
QGDSLRSYYAS

SEQ ID NO: 15
(FF01 - VL CDR2)
GKNNRPS

SEQ ID NO: 16
(FF01 - VL CDR3)
NSSPDGGRGVV

Amino Acid Sequences of Antibody 2PC10 specific for Human TIMP-1

SEQ ID NO: 17
(2PC10 - VH)
EVQLLESGGGLVQPGGSLRLSCAASGFTFSSAAMSWVRQAPGKGLEWVSA

ISGSGGSTYYADSVKGRFTISRDNSKNTLYLQMNSLRAEDTAVYYCAKSA

PMFDYWGQGTLVTVSS

SEQ ID NO: 18
(2PC10- VL)
EIVLTQSPGTLSLSPGERATLSCRASQSVSTHLLAWYQQKPGQAPRLLIY

GASSRATGIPDRFSGSGSGTDFTLTISRLEPEDFAVYYCQQWGLTPAMFG

QGTKVEIK

SEQ ID NO: 19
(2PC10 - VH CDR1)
GFTFSSAAMS

SEQ ID NO: 20
(2PC10 - VH CDR2)
AISGSGGSTYYADSVKG

SEQ ID NO: 21
(2PC10 - VH CDR3)
APMFDY

SEQ ID NO: 22
(2PC10 - VL CDR1)
RASQSVSTHLLA

SEQ ID NO: 23
(2PC10 - VL CDR2)
GASSRAT

SEQ ID NO: 24
(2PC10 - VL CDR3)
QQWGLTPAM

Amino Acid Sequences of Antibody CPR01 specific for the D Domain of Human Tenascin-C

SEQ ID NO: 25
(CPR01 - VH)
EVQLLESGGGLVQPGGSLRLSCAASGFTFSSYAMSWVRQAPGKGLEWVSA

IKARGGLTYYADSVKGRFTISRDNSKNTLYLQMNSLRAEDTAVYYCAKGG

APFDYWGQGTLVTVSS

SEQ ID NO: 26
(CPR01 - VL)
SSELTQDPAVSVALGQTVRITCQGDSLRSYYASWYQQKPGQAPVLVIYGK

NNRPSGIPDRFSGSSSGNTASLTITGAQAEDEADYYCNSSPLNRLAVVF

GGGTKLTVLG

SEQ ID NO: 87
(CPR01 - alternative amino acid sequence of the VL domain)
SSELTQDPAVSVALGQTVRITCQGDSLRSYYASWYQQKPGQAPVLVIYGK

NNRPSGIPDRFSGSSSGNTASLTITGAQAEDEADYYCNSSPLNRLAVVFG

GGTKLTVL

SEQ ID NO: 27
(CPR01 - VH CDR1)
GFTFSSYAMS

SEQ ID NO: 28
(CPR01 - VH CDR2)
AIKARGGLTYYADSVKG

SEQ ID NO: 29
(CPR01 - VH CDR3)
GGAPFDY

SEQ ID NO: 30
(CPR01 - VL CDR1)
QGDSLRSYYAS

SEQ ID NO: 31
(CPR01 - VL CDR2)
GKNNRPS

SEQ ID NO: 32
(CPR01 - VL CDR3)
NSSPLNRLAVV

Amino Acid Sequences of Antibody SW01 specific for the IIICS Isoform of Human Fibronectin SEQ ID NO: 33
(SW01 - VH)
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKNR
YIFDYWGQGTLVTVSS SEQ ID NO: 34
(SW01 - VL)
SSELTQDPAVSVALGQTVRITCQGDSLRSYYASWYQQKPGQAPVLVIYGK
NNRPSGIPDRFSGSSSGNTASLTITGAQAEDEADYYCNSSPKAPRPVVFG
GGTKLTVLG

SEQ ID NO: 35
(SW01 - VH CDR1)
GFTFSSYAMS

SEQ ID NO: 36
(SW01 - VH CDR2)
AISGSGGSTYYADSVKG

SEQ ID NO: 37
(SW01 - VH CDR3)
NRYIFDY

SEQ ID NO: 38
(SW01 - VL CDR1)
QGDSLRSYYAS

SEQ ID NO: 39
(SW01 - VL CDR2)
GKNNRPS

SEQ ID NO: 40
(SW01 - VL CDR3)
NSSPKAPRPVV

Amino Acid Sequences of Antibody CH01 specific for Human MMP3

SEQ ID NO: 41
(CH01 - VH)
EVQLLESGGGLVQPGGSLRLSCAASGFTFSPYAMSWVRQAPGKGLEWVSA
ITGQGGVTYYADSVKGRFTISRDNSKNTLYLQMNSLRAEDTAVYYCAKIS
SFHFDYWGQGTLVTVSS

SEQ ID NO: 42
(CH01- VL)
EIVLTQSPGTLSLSPGERATLSCRASQSVSSHHLAWYQQKPGQAPRLLIY
DASSRATGIPDRFSGSGSGTDFTLTISRLEPEDFAVYYCQQPRGAPTTFG
QGTKVEIK

SEQ ID NO: 43
(CH01 - VH CDR1)
GFTFSPYAMS

SEQ ID NO: 44
(CH01 - VH CDR2)
AITGQGGVTYYADSVKG

SEQ ID NO: 45
(CH01 - VH CDR3)
ISSFHFDY

SEQ ID NO: 46
(CH01 - VL CDR1)
RASQSVSSHHLA

SEQ ID NO: 47
(CH01 - VL CDR2)
DASSRAT

SEQ ID NO: 48
(CH01 - VL CDR3)
QQPRGAPTT

Amino Acid Sequences of Antibody L19 specific for the ED-B Domain of Human Fibronectin SEQ ID NO: 49
(L19 - VH)
Glu Val Gln Leu Leu Glu Ser Gly Gly Gly Leu Val
Gln Pro Gly Gly Ser Leu Arg Leu Ser Cys Ala Ala
Ser Gly Phe Thr Phe Ser Ser Phe Ser Met Ser Trp
Val Arg Gln Ala Pro Gly Lys Gly Leu Glu Trp Val
Ser Ser Ile Ser Gly Ser Ser Gly Thr Thr Tyr Tyr
Ala Asp Ser Val Lys Gly Arg Phe Thr Ile Ser Arg
Asp Asn Ser Lys Asn Thr Leu Tyr Leu Gln Met Asn
Ser Leu Arg Ala Glu Asp Thr Ala Val Tyr Tyr Cys
Ala Lys Pro Phe Pro Tyr Phe Asp Tyr Trp Gly Gln
Gly Thr Leu Val Thr Val Ser Ser SEQ ID NO: 50
(L19 - VL)
Glu Ile Val Leu Thr Gln Ser Pro Gly Thr Leu Ser
Leu Ser Pro Gly Glu Arg Ala Thr Leu Ser Cys Arg
Ala Ser Gln Ser Val Ser Ser Ser Phe Leu Ala Trp
Tyr Gln Gln Lys Pro Gly Gln Ala Pro Arg Leu Leu
Ile Tyr Tyr Ala Ser Ser Arg Ala Thr Gly Ile Pro
Asp Arg Phe Ser Gly Ser Gly Ser Gly Thr Asp Phe
Thr Leu Thr Ile Ser Arg Leu Glu Pro Glu Asp Phe
Ala Val Tyr Tyr Cys Gln Gln Thr Gly Arg Ile Pro
Pro Thr Phe Gly Gln Gly Thr Lys Val Glu Ile Lys (SEQ ID NO: 51)
L19 CDR1 VH - Ser Phe Ser Met Ser (SEQ ID NO: 52)
L19 CDR2 VH - Ser Ile Ser Gly Ser Ser Gly Thr Thr Tyr Tyr Ala Asp Ser Val Lys (SEQ ID NO: 53)
L19 CDR3 VH - Pro Phe Pro Tyr Phe Asp Tyr (SEQ ID NO: 54)
L19 CDR1 VL - Arg Ala Ser Gln Ser Val Ser Ser Ser Phe Leu Ala (SEQ ID NO: 55)
L19 CDR2 VL - Tyr Ala Ser Ser Arg Ala Thr (SEQ ID NO: 56)
L19 CDR3 VL - Gln Gln Thr Gly Arg Ile Pro Pro Thr Amino Acid Sequences of Antibody F16 specific for the A1 Domain of Human Tenascin-C (F16 - VH) (SEQ ID NO: 57)
EVQLLESGGGLVQPGGSLRLSCAASGFTFSRYGMSWVRQAPGKGLEWVSA
ISGSGGSTYYADSVKGRFTISRDNSKNTLYLQMNSLRAEDTAVYYCAKAH
NAFDYWGQGTLVTVSR (F16 - VL) (SEQ ID NO: 58)
SSELTQDPAVSVALGQTVRITCQGDSLRSYYASWYQQKPGQAPVLVIYGK
NNRPSGIPDRFSGSSSGNTASLTITGAQAEDEADYYCNSSVYTMPPVVFG
GGTKLTVLG (F16 - alternative amino acid sequence of the VL domain) (SEQ ID NO: 88)
SSELTQDPAVSVALGQTVRITCQGDSLRSYYASWYQQKPGQAPVLVIYGK
NNRPSGIPDRFSGSSSGNTASLTITGAQAEDEADYYCNSSVYTMPPVVFG
GGTKLTVL

F16 CDR1 VH - RYGMS (SEQ ID NO: 59)

F16 CDR2 VH - AISGSGGSTYYADSVKG (SEQ ID NO: 60)

F16 CDR3 VH - AHNAFDY (SEQ ID NO: 61)

F16 CDR1 VL - QGDSLRSYYAS (SEQ ID NO: 62)

F16 CDR2 VL - GKNNRPS (SEQ ID NO: 63)

F16 CDR3 VL - NSSVYTMPPVV (SEQ ID NO: 64)

Amino Acid Sequences of Antibody G11 specific for the C Domain of Human Tenascin-C (G11 - VH) (SEQ ID NO: 65)
EVQLVESGGGLVQPGGSLRLSCAASGFTFSGSRMGWVRQAPGKGLEWVSA
INEEGGQTYYADSVKGRFTISRDNSKNTLYLQMNSLRAEDTAVYYCAKHP
PHRPFDYWGQGTLVTVSR (G11 - VL) (SEQ ID NO: 66)
SSELTQDPAVSVALGQTVRITCQGDSLRLYYASWYQQKPGQAPVLVIYGK
NNRPSGIPDRFSGSSSGNTASLTITGAQAEDEADYYCNSSHGPRRPVVFG
GGTKLTVLG scFv VH-VL domain linker sequence (SEQ ID NO: 67)
GGGGSGGGGSGGGG Diabody VH-VL domain linker sequence (SEQ ID NO: 68)
GGSGG Alternative VH domain sequence for antibody CT01 (SEQ ID NO: 69)
EVQLLESGGGLVQPGGSLRLSCAASGFTFSSYAMSWVRQAPGKGLEWVSA
ISGSGGSTYYADSVKGRFTISRDNSKNTLYLQMNSLRAEDTAVYYCAKPA
PRARFDYWGQGTLVTVS Alternative VH domain sequence for antibody FF01 (SEQ ID NO: 70)
EVQLLESGGGLVQPGGSLRLSCAASGFTFSSYAMSWVRQAPGKGLEWVSA
IKGSGGSTYYADSVKGRFTISRDNSKNTLYLQMNSLRAEDTAVYYCAKVT
WNNYFDYWGQGTLVTVS Alternative VH domain sequence for antibody 2PC10 (SEQ ID NO: 71)
EVQLLESGGGLVQPGGSLRLSCAASGFTFSSAAMSWVRQAPGKGLEWVSA
ISGSGGSTYYADSVKGRFTISRDNSKNTLYLQMNSLRAEDTAVYYCAKSA
PMFDYWGQGTLVTVS Alternative VH domain sequence for antibody CPR01 (SEQ ID NO: 72)
EVQLLESGGGLVQPGGSLRLSCAASGFTFSSYAMSWVRQAPGKGLEWVSA
IKARGGLTYYADSVKGRFTISRDNSKNTLYLQMNSLRAEDTAVYYCAKGG
APFDYWGQGTLVTVS Alternative VL domain sequence for antibody SW01 (SEQ ID NO: 73)
SELTQDPAVSVALGQTVRITCQGDSLRSYYASWYQQKPGQAPVLVIYGKN
NRPSGIPDRFSGSSSGNTASLTITGAQAEDEADYYCNSSPKAPRPVVFGG
GTKLTVLG Amino Acid Sequences of Antibody FF02 specific for Human Neutrophil Elastase (FF02 - VH) (SEQ ID NO: 74)
EVQLLESGGGLVQPGGSLRLSCAASGFTFSSYAMSWVRQAPGKGLEWVSA
IKGSGGSTYYADSVKGRFTISRDNSKNTLYLQMNSLRAEDTAVYYCAKWN
WNLEFDYWGQGTLVTVSS (FF02 - VL) (SEQ ID NO: 75)
SSELTQDPAVSVALGQTVRITCQGDSLRSYYASWYQQKPGQAPVLVIYGK
NNRPSGIPDRFSGSSSGNTASLTITGAQAEDEADYYCNSSGLIWPRVVFG
GGTKLTVLG (FF02 - VH CDR1) (SEQ ID NO: 76)
GFTFSSYAMS (FF02 - VH CDR2) (SEQ ID NO: 77)
AIKGSGGSTYYADSVKG (FF02 - VH CDR3) (SEQ ID NO: 78)
WNWNLEFDY (FF02 - VL CDR1) (SEQ ID NO: 79)
QGDSLRSYYAS (FF02 - VL CDR2) (SEQ ID NO: 80)
GKNNRPS (FF02 - VL CDR3) (SEQ ID NO: 81)
NSSGLIWPRVV SEQ ID NO: 82
(FF02 in SIP format)
The linker linking the VH and VL domains of FF02
is underlined. The sequence linking the VL domain
to the CH4 domain of human IgE is shown in bold
and underlined.
EVQLLESGGGLVQPGGSLRLSCAASGFTFSSYAMSWVRQAPGKGLEWVSA

IKGSGGSTYYADSVKGRFTISRDNSKNTLYLQMNSLRAEDTAVYYCAKWN

WNLEFDYWGQGTLVTVSSGGGGSGGGGSGGGGSSELTQDPAVSVALGQTV

RITCQGDSLRSYYASWYQQKPGQAPVLVIYGKNNRPSGIPDRFSGSSSGN

TASLTITGAQAEDEADYYCNSSGLIWPRVVFGGGTKLTVLGSGGSGGPRA

APEVYAFATPEWPGSRDKRTLACLIQNFMPEDISVQWLHNEVQLPDARHS

TTQPRKTKGSGFFVFSRLEVTRAEWEQKDEFICRAVHEAASPSQTVQRAV

SVNPESSRRGGC

SEQ ID NO: 83
(Linker sequence linking VL domain to CH4 domain
of human IgE)
SGGSG SEQ ID NO: 84
(Amino acid sequence of the CH4 domain of human
IgE)
GPRAAPEVYAFATPEWPGSRDKRTLACLIQNFMPEDISVQWLHNEVQLPD

ARHSTTQPRKTKGSGFFVFSRLEVTRAEWEQKDEFICRAVHEAASPSQTV

QRAVSVNPESSRRGGC

Amino Acid Sequences of Antibody CPR01.1 specific for the D Domain of Human Tenascin-C

SEQ ID NO: 89
(CPR01.1 - VH)
EVQLLESGGGLVQPGGSLRLSCAASGFTFSSYAMSWVRQAPGKGLEWVSA

IKGSGGSTYYADSVKGRFTISRDNSKNTLYLQMNSLRAEDTAVYYCAKGG

APFDYWGQGTLVTVSS

SEQ ID NO: 90
(CPR01.1 - VL)
SSELTQDPAVSVALGQTVRITCQGDSLRSYYASWYQQKPGQAPVLVIYGK

NNRPSGIPDRFSGSSSGNTASLTITGAQAEDEADYYCNSSLRGTLPVVFG

GGTKLTVLG

SEQ ID NO: 27
(CPR01.1 - VH CDR1)
GFTFSSYAMS

SEQ ID NO: 91
(CPR01.1 - VH CDR2)
AIKGSGGSTYYADSVKG

SEQ ID NO: 29
(CPR01.1 - VH CDR3)
GGAPFDY

SEQ ID NO: 30
(CPR01.1 - VL CDR1)
QGDSLRSYYAS

SEQ ID NO: 31
(CPR01.1 - VL CDR2)
GKNNRPS

SEQ ID NO: 92
(CPR01.1 - VL CDR3)
NSSLRGTLPVV

SEQ ID NO: 93
(CPR01.1, Full ScFv sequence)
EVQLLESGGGLVQPGGSLRLSCAASGFTFSSYAMSWVRQAPGKGLEWVSA

IKGSGGSTYYADSVKGRFTISRDNSKNTLYLQMNSLRAEDTAVYYCAKGG

APFDYWGQGTLVTVSSGGGGSGGGGSGGGGSSELTQDPAVSVALGQTVRI

TCQGDSLRSYYASWYQQKPGQAPVLVIYGKNNRPSGIPDRFSGSSSGNTA

SLTITGAQAEDEADYYCNSSLRGTLPVVFGGGTKLTVLG

---

The invention claimed is:

1. An antibody molecule that binds domain D of Tenascin-C, wherein the antibody molecule comprises a VH domain comprising a framework and a set of complementarity determining regions HCDR1, HCDR2 and HCDR3, and a VL domain comprising a framework and a set of complementarity determining regions LCDR1, LCDR2 and LCDR3, wherein:
   HCDR1 has the amino acid sequence of SEQ ID NO: 27;
   HCDR2 has the amino acid sequence of SEQ ID NO: 91;
   HCDR3 has the amino acid sequence of SEQ ID NO: 29;
   LCDR1 has the amino acid sequence of SEQ ID NO: 30;
   LCDR2 has the amino acid sequence of SEQ ID NO: 31; and
   LCDR3 has the amino acid sequence of SEQ ID NO: 92.

2. The antibody molecule according to claim 1, wherein the VH domain comprises or consist of the amino acid sequence of SEQ ID NO: 89, and/or the VL domain comprises or consist of the amino acid sequence of SEQ ID NO: 90.

3. The antibody molecule according to claim 1 wherein the antibody molecule is or comprises a single chain Fv (scFv), is a small immunoprotein (SIP), is a diabody, or is an IgG molecule.

4. A conjugate comprising an antibody molecule according to claim 1 and an immunosuppressive or anti-inflammatory agent.

5. The conjugate according to claim 4, wherein the anti-inflammatory agent is a cytokine.

6. The conjugate according to claim 4 wherein the conjugate is a fusion protein comprising the antibody molecule and an immunosuppressive agent, an anti-inflammatory agent, or a cytokine.

7. A conjugate comprising an antibody molecule according to claim 1 and a detectable label.

* * * * *

SEQUENCE LISTING

```
<160> NUMBER OF SEQ ID NOS: 93

<210> SEQ ID NO 1
<211> LENGTH: 118
<212> TYPE: PRT
<213> ORGANISM: Artificial Sequence
<220> FEATURE:
<223> OTHER INFORMATION: CT-01 - VH

<400> SEQUENCE: 1
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

```
Ala Lys Pro Ala Pro Arg Ala Arg Phe Asp Tyr Trp Gly Gln Gly Thr
            100                 105                 110

Leu Val Thr Val Ser Ser
        115

<210> SEQ ID NO 2
<211> LENGTH: 109
<212> TYPE: PRT
<213> ORGANISM: Artificial Sequence
<220> FEATURE:
<223> OTHER INFORMATION: CT01 - VL

<400> SEQUENCE: 2

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Thr Pro Ala Pro Gly
                85                  90                  95

Val Val Phe Gly Gly Gly Thr Lys Leu Thr Val Leu Gly
            100                 105

<210> SEQ ID NO 3
<211> LENGTH: 10
<212> TYPE: PRT
<213> ORGANISM: Artificial Sequence
<220> FEATURE:
<223> OTHER INFORMATION: CT-01 VH CDR1

<400> SEQUENCE: 3

Gly Phe Thr Phe Ser Ser Tyr Ala Met Ser
1               5                   10

<210> SEQ ID NO 4
<211> LENGTH: 17
<212> TYPE: PRT
<213> ORGANISM: Artificial Sequence
<220> FEATURE:
<223> OTHER INFORMATION: CT01 - VH CDR2

<400> SEQUENCE: 4

Ala Ile Ser Gly Ser Gly Gly Ser Thr Tyr Tyr Ala Asp Ser Val Lys
1               5                   10                  15

Gly

<210> SEQ ID NO 5
<211> LENGTH: 9
<212> TYPE: PRT
<213> ORGANISM: Artificial Sequence
<220> FEATURE:
<223> OTHER INFORMATION: CT01 - VH CDR3

<400> SEQUENCE: 5

Pro Ala Pro Arg Ala Arg Phe Asp Tyr
1               5
```

```
<210> SEQ ID NO 6
<211> LENGTH: 11
<212> TYPE: PRT
<213> ORGANISM: Artificial Sequence
<220> FEATURE:
<223> OTHER INFORMATION: CT01 - VL CDR1

<400> SEQUENCE: 6

Gln Gly Asp Ser Leu Arg Ser Tyr Tyr Ala Ser
1               5                   10

<210> SEQ ID NO 7
<211> LENGTH: 7
<212> TYPE: PRT
<213> ORGANISM: Artificial Sequence
<220> FEATURE:
<223> OTHER INFORMATION: CT01 - VL CDR2

<400> SEQUENCE: 7

Gly Lys Asn Asn Arg Pro Ser
1               5

<210> SEQ ID NO 8
<211> LENGTH: 11
<212> TYPE: PRT
<213> ORGANISM: Artificial Sequence
<220> FEATURE:
<223> OTHER INFORMATION: CT01 - VL CDR3

<400> SEQUENCE: 8

Asn Ser Ser Pro Thr Pro Ala Pro Gly Val Val
1               5                   10

<210> SEQ ID NO 9
<211> LENGTH: 118
<212> TYPE: PRT
<213> ORGANISM: Artificial Sequence
<220> FEATURE:
<223> OTHER INFORMATION: FF01 - VH

<400> SEQUENCE: 9

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Trp Asn Asn Tyr Phe Asp Tyr Trp Gly Gln Gly Thr
            100                 105                 110

Leu Val Thr Val Ser Ser
        115

<210> SEQ ID NO 10
<211> LENGTH: 109
<212> TYPE: PRT
<213> ORGANISM: Artificial Sequence
<220> FEATURE:
```

<223> OTHER INFORMATION: FF01 - VL

<400> SEQUENCE: 10

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Asp Gly Gly Arg Gly
                85                  90                  95

Val Val Phe Gly Gly Gly Thr Lys Leu Thr Val Leu Gly
            100                 105

<210> SEQ ID NO 11
<211> LENGTH: 10
<212> TYPE: PRT
<213> ORGANISM: Artificial Sequence
<220> FEATURE:
<223> OTHER INFORMATION: FF01 - VH CDR1

<400> SEQUENCE: 11

Gly Phe Thr Phe Ser Ser Tyr Ala Met Ser
1               5                   10

<210> SEQ ID NO 12
<211> LENGTH: 17
<212> TYPE: PRT
<213> ORGANISM: Artificial Sequence
<220> FEATURE:
<223> OTHER INFORMATION: FF01 - VH CDR2

<400> SEQUENCE: 12

Ala Ile Lys Gly Ser Gly Gly Ser Thr Tyr Tyr Ala Asp Ser Val Lys
1               5                   10                  15

Gly

<210> SEQ ID NO 13
<211> LENGTH: 9
<212> TYPE: PRT
<213> ORGANISM: Artificial Sequence
<220> FEATURE:
<223> OTHER INFORMATION: FF01 - VH CDR3

<400> SEQUENCE: 13

Val Thr Trp Asn Asn Tyr Phe Asp Tyr
1               5

<210> SEQ ID NO 14
<211> LENGTH: 11
<212> TYPE: PRT
<213> ORGANISM: Artificial Sequence
<220> FEATURE:
<223> OTHER INFORMATION: FF01 - VL CDR1

<400> SEQUENCE: 14

Gln Gly Asp Ser Leu Arg Ser Tyr Tyr Ala Ser
1               5                   10

<210> SEQ ID NO 15
<211> LENGTH: 7
<212> TYPE: PRT
<213> ORGANISM: Artificial Sequence
<220> FEATURE:
<223> OTHER INFORMATION: FF01 - VL CDR2

<400> SEQUENCE: 15

Gly Lys Asn Asn Arg Pro Ser
1               5

<210> SEQ ID NO 16
<211> LENGTH: 11
<212> TYPE: PRT
<213> ORGANISM: Artificial Sequence
<220> FEATURE:
<223> OTHER INFORMATION: FF01 - VL CDR3

<400> SEQUENCE: 16

Asn Ser Ser Pro Asp Gly Gly Arg Gly Val Val
1               5                   10

<210> SEQ ID NO 17
<211> LENGTH: 116
<212> TYPE: PRT
<213> ORGANISM: Artificial Sequence
<220> FEATURE:
<223> OTHER INFORMATION: 2PC10 - VH

<400> SEQUENCE: 17

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Pro Met Phe Asp Tyr Trp Gly Gln Gly Thr Leu Val
            100                 105                 110

Thr Val Ser Ser
        115

<210> SEQ ID NO 18
<211> LENGTH: 108
<212> TYPE: PRT
<213> ORGANISM: Artificial Sequence
<220> FEATURE:
<223> OTHER INFORMATION: 2PC10 - VL

<400> SEQUENCE: 18

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Thr His
            20                  25                  30

Leu Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Trp Gly Leu Thr Pro
                 85                  90                  95

Ala Met Phe Gly Gln Gly Thr Lys Val Glu Ile Lys
                100                 105

<210> SEQ ID NO 19
<211> LENGTH: 10
<212> TYPE: PRT
<213> ORGANISM: Artificial Sequence
<220> FEATURE:
<223> OTHER INFORMATION: 2PC10 - VH CDR1

<400> SEQUENCE: 19

Gly Phe Thr Phe Ser Ser Ala Ala Met Ser
1               5                   10

<210> SEQ ID NO 20
<211> LENGTH: 17
<212> TYPE: PRT
<213> ORGANISM: Artificial Sequence
<220> FEATURE:
<223> OTHER INFORMATION: 2PC10 - VH CDR2

<400> SEQUENCE: 20

Ala Ile Ser Gly Ser Gly Gly Ser Thr Tyr Tyr Ala Asp Ser Val Lys
1               5                   10                  15

Gly

<210> SEQ ID NO 21
<211> LENGTH: 6
<212> TYPE: PRT
<213> ORGANISM: Artificial Sequence
<220> FEATURE:
<223> OTHER INFORMATION: 2PC10 - VH CDR3

<400> SEQUENCE: 21

Ala Pro Met Phe Asp Tyr
1               5

<210> SEQ ID NO 22
<211> LENGTH: 12
<212> TYPE: PRT
<213> ORGANISM: Artificial Sequence
<220> FEATURE:
<223> OTHER INFORMATION: 2PC10 - VL CDR1

<400> SEQUENCE: 22

Arg Ala Ser Gln Ser Val Ser Thr His Leu Leu Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: 2PC10 - VL CDR2

<400> SEQUENCE: 23

Gly Ala Ser Ser Arg Ala Thr
1               5
```

```
<210> SEQ ID NO 24
<211> LENGTH: 9
<212> TYPE: PRT
<213> ORGANISM: Artificial Sequence
<220> FEATURE:
<223> OTHER INFORMATION: 2PC10 - VL CDR3

<400> SEQUENCE: 24

Gln Gln Trp Gly Leu Thr Pro Ala Met
1               5

<210> SEQ ID NO 25
<211> LENGTH: 116
<212> TYPE: PRT
<213> ORGANISM: Artificial Sequence
<220> FEATURE:
<223> OTHER INFORMATION: CPR01 - VH

<400> SEQUENCE: 25

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Ala Arg Gly Gly Leu Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ala Pro Phe Asp Tyr Trp Gly Gln Gly Thr Leu Val
            100                 105                 110

Thr Val Ser Ser
        115

<210> SEQ ID NO 26
<211> LENGTH: 109
<212> TYPE: PRT
<213> ORGANISM: Artificial Sequence
<220> FEATURE:
<223> OTHER INFORMATION: CPR01 - VL

<400> SEQUENCE: 26

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Leu Asn Arg Leu Ala
                85                  90                  95

Val Val Phe Gly Gly Gly Thr Lys Leu Thr Val Leu Gly
            100                 105
```

```
<210> SEQ ID NO 27
<211> LENGTH: 10
<212> TYPE: PRT
<213> ORGANISM: Artificial Sequence
<220> FEATURE:
<223> OTHER INFORMATION: CPR01 - VH CDR1

<400> SEQUENCE: 27

Gly Phe Thr Phe Ser Ser Tyr Ala Met Ser
1               5                   10

<210> SEQ ID NO 28
<211> LENGTH: 17
<212> TYPE: PRT
<213> ORGANISM: Artificial Sequence
<220> FEATURE:
<223> OTHER INFORMATION: CPR01 - VH CDR2

<400> SEQUENCE: 28

Ala Ile Lys Ala Arg Gly Gly Leu Thr Tyr Tyr Ala Asp Ser Val Lys
1               5                   10                  15
Gly

<210> SEQ ID NO 29
<211> LENGTH: 7
<212> TYPE: PRT
<213> ORGANISM: Artificial Sequence
<220> FEATURE:
<223> OTHER INFORMATION: CPR01 - VH CDR3

<400> SEQUENCE: 29

Gly Gly Ala Pro Phe Asp Tyr
1               5

<210> SEQ ID NO 30
<211> LENGTH: 11
<212> TYPE: PRT
<213> ORGANISM: Artificial Sequence
<220> FEATURE:
<223> OTHER INFORMATION: CPR01 - VL CDR1

<400> SEQUENCE: 30

Gln Gly Asp Ser Leu Arg Ser Tyr Tyr Ala Ser
1               5                   10

<210> SEQ ID NO 31
<211> LENGTH: 7
<212> TYPE: PRT
<213> ORGANISM: Artificial Sequence
<220> FEATURE:
<223> OTHER INFORMATION: CPR01 - VL CDR2

<400> SEQUENCE: 31

Gly Lys Asn Asn Arg Pro Ser
1               5

<210> SEQ ID NO 32
<211> LENGTH: 11
<212> TYPE: PRT
<213> ORGANISM: Artificial Sequence
<220> FEATURE:
<223> OTHER INFORMATION: CPR01 - VL CDR3

<400> SEQUENCE: 32

Asn Ser Ser Pro Leu Asn Arg Leu Ala Val Val
1               5                   10
```

```
<210> SEQ ID NO 33
<211> LENGTH: 116
<212> TYPE: PRT
<213> ORGANISM: Artificial Sequence
<220> FEATURE:
<223> OTHER INFORMATION: SW01 - VH

<400> SEQUENCE: 33

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Arg Tyr Ile Phe Asp Tyr Trp Gly Gln Gly Thr Leu Val
            100                 105                 110

Thr Val Ser Ser
        115

<210> SEQ ID NO 34
<211> LENGTH: 109
<212> TYPE: PRT
<213> ORGANISM: Artificial Sequence
<220> FEATURE:
<223> OTHER INFORMATION: SW01 - VL

<400> SEQUENCE: 34

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Lys Ala Pro Arg Pro
                85                  90                  95

Val Val Phe Gly Gly Gly Thr Lys Leu Thr Val Leu Gly
            100                 105

<210> SEQ ID NO 35
<211> LENGTH: 10
<212> TYPE: PRT
<213> ORGANISM: Artificial Sequence
<220> FEATURE:
<223> OTHER INFORMATION: SW01 - VH CDR1

<400> SEQUENCE: 35

Gly Phe Thr Phe Ser Ser Tyr Ala Met Ser
1               5                   10
```

```
<210> SEQ ID NO 36
<211> LENGTH: 17
<212> TYPE: PRT
<213> ORGANISM: Artificial Sequence
<220> FEATURE:
<223> OTHER INFORMATION: SW01 VH CDR2

<400> SEQUENCE: 36

Ala Ile Ser Gly Ser Gly Gly Ser Thr Tyr Tyr Ala Asp Ser Val Lys
1               5                   10                  15
Gly

<210> SEQ ID NO 37
<211> LENGTH: 7
<212> TYPE: PRT
<213> ORGANISM: Artificial Sequence
<220> FEATURE:
<223> OTHER INFORMATION: SW01 - VH CDR3

<400> SEQUENCE: 37

Asn Arg Tyr Ile Phe Asp Tyr
1               5

<210> SEQ ID NO 38
<211> LENGTH: 11
<212> TYPE: PRT
<213> ORGANISM: Artificial Sequence
<220> FEATURE:
<223> OTHER INFORMATION: SW01 - VL CDR1

<400> SEQUENCE: 38

Gln Gly Asp Ser Leu Arg Ser Tyr Tyr Ala Ser
1               5                   10

<210> SEQ ID NO 39
<211> LENGTH: 7
<212> TYPE: PRT
<213> ORGANISM: Artificial Sequence
<220> FEATURE:
<223> OTHER INFORMATION: SW01 - VL CDR2

<400> SEQUENCE: 39

Gly Lys Asn Asn Arg Pro Ser
1               5

<210> SEQ ID NO 40
<211> LENGTH: 11
<212> TYPE: PRT
<213> ORGANISM: Artificial Sequence
<220> FEATURE:
<223> OTHER INFORMATION: SW01 - VL CDR3

<400> SEQUENCE: 40

Asn Ser Ser Pro Lys Ala Pro Arg Pro Val Val
1               5                   10

<210> SEQ ID NO 41
<211> LENGTH: 117
<212> TYPE: PRT
<213> ORGANISM: Artificial Sequence
<220> FEATURE:
<223> OTHER INFORMATION: CH01 - VH

<400> SEQUENCE: 41

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Ser Pro Tyr
            20                  25                  30

Ala Met Ser Trp Val Arg Gln Ala Pro Gly Lys Gly Leu Glu Trp Val
        35                  40                  45

Ser Ala Ile Thr Gly Gln Gly Gly Val Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ile Ser Ser Phe His Phe Asp Tyr Trp Gly Gln Gly Thr Leu
            100                 105                 110

Val Thr Val Ser Ser
        115

<210> SEQ ID NO 42
<211> LENGTH: 108
<212> TYPE: PRT
<213> ORGANISM: Artificial Sequence
<220> FEATURE:
<223> OTHER INFORMATION: CH01 - VL

<400> SEQUENCE: 42

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser His
            20                  25                  30

His Leu Ala Trp Tyr Gln Gln Lys Pro Gly Gln Ala Pro Arg Leu Leu
        35                  40                  45

Ile Tyr Asp Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Pro Arg Gly Ala Pro
                85                  90                  95

Thr Thr Phe Gly Gln Gly Thr Lys Val Glu Ile Lys
            100                 105

<210> SEQ ID NO 43
<211> LENGTH: 10
<212> TYPE: PRT
<213> ORGANISM: Artificial Sequence
<220> FEATURE:
<223> OTHER INFORMATION: CH01 - VH CDR1

<400> SEQUENCE: 43

Gly Phe Thr Phe Ser Pro Tyr Ala Met Ser
1               5                   10

<210> SEQ ID NO 44
<211> LENGTH: 17
<212> TYPE: PRT
<213> ORGANISM: Artificial Sequence
<220> FEATURE:
<223> OTHER INFORMATION: CH01 - VH CDR2

<400> SEQUENCE: 44

Ala Ile Thr Gly Gln Gly Gly Val Thr Tyr Tyr Ala Asp Ser Val Lys
1               5                   10                  15

Gly

<210> SEQ ID NO 45
<211> LENGTH: 8
<212> TYPE: PRT
<213> ORGANISM: Artificial Sequence
<220> FEATURE:
<223> OTHER INFORMATION: CH01 - VH CDR3

<400> SEQUENCE: 45

Ile Ser Ser Phe His Phe Asp Tyr
1               5

<210> SEQ ID NO 46
<211> LENGTH: 12
<212> TYPE: PRT
<213> ORGANISM: Artificial Sequence
<220> FEATURE:
<223> OTHER INFORMATION: CH01 - VL CDR1

<400> SEQUENCE: 46

Arg Ala Ser Gln Ser Val Ser Ser His His Leu Ala
1               5                   10

<210> SEQ ID NO 47
<211> LENGTH: 7
<212> TYPE: PRT
<213> ORGANISM: Artificial Sequence
<220> FEATURE:
<223> OTHER INFORMATION: CH01 - VL CDR2

<400> SEQUENCE: 47

Asp Ala Ser Ser Arg Ala Thr
1               5

<210> SEQ ID NO 48
<211> LENGTH: 9
<212> TYPE: PRT
<213> ORGANISM: Artificial Sequence
<220> FEATURE:
<223> OTHER INFORMATION: CH01 - VL CDR3

<400> SEQUENCE: 48

Gln Gln Pro Arg Gly Ala Pro Thr Thr
1               5

<210> SEQ ID NO 49
<211> LENGTH: 116
<212> TYPE: PRT
<213> ORGANISM: Artificial Sequence
<220> FEATURE:
<223> OTHER INFORMATION: L19 - VH

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Lys Pro Phe Pro Tyr Phe Asp Tyr Trp Gly Gln Gly Thr Leu Val
            100                 105                 110

Thr Val Ser Ser
        115

<210> SEQ ID NO 50
<211> LENGTH: 108
<212> TYPE: PRT
<213> ORGANISM: Artificial Sequence
<220> FEATURE:
<223> OTHER INFORMATION: L19 - VL

<400> SEQUENCE: 50

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile Lys
            100                 105

<210> SEQ ID NO 51
<211> LENGTH: 5
<212> TYPE: PRT
<213> ORGANISM: Artificial Sequence
<220> FEATURE:
<223> OTHER INFORMATION: L19 CDR1 VH

<400> SEQUENCE: 51

Ser Phe Ser Met Ser
1               5

<210> SEQ ID NO 52
<211> LENGTH: 16
<212> TYPE: PRT
<213> ORGANISM: Artificial Sequence
<220> FEATURE:
<223> OTHER INFORMATION: L19 CDR2 VH

<400> SEQUENCE: 52

Ser Ile Ser Gly Ser Ser Gly Thr Thr Tyr Tyr Ala Asp Ser Val Lys
1               5                   10                  15

<210> SEQ ID NO 53
<211> LENGTH: 7
<212> TYPE: PRT
<213> ORGANISM: Artificial Sequence
<220> FEATURE:
<223> OTHER INFORMATION: L19 CDR3 VH

<400> SEQUENCE: 53

Pro Phe Pro Tyr Phe Asp Tyr
1               5
```

```
<210> SEQ ID NO 54
<211> LENGTH: 12
<212> TYPE: PRT
<213> ORGANISM: Artificial Sequence
<220> FEATURE:
<223> OTHER INFORMATION: L19 CDR1 VL

<400> SEQUENCE: 54

Arg Ala Ser Gln Ser Val Ser Ser Ser Phe Leu Ala
1               5                   10

<210> SEQ ID NO 55
<211> LENGTH: 7
<212> TYPE: PRT
<213> ORGANISM: Artificial Sequence
<220> FEATURE:
<223> OTHER INFORMATION: L19 CDR2 VL

<400> SEQUENCE: 55

Tyr Ala Ser Ser Arg Ala Thr
1               5

<210> SEQ ID NO 56
<211> LENGTH: 9
<212> TYPE: PRT
<213> ORGANISM: Artificial Sequence
<220> FEATURE:
<223> OTHER INFORMATION: L19 CDR3 VL

<400> SEQUENCE: 56

Gln Gln Thr Gly Arg Ile Pro Pro Thr
1               5

<210> SEQ ID NO 57
<211> LENGTH: 116
<212> TYPE: PRT
<213> ORGANISM: Artificial Sequence
<220> FEATURE:
<223> OTHER INFORMATION: F16 - VH

<400> SEQUENCE: 57

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Arg Tyr
            20                  25                  30

Gly Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala His Asn Ala Phe Asp Tyr Trp Gly Gln Gly Thr Leu Val
            100                 105                 110

Thr Val Ser Arg
        115

<210> SEQ ID NO 58
<211> LENGTH: 109
<212> TYPE: PRT
<213> ORGANISM: Artificial Sequence
<220> FEATURE:
<223> OTHER INFORMATION: F16  - VL
```

<400> SEQUENCE: 58

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu Gly
            100                 105

<210> SEQ ID NO 59
<211> LENGTH: 5
<212> TYPE: PRT
<213> ORGANISM: Artificial Sequence
<220> FEATURE:
<223> OTHER INFORMATION: F16 CDR1 VH

<400> SEQUENCE: 59

Arg Tyr Gly Met Ser
1               5

<210> SEQ ID NO 60
<211> LENGTH: 17
<212> TYPE: PRT
<213> ORGANISM: Artificial Sequence
<220> FEATURE:
<223> OTHER INFORMATION: F16 CDR2 VH

<400> SEQUENCE: 60

Ala Ile Ser Gly Ser Gly Gly Ser Thr Tyr Tyr Ala Asp Ser Val Lys
1               5                   10                  15

Gly

<210> SEQ ID NO 61
<211> LENGTH: 7
<212> TYPE: PRT
<213> ORGANISM: Artificial Sequence
<220> FEATURE:
<223> OTHER INFORMATION: F16 CDR3 VH

<400> SEQUENCE: 61

Ala His Asn Ala Phe Asp Tyr
1               5

<210> SEQ ID NO 62
<211> LENGTH: 11
<212> TYPE: PRT
<213> ORGANISM: Artificial Sequence
<220> FEATURE:
<223> OTHER INFORMATION: F16 CDR1 VL

<400> SEQUENCE: 62

Gln Gly Asp Ser Leu Arg Ser Tyr Tyr Ala Ser
1               5                   10

```
<210> SEQ ID NO 63
<211> LENGTH: 7
<212> TYPE: PRT
<213> ORGANISM: Artificial Sequence
<220> FEATURE:
<223> OTHER INFORMATION: F16 CDR2 VL

<400> SEQUENCE: 63

Gly Lys Asn Asn Arg Pro Ser
1               5

<210> SEQ ID NO 64
<211> LENGTH: 11
<212> TYPE: PRT
<213> ORGANISM: Artificial Sequence
<220> FEATURE:
<223> OTHER INFORMATION: F16 CDR3 VL

<400> SEQUENCE: 64

Asn Ser Ser Val Tyr Thr Met Pro Pro Val Val
1               5                   10

<210> SEQ ID NO 65
<211> LENGTH: 118
<212> TYPE: PRT
<213> ORGANISM: Artificial Sequence
<220> FEATURE:
<223> OTHER INFORMATION: G11 VH

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
                20                  25                  30

Arg Met Gly Trp Val Arg Gln Ala Pro Gly Lys Gly Leu Glu Trp Val
            35                  40                  45

Ser Ala Ile Asn Glu Glu Gly Gly Gln Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys His Pro Pro His Arg Pro Phe Asp Tyr Trp Gly Gln Gly Thr
            100                 105                 110

Leu Val Thr Val Ser Arg
        115

<210> SEQ ID NO 66
<211> LENGTH: 109
<212> TYPE: PRT
<213> ORGANISM: Artificial Sequence
<220> FEATURE:
<223> OTHER INFORMATION: G11 - VL

<400> SEQUENCE: 66

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Leu Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
```

```
                 50                  55                  60
Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Ser His Gly Pro Arg Arg Pro
                 85                  90                  95

Val Val Phe Gly Gly Gly Thr Lys Leu Thr Val Leu Gly
                100                 105

<210> SEQ ID NO 67
<211> LENGTH: 14
<212> TYPE: PRT
<213> ORGANISM: Artificial Sequence
<220> FEATURE:
<223> OTHER INFORMATION: scFv VH - VL domain linker sequence

<400> SEQUENCE: 67

Gly Gly Gly Gly Ser Gly Gly Gly Gly Ser Gly Gly Gly Gly
1               5                   10

<210> SEQ ID NO 68
<211> LENGTH: 5
<212> TYPE: PRT
<213> ORGANISM: Artificial Sequence
<220> FEATURE:
<223> OTHER INFORMATION: Diabody VH - VL domain linker sequence

<400> SEQUENCE: 68

Gly Gly Ser Gly Gly
1               5

<210> SEQ ID NO 69
<211> LENGTH: 117
<212> TYPE: PRT
<213> ORGANISM: Artificial Sequence
<220> FEATURE:
<223> OTHER INFORMATION: Alternative VH domain sequence for antibody
      CT01

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Glu Trp Val
                35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Lys Pro Ala Pro Arg Ala Arg Phe Asp Tyr Trp Gly Gln Gly Thr
                100                 105                 110

Leu Val Thr Val Ser
        115

<210> SEQ ID NO 70
<211> LENGTH: 117
<212> TYPE: PRT
<213> ORGANISM: Artificial Sequence
<220> FEATURE:
<223> OTHER INFORMATION: Alternative VH domain sequence for antibody
```

FF01

<400> SEQUENCE: 70

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Thr Trp Asn Asn Tyr Phe Asp Tyr Trp Gly Gln Gly Thr
            100                 105                 110

Leu Val Thr Val Ser
        115

<210> SEQ ID NO 71
<211> LENGTH: 115
<212> TYPE: PRT
<213> ORGANISM: Artificial Sequence
<220> FEATURE:
<223> OTHER INFORMATION: Alternative VH domain sequence for antibody
      2PC10

<400> SEQUENCE: 71

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Ala
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ala Pro Met Phe Asp Tyr Trp Gly Gln Gly Thr Leu Val
            100                 105                 110

Thr Val Ser
        115

<210> SEQ ID NO 72
<211> LENGTH: 115
<212> TYPE: PRT
<213> ORGANISM: Artificial Sequence
<220> FEATURE:
<223> OTHER INFORMATION: Alternative VH domain sequence for antibody
      CPR01

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Glu Trp Val
        35                  40                  45

Ser Ala Ile Lys Ala Arg Gly Gly Leu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Gly Gly Ala Pro Phe Asp Tyr Trp Gly Gln Gly Thr Leu Val
                100                 105                 110

Thr Val Ser
        115
```

<210> SEQ ID NO 73
<211> LENGTH: 108
<212> TYPE: PRT
<213> ORGANISM: Artificial Sequence
<220> FEATURE:
<223> OTHER INFORMATION: Alternative VL domain sequence for antibody SW01

<400> SEQUENCE: 73

```
Ser Glu Leu Thr Gln Asp Pro Ala Val Ser Val Ala Leu Gly Gln Thr
 1               5                  10                  15

Val Arg Ile Thr Cys Gln Gly Asp Ser Leu Arg Ser Tyr Tyr Ala Ser
                 20                  25                  30

Trp Tyr Gln Gln Lys Pro Gly Gln Ala Pro Val Leu Val Ile Tyr Gly
         35                  40                  45

Lys Asn Asn Arg Pro Ser Gly Ile Pro Asp Arg Phe Ser Gly Ser Ser
 50                  55                  60

Ser Gly Asn Thr Ala Ser Leu Thr Ile Thr Gly Ala Gln Ala Glu Asp
 65                  70                  75                  80

Glu Ala Asp Tyr Tyr Cys Asn Ser Ser Pro Lys Ala Pro Arg Pro Val
                 85                  90                  95

Val Phe Gly Gly Gly Thr Lys Leu Thr Val Leu Gly
                100                 105
```

<210> SEQ ID NO 74
<211> LENGTH: 118
<212> TYPE: PRT
<213> ORGANISM: Artificial Sequence
<220> FEATURE:
<223> OTHER INFORMATION: FF02 - VH

<400> SEQUENCE: 74

```
Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                 20                  25                  30

Ala Met Ser Trp Val Arg Gln Ala Pro Gly Lys Gly Leu Glu Trp Val
         35                  40                  45

Ser Ala Ile Lys Gly Ser Gly Gly Ser Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Trp Asn Trp Asn Leu Glu Phe Asp Tyr Trp Gly Gln Gly Thr
            100                 105                 110

Leu Val Thr Val Ser Ser
        115

<210> SEQ ID NO 75
<211> LENGTH: 109
<212> TYPE: PRT
<213> ORGANISM: Artificial Sequence
<220> FEATURE:
<223> OTHER INFORMATION: FF02 - VL

<400> SEQUENCE: 75

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Gly Leu Ile Trp Pro Arg
                85                  90                  95

Val Val Phe Gly Gly Gly Thr Lys Leu Thr Val Leu Gly
            100                 105

<210> SEQ ID NO 76
<211> LENGTH: 10
<212> TYPE: PRT
<213> ORGANISM: Artificial Sequence
<220> FEATURE:
<223> OTHER INFORMATION: FF02 - VH CDR1

<400> SEQUENCE: 76

Gly Phe Thr Phe Ser Ser Tyr Ala Met Ser
1               5                   10

<210> SEQ ID NO 77
<211> LENGTH: 17
<212> TYPE: PRT
<213> ORGANISM: Artificial Sequence
<220> FEATURE:
<223> OTHER INFORMATION: FF02 - VH CDR2

<400> SEQUENCE: 77

Ala Ile Lys Gly Ser Gly Gly Ser Thr Tyr Tyr Ala Asp Ser Val Lys
1               5                   10                  15

Gly

<210> SEQ ID NO 78
<211> LENGTH: 9
<212> TYPE: PRT
<213> ORGANISM: Artificial Sequence
<220> FEATURE:
<223> OTHER INFORMATION: FF02 - VH CDR3

<400> SEQUENCE: 78

Trp Asn Trp Asn Leu Glu Phe Asp Tyr
1               5

```
<210> SEQ ID NO 79
<211> LENGTH: 11
<212> TYPE: PRT
<213> ORGANISM: Artificial Sequence
<220> FEATURE:
<223> OTHER INFORMATION: FF02 - VL CDR1

<400> SEQUENCE: 79

Gln Gly Asp Ser Leu Arg Ser Tyr Tyr Ala Ser
1               5                   10

<210> SEQ ID NO 80
<211> LENGTH: 7
<212> TYPE: PRT
<213> ORGANISM: Artificial Sequence
<220> FEATURE:
<223> OTHER INFORMATION: FF02 - VL CDR2

<400> SEQUENCE: 80

Gly Lys Asn Asn Arg Pro Ser
1               5

<210> SEQ ID NO 81
<211> LENGTH: 11
<212> TYPE: PRT
<213> ORGANISM: Artificial Sequence
<220> FEATURE:
<223> OTHER INFORMATION: FF02 - VL CDDR3

<400> SEQUENCE: 81

Asn Ser Ser Gly Leu Ile Trp Pro Arg Val Val
1               5                   10

<210> SEQ ID NO 82
<211> LENGTH: 362
<212> TYPE: PRT
<213> ORGANISM: Artificial Sequence
<220> FEATURE:
<223> OTHER INFORMATION: FF02 in SIP format

<400> SEQUENCE: 82

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Trp Asn Trp Asn Leu Glu Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Ser Glu Leu Thr Gln Asp Pro Ala Val Ser Val
    130                 135                 140

Ala Leu Gly Gln Thr Val Arg Ile Thr Cys Gln Gly Asp Ser Leu Arg
145                 150                 155                 160

Ser Tyr Tyr Ala Ser Trp Tyr Gln Gln Lys Pro Gly Gln Ala Pro Val
```

```
                    165                 170                 175
Leu Val Ile Tyr Gly Lys Asn Asn Arg Pro Ser Gly Ile Pro Asp Arg
            180                 185                 190

Phe Ser Gly Ser Ser Gly Asn Thr Ala Ser Leu Thr Ile Thr Gly
        195                 200                 205

Ala Gln Ala Glu Asp Glu Ala Asp Tyr Tyr Cys Asn Ser Ser Gly Leu
        210                 215                 220

Ile Trp Pro Arg Val Val Phe Gly Gly Thr Lys Leu Thr Val Leu
225                 230                 235                 240

Gly Ser Gly Gly Ser Gly Gly Pro Arg Ala Ala Pro Glu Val Tyr Ala
                245                 250                 255

Phe Ala Thr Pro Glu Trp Pro Gly Ser Arg Asp Lys Arg Thr Leu Ala
            260                 265                 270

Cys Leu Ile Gln Asn Phe Met Pro Glu Asp Ile Ser Val Gln Trp Leu
            275                 280                 285

His Asn Glu Val Gln Leu Pro Asp Ala Arg His Ser Thr Thr Gln Pro
        290                 295                 300

Arg Lys Thr Lys Gly Ser Gly Phe Phe Val Phe Ser Arg Leu Glu Val
305                 310                 315                 320

Thr Arg Ala Glu Trp Glu Gln Lys Asp Glu Phe Ile Cys Arg Ala Val
                325                 330                 335

His Glu Ala Ala Ser Pro Ser Gln Thr Val Gln Arg Ala Val Ser Val
            340                 345                 350

Asn Pro Glu Ser Ser Arg Arg Gly Gly Cys
        355                 360

<210> SEQ ID NO 83
<211> LENGTH: 5
<212> TYPE: PRT
<213> ORGANISM: Artificial Sequence
<220> FEATURE:
<223> OTHER INFORMATION: Linkder sequence linking VL domain to CH4
      domain of human IgE

<400> SEQUENCE: 83

Ser Gly Gly Ser Gly
1               5

<210> SEQ ID NO 84
<211> LENGTH: 116
<212> TYPE: PRT
<213> ORGANISM: Artificial Sequence
<220> FEATURE:
<223> OTHER INFORMATION: Amino acid sequence of the CH4 domain of human
      IgE

<400> SEQUENCE: 84

Gly Pro Arg Ala Ala Pro Glu Val Tyr Ala Phe Ala Thr Pro Glu Trp
1               5                   10                  15

Pro Gly Ser Arg Asp Lys Arg Thr Leu Ala Cys Leu Ile Gln Asn Phe
            20                  25                  30

Met Pro Glu Asp Ile Ser Val Gln Trp Leu His Asn Glu Val Gln Leu
        35                  40                  45

Pro Asp Ala Arg His Ser Thr Thr Gln Pro Arg Lys Thr Lys Gly Ser
    50                  55                  60

Gly Phe Phe Val Phe Ser Arg Leu Glu Val Thr Arg Ala Glu Trp Glu
65                  70                  75                  80

Gln Lys Asp Glu Phe Ile Cys Arg Ala Val His Glu Ala Ala Ser Pro
```

```
                85                  90                  95
Ser Gln Thr Val Gln Arg Ala Val Ser Val Asn Pro Glu Ser Ser Arg
                100                 105                 110

Arg Gly Gly Cys
        115

<210> SEQ ID NO 85
<211> LENGTH: 108
<212> TYPE: PRT
<213> ORGANISM: Artificial Sequence
<220> FEATURE:
<223> OTHER INFORMATION: FF01 - alternative amino acid sequence of the
      VL domain

<400> SEQUENCE: 85

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Pro Asp Gly Arg Gly
                85                  90                  95

Val Val Phe Gly Gly Gly Thr Lys Leu Thr Val Leu
            100                 105

<210> SEQ ID NO 86
<211> LENGTH: 10
<212> TYPE: PRT
<213> ORGANISM: Artificial Sequence
<220> FEATURE:
<223> OTHER INFORMATION: FF01 - alternative amino acid sequenceof the VH
      CDR2

<400> SEQUENCE: 86

Ala Ile Lys Gly Ser Gly Gly Ser Thr Tyr
1               5                   10

<210> SEQ ID NO 87
<211> LENGTH: 108
<212> TYPE: PRT
<213> ORGANISM: Artificial Sequence
<220> FEATURE:
<223> OTHER INFORMATION: CPR01 - alternative amino acid sequence of the
      VL domain

<400> SEQUENCE: 87

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
        50                  55                  60

Ser Ser Gly Asn Thr Ala Ser Leu Thr Ile Thr Gly Ala Gln Ala Glu
65                  70                  75                  80
```

```
Asp Glu Ala Asp Tyr Tyr Cys Asn Ser Ser Pro Leu Asn Arg Leu Ala
                85                  90                  95

Val Val Phe Gly Gly Gly Thr Lys Leu Thr Val Leu
            100                 105

<210> SEQ ID NO 88
<211> LENGTH: 108
<212> TYPE: PRT
<213> ORGANISM: Artificial Sequence
<220> FEATURE:
<223> OTHER INFORMATION: F16 - alternative amino acid sequence of the VL
      domain

<400> SEQUENCE: 88

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Val Tyr Thr Met Pro Pro
                85                  90                  95

Val Val Phe Gly Gly Gly Thr Lys Leu Thr Val Leu
            100                 105

<210> SEQ ID NO 89
<211> LENGTH: 116
<212> TYPE: PRT
<213> ORGANISM: Artificial Sequence
<220> FEATURE:
<223> OTHER INFORMATION: CPR01.1 - VH

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Ala Pro Phe Asp Tyr Trp Gly Gln Gly Thr Leu Val
            100                 105                 110

Thr Val Ser Ser
        115

<210> SEQ ID NO 90
<211> LENGTH: 109
<212> TYPE: PRT
<213> ORGANISM: Artificial Sequence
<220> FEATURE:
```

<223> OTHER INFORMATION: CPR01.1 - VL

<400> SEQUENCE: 90

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ser Leu Arg Gly Thr Leu Pro
                85                  90                  95

Val Val Phe Gly Gly Gly Thr Lys Leu Thr Val Leu Gly
            100                 105

<210> SEQ ID NO 91
<211> LENGTH: 17
<212> TYPE: PRT
<213> ORGANISM: Artificial Sequence
<220> FEATURE:
<223> OTHER INFORMATION: CPR01.1 - VH CDR2

<400> SEQUENCE: 91

Ala Ile Lys Gly Ser Gly Gly Ser Thr Tyr Tyr Ala Asp Ser Val Lys
1               5                   10                  15

Gly

<210> SEQ ID NO 92
<211> LENGTH: 11
<212> TYPE: PRT
<213> ORGANISM: Artificial Sequence
<220> FEATURE:
<223> OTHER INFORMATION: CPR01.1 - VL CDR3

<400> SEQUENCE: 92

Asn Ser Ser Leu Arg Gly Thr Leu Pro Val Val
1               5                   10

<210> SEQ ID NO 93
<211> LENGTH: 239
<212> TYPE: PRT
<213> ORGANISM: Artificial Sequence
<220> FEATURE:
<223> OTHER INFORMATION: synthetic sequence

<400> SEQUENCE: 93

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Lys Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
              85                  90                  95
Ala Lys Gly Gly Ala Pro Phe Asp Tyr Trp Gly Gln Gly Thr Leu Val
            100                 105                 110

Thr Val Ser Ser Gly Gly Gly Ser Gly Gly Gly Gly Ser Gly Gly
        115                 120                 125

Gly Gly Ser Ser Glu Leu Thr Gln Asp Pro Ala Val Ser Val Ala Leu
    130                 135                 140

Gly Gln Thr Val Arg Ile Thr Cys Gln Gly Asp Ser Leu Arg Ser Tyr
145                 150                 155                 160

Tyr Ala Ser Trp Tyr Gln Gln Lys Pro Gly Gln Ala Pro Val Leu Val
                165                 170                 175

Ile Tyr Gly Lys Asn Asn Arg Pro Ser Gly Ile Pro Asp Arg Phe Ser
            180                 185                 190

Gly Ser Ser Ser Gly Asn Thr Ala Ser Leu Thr Ile Thr Gly Ala Gln
        195                 200                 205

Ala Glu Asp Glu Ala Asp Tyr Tyr Cys Asn Ser Ser Leu Arg Gly Thr
    210                 215                 220

Leu Pro Val Val Phe Gly Gly Gly Thr Lys Leu Thr Val Leu Gly
225                 230                 235
```